US011493518B2

(12) United States Patent
Kunkel et al.

(10) Patent No.: US 11,493,518 B2
(45) Date of Patent: Nov. 8, 2022

(54) BINDING DOMAIN MAPPING

(71) Applicant: George Mason Research Foundation, Inc., Fairfax, VA (US)

(72) Inventors: Alessandra Luchini Kunkel, Fairfax, CA (US); Lance Liotta, Fairfax, VA (US); Virginia Espina, Fairfax, VA (US)

(73) Assignee: GEORGE MASON RESEARCH FOUNDATION, INC., Fairfax, VA (US)

(*) Notice: Subject to any disclaimer, the term of this patent is extended or adjusted under 35 U.S.C. 154(b) by 719 days.

(21) Appl. No.: 16/140,583

(22) Filed: Sep. 25, 2018

(65) Prior Publication Data

US 2019/0033319 A1 Jan. 31, 2019

Related U.S. Application Data

(62) Division of application No. 14/758,749, filed as application No. PCT/US2014/011619 on Jan. 15, 2014, now Pat. No. 10,126,304.

(60) Provisional application No. 61/753,226, filed on Jan. 16, 2013.

(51) Int. Cl.

| | |
|---|---|
| ***G01N 33/00*** | (2006.01) |
| ***G01N 33/68*** | (2006.01) |
| ***G01N 33/53*** | (2006.01) |
| ***C07K 16/28*** | (2006.01) |

(52) U.S. Cl.
CPC ..... *G01N 33/6845* (2013.01); *C07K 16/2866* (2013.01); *G01N 33/53* (2013.01); *G01N 33/68* (2013.01); *G01N 33/6848* (2013.01); *C07K 2317/76* (2013.01); *G01N 2458/00* (2013.01)

(58) Field of Classification Search
CPC .................................................. G01N 33/6845
USPC .......................................................... 436/86
See application file for complete search history.

(56) References Cited

U.S. PATENT DOCUMENTS

2002/0042080 A1 4/2002 Woods
2015/0338417 A1 11/2015 Luchini et al.

FOREIGN PATENT DOCUMENTS

EP 0361991 A2 4/1990
EP 2311939 A1 4/2011
WO 2014/113433 A1 7/2014

OTHER PUBLICATIONS

Akasaka, Kazuaki "Simple determination of L-ascorbic acid on TLC by visual detection using autocatalytic reaction" Analytical Sciences (2013), 29(5), 505-509. (Year: 2013).*
Bi, S. et al. (2005) Spectroscopic Characterization of Effective Components Anthraquinones in Chinese Medicinal Herbs Binding with Serum Albumins. Spectrochimica Acta, Part A. 62:203-12.
(Continued)

*Primary Examiner* — Christine T Mui
*Assistant Examiner* — Emily R. Berkeley
(74) *Attorney, Agent, or Firm* — Saul Ewing Arnstein & Lehr LLP; Alireza Behrooz

(57) ABSTRACT

The present disclosure relates to compositions and methodology for revealing binding sites between proteins, proteins and nucleic acids, or proteins and small molecules. The disclosure provides rapid and direct positive identification and sequencing of the contact region between such molecules, and can be applied to individual interacting pairs, as well as large-scale or global interactions.

11 Claims, 37 Drawing Sheets

Specification includes a Sequence Listing.

(56) References Cited

OTHER PUBLICATIONS

Fei Ding, Wei Liu, Jian-Xiong Diao, Ying Sun "Characterization of Alizarin Red S binding sites and structural changes on human serum albumin: A biophysical study" Journal of Hazardous Materials 186 (2011) 352-359 (Year: 2011).

T.K.S. Kumar, G. Jayaraman, W.Y. Lin, C. Yu "Effect of chaotropic denaturant on the binding of 1-anilino-8-naphthalene sulfonic acid to proteins" Biochimica et Biophysica Acta 1294 (1996) 103-105 (Year: 1996).

Ngan, C.H. et al. (2012) FTMAP: Extended Protein Mapping with User-Selected Probe Molecules. Nucleic Acids Res. 40: W271-5 [online] [Retrieved from the Internet <URL:http://www.ncbi.nlm.nih.aov/pmc/articles/PMC3394268/>l.

Silverman, J.A. et al. (2002) Rapid Mapping of Protein Structure, Interactions, and Ligand Binding by Misincorporation Proton-Alkyl Exchange. J Biol Chem. 277(34):30968-75 [online] [Retrieved from the Internet <URL: http://www.jbc.org/contenU277/34/30968.full.pdf+html>].

International Search Report dated Apr. 25, 2014 for International Application No. PCT/US2014/011619, which was filed on Jan. 15, 2014 (Inventors—Luchini et al.; (4 Pages)).

Written Opinion dated Apr. 25, 2014 for International Application No. PCT/US2014/011619, which was filed on Jan. 15, 2014 (Inventors—Luchini et al.; (12 Pages)).

International Preliminary Report on Patentability dated Jul. 21, 2015 for International Application No. PCT/US2014/011619, which was filed on Jan. 15, 2014 (Inventors—Luchini et al.; (13 Pages)).

* cited by examiner

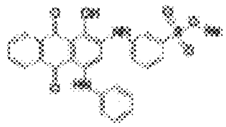
Alizarin Blue Black B
(ABB)
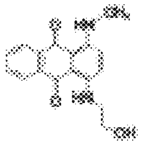
Disperse Blue 3
(DB3)
Remazol Brilliant Blue R
(RBB)
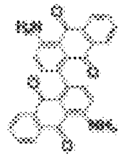
Pigment Red 177
(PR1)
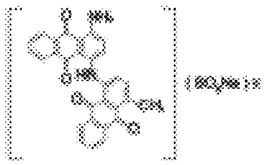
Acid Black 48
(AB4)
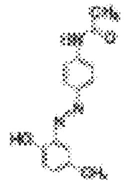
Disperse Yellow 3
(DB3)
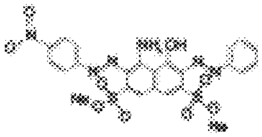
Acid Black 1
(AB1)
Disperse Orange 3
(DO3)
Disperse Yellow 9
(DY9)
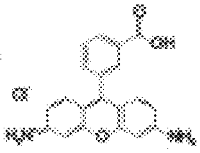
Rhodamine 123
(R12)
Toluidine Blue O
(TBO)
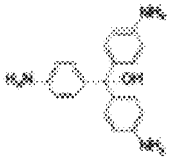
Pararosaniline Base
(PR)
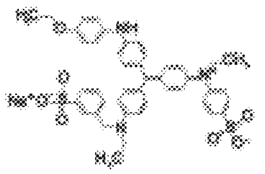
Brilliant Blue R-250
(BB)
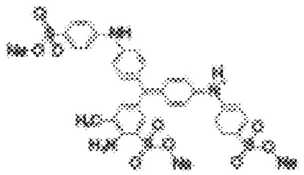
Acid Blue 22
(AB2)
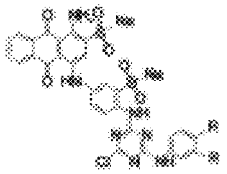
Cibacron Blue F3GA
(CB)
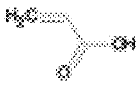
Acrylic Acid
(AAc)
Vinyl Sulfonic Acid
(VSA)
FIG. 2

Step1 (5 minutes):
paints saturate solvent
accessible surfaces
of native proteins

Step 2 (1 minutes):
unbound paint
washed off by gel
filtration

Step 3: protein
complex denatured
and dissociated

Step 4: proteins
are linearized by reduction
and alkylation

Step 5: linearized
proteins are trypsin
digested

Step 6: tryptic fragments
are identified by LC-MS/MS

| | Chemical Name (abbreviation) | MW | $_{off}$ $10^{-5}$ $s^{-1}$ | Bound after protein reduction and al ylation | Water soluble |
|---|---|---|---|---|---|
| 1 | sodium 4-(4-(benzyl-et-amino)-ph-azo)-2,5-di-cl-benzenesulfonate (AO50) | 486.356 | 5.725 | Y | Y |
| 2 | disodium 1-amino-9, 10-dio o-4- 3-(2-sulfonatoo yethylsulfonyl)anilino anthra cene-2-sulfonate (RBB) | 626.54 | 3.222 | Y | Y |
| 3 | phenyl 4- (1-amino-4-hydro y-9,10-dio o-9,10-dihydro-2-anthracenyl)o y benzenesulfonate (R49) | 487.492 | 5.899 | Y | Y |
| 4 | disodium 4-amino-3- 4- 4- (1-amino-4-sulfonatonaphthalen-2-yl)diazenyl phenyl phenyl diazenyl naphthalene-1-sulfonate (CR) | 696.66 | 2.538 | Y | Y |

FIG. 9A

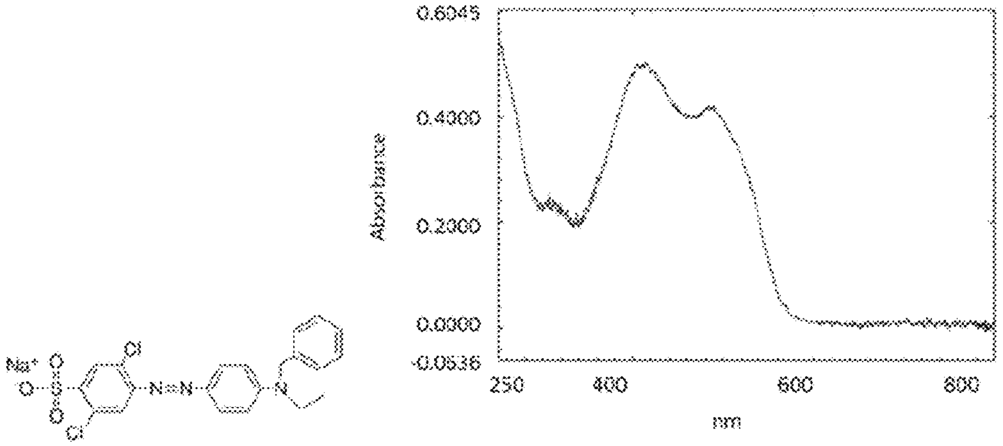

| Class | CAS number | Name | Formula |
|---|---|---|---|
| Anthra uinone | 5517-38-4 | phenyl 4- (1-amino-4-hydro y-9,10-dio o-9,10-dihydro-2-anthracenyl)o y benzenesulfonate | 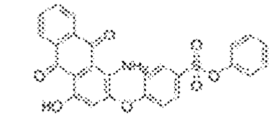 |
| Anthra uinone | 1390-65-4 | 3,5,6,8-tetrahydro y-1-methyl-9,10-dio o-7- 3,4,5-trihydro y-6-(hydro ymethyl)o an-2-yl anthracene-2-carbo ylic acid | 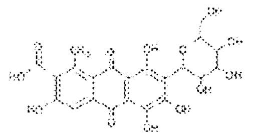 |
| Anthra uinone | 2580-78-1 | disodium 1-amino-9, 10-dio o-4- 3-(2-sulfonatoo yethylsulfonyl)anilino anthracene-2-sulfonate | 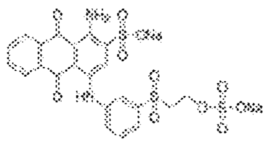 |
| Aryl azo compound | 10214-07-0 | Sodium 4-(4-(benzyl-et-amino)-ph-azo)-2,5-di-cl-benzenesulfonate | 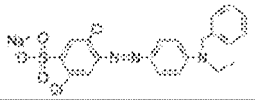 |
| Aryl azo compound | 68806-22-4 | Sodium 4- (4-metho y-1-naphthyl)diazenyl benzenesulfonate | 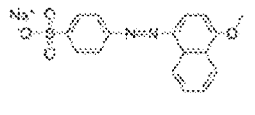 |
| Aryl azo compound | 573-58-0 | disodium 4-amino-3- 4- 4- (1-amino-4-sulfonatonaphthalen-2-yl)diazenyl phenyl phenyl diazenyl naphthalene-1-sulfonate | 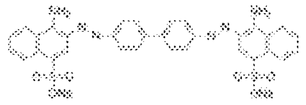 |
| Aryl azo compound | 1936-15-8 | 7-Hydro y-8-phenylazo-1,3-naphthalenedisulfonic acid disodium salt | 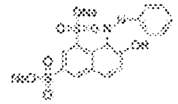 |
| anthene | 2321-07-5 | 3 ,6 -dihydro y-Spiro isobenzofuran-1(3H),9 - 9H anthen -3-one | 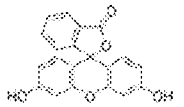 |
| anthene | 92-83-1 | anthene |  |
| anthene | 548-24-3 | 4 ,5 -dibromo-3 ,6 -dihydro y-2 ,7 -dinitro- spiro isobenzofuran-1(3H),9 - 9H anthen -3-one | 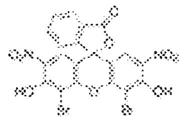 |

FIG. 10B

| Class | CAS number | Name | Formula |
|---|---|---|---|
| Thiazine | 531-53-3 | 3-amino-7-(dimethylamino)-Phenothiazin-5-ium, chloride | 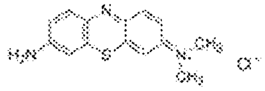 |
| Triarylmethane compound | 8004-87-3 | N-(4- bis 4-(dimethylamino)phenyl methylene -2,5-cyclohe adien-1-ylidene)methanaminium chloride | 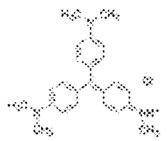 |
| Triarylmethane compound | 28983-56-4 | 4- bis 4-(sulfophenyl)amino phenyl methylene -2,5-cyclohe adien-1-ylidene amino -Benzenesulfonic acid, sodium salt (1:2) | 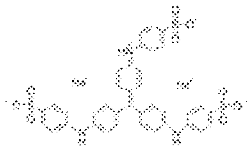 |
| Triarylmethane compound | 3244-88-0 | 2-amino-5- (4-amino-3-sulfophenyl)(4-imino-3-sulfo-2,5-cyclohe adien-1-ylidene)methyl -3-methyl-Benzenesulfonic acid, sodium salt | 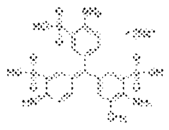 |
| Polymethine compound | 905-97-5 | 3,3 -Diethylthiacarbocyanine iodide | 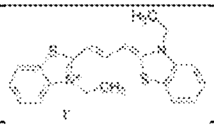 |
| Polymethine compound | 23302-83-2 | 4- 2-(1-methyl-4(1H)-pyridinylidene)ethylidene -2,5-Cyclohe adien-1-one, | 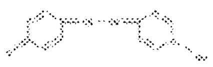 |
| Polymethine compound | 2768-90-3 | (2E)-1-ethyl-2- (E)-3-(1-ethyl uinolin-1-ium-2-yl)prop-2-enylidene uinoline chloride | 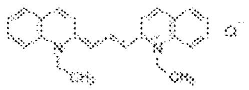 |
| Polymethine compound | 4727-49-5 | 1,1 -Diethyl-4,4 -cyanine iodide | 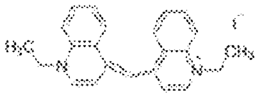 |
| Polymethine compound | 514-73-8 | 3-Ethyl-2- 5-(3-ethyl-2(3H)-benzothiazolylidene)-1,3-pentadienyl benzothiazolium iodide | 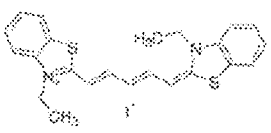 |

FIG. 10C
| Class | CAS number | Name | Formula |
|---|---|---|---|
| Naphthalene derivative | 82-76-8 | 8-Anilino-1-naphthalenesulfonic acid | 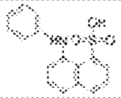 |
| Naphthalene derivative | 65664-81-5 | 4,4-Dianilino-1,1-binaphthyl-5,5-disulfonic acid dipotassium salt | 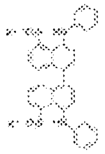 |
| Heterocyclic compound | 2390-54-7 | Thioflavine T |  |
| Heterocyclic compound | 2390-54-7 | 2- 4-(dimethylamino)phenyl -3,6-dimethyl-Benzothiazolium, chloride | 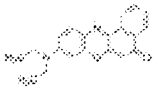 |

*Painted* MSHHWGYGKHNGPEHWHKDFPIANGERQSPVDIDTKAVVQDPALKPLALVYGEAT
*Unpainted* MSHHWGYGKHNGPEHWHKDFPIANGERQSPVDIDTKAVVQDPALKPLALVYGEAT

*Painted* SRRMVNNGHSFNVEYDDSQDKAVLKDGPLTGTYRLVQFHFHWGSSDDQGSEHTV
*Unpainted* SRRMVNNGHSFNVEYDDSQDKAVLKDGPLTGTYRLVQFHFHWGSSDDQGSEHTV

*Painted* DRKKYAAELHLVHWNTKYGDFGTAAQQPDGLAVVGVFLKVGDANPALQKVLDALD
*Unpainted* DRKKYAAELHLVHWNTKYGDFGTAAQQPDGLAVVGVFLKVGDANPALQKVLDALD

*Painted* SIKTKGKSTDFPNFDPGSLLPNVLDYWTYPGSLTTPPLLESVTWIVLKEPISVSSQQ
*Unpainted* SIKTKGKSTDFPNFDPGSLLPNVLDYWTYPGSLTTPPLLESVTWIVLKEPISVSSQQ

*Painted* MLKFRTLNFNAEGEPELLMLANWRPAQPLKNRQVRGFPK
*Unpainted* MLKFRTLNFNAEGEPELLMLANWRPAQPLKNRQVRGFPK

APVRSLNCTLRDSQQKSLVMSGPYELKALHLQGQDMEQQVVFSMSFVQGE
ESNDKIPVALGLKEKNLYLSCVLKDDKPTLQLESVDPKNYPKKKMEKRFVFNKI
EINNKLEFESAQFPNWYISTSQAENMPVFLGGTKGGQDITDFTMQFVSS

IL1RI

DKCKEREEKIILVSSANEIDVRPCPLNPNEHKGTITWYKDDSKTPVSTEQASRI
HQHKEKLWFVPAKVEDSGHYYCVVRNSSYCLRIKISAKFVENEPNLCYNAQAI
FKQKLPVAGDGGLVCPYMEFFKNENNELPKLQWYKDCKPLLLDNIHFSGVKD
RLIVMNVAEKHRGNYTCHASYTYLGKQYPITRVIEFITLEENKPTRPVIVSPANE
TMEVDLGSQIQLICNVTGQLSDIAYWKWNGSVIDEDDPVLGEDYYSVENPAN
KRRSTLITVLNISEIESRFYKHPFTCFAKNTHGIDAAYIQLIYPVTNFQK

FIG. 12A

| AA | A | B | Y |
|---|---|---|---|
| F | 120.0807757 | 148.0756904 | - |
| Y | 283.1441043 | 311.1390189 | 1298.635071 |
| K | 411.2390673 | 439.2339819 | 1135.571743 |
| H | 548.2979791 | 576.2928937 | 1007.47678 |
| P | 645.350743 | 673.3456576 | 870.417868 |
| F | 792.4191569 | 820.4140715 | 773.3651042 |
| T | 893.4668353 | 921.4617499 | 626.2966903 |
| C | 1053.497515 | 1081.49243 | 525.2490118 |
| F | 1200.565929 | 1228.560844 | 365.2183318 |
| A | 1271.603043 | 1299.597958 | 218.1499179 |
| K | - | | 147.1128041 |

Interface residue: IL1RI Lys298
Peptide: FYKHPFTCFAK
Precursor ion: 723.35068
Charge 2
Scan 1984
P(pep) 9.0E-7

| AA | A | B | Y |
|---|---|---|---|
| I | 86.09642579 | 114.0913404 | - |
| I | 199.1804898 | 227.1754044 | 2502.276964 |
| L | 312.2645537 | 340.2594683 | 2389.1929 |
| V | 411.3329676 | 439.3278822 | 2276.108836 |
| S | 498.364996 | 526.3599106 | 2177.040422 |
| S | 585.3970244 | 613.391939 | 2090.008394 |
| A | 656.4341382 | 684.4290528 | 2002.976366 |
| N | 770.4770656 | 798.4719803 | 1931.939252 |
| E | 899.5196587 | 927.5145733 | 1817.896324 |
| I | 1012.603723 | 1040.598637 | 1688.853731 |
| D | 1127.630666 | 1155.62558 | 1575.769667 |
| V | 1226.69908 | 1254.693994 | 1460.742724 |
| R | 1382.800191 | 1410.795105 | 1361.67431 |
| P | 1479.852954 | 1507.847869 | 1205.573199 |
| C | 1639.883634 | 1667.878549 | 1108.520436 |
| P | 1736.936398 | 1764.931313 | 948.4897556 |
| L | 1850.020462 | 1878.015377 | 851.4369918 |
| N | 1964.06339 | 1992.058304 | 738.3529278 |
| P | 2061.116154 | 2089.111068 | 624.3100004 |
| N | 2175.159081 | 2203.153996 | 527.2572365 |
| E | 2304.201674 | 2332.196589 | 413.2143091 |
| H | 2441.260586 | 2469.255501 | 284.171716 |
| K | - | | 147.1128041 |

Interface residue: IL1RI Lys12
Peptide: IILVSSANEIDVRPCPLNPNEHK
P (pep) 5.8E-11
Precursor ion 872.46216
Charge 3
Scan 2620

| AA | A | B | Y |
|---|---|---|---|
| L | 86.09642579 | 114.0913404 | - |
| I | 199.1804898 | 227.1754044 | 1196.6568 |
| V | 298.2489037 | 326.2438183 | 1083.5728 |
| M | 429.2893883 | 457.2843029 | 984.50436 |
| N | 543.3323157 | 571.3272303 | 853.46388 |
| V | 642.4007296 | 670.3956442 | 739.42095 |
| A | 713.4378434 | 921.4617499 | 640.35253 |
| E | 842.4804365 | 741.432758 | 569.31542 |
| K | 970.5753995 | 870.4753511 | 440.27283 |
| H | 1107.634311 | 998.5703141 | 312.17786 |
| R | - | 1135.639226 | 175.11895 |

Interface residue: IL1RI Arg163
Peptide: LIVMNVAEKHR
Precursor ion: 655.37561
Charge 2
P(pep) 2.2E-9
Scan 1542

| AA | A | B | Y |
|---|---|---|---|
| L | 86.09642579 | 114.0913404 | - |
| P | 183.1491896 | 211.1441043 | 2825.327345 |
| V | 298.2489037 | 310.2125182 | 2728.274581 |
| A | 429.2893883 | 381.2496319 | 2629.206167 |
| G | 282.2176035 | 438.2710957 | 2558.169053 |
| D | 353.2547173 | 553.2980387 | 2501.14759 |
| G | 410.276181 | 610.3195024 | 2386.120647 |
| G | 525.3031241 | 667.3409661 | 2329.099183 |
| L | 582.3245878 | 780.4250301 | 2272.077719 |
| V | 639.3460515 | 879.493444 | 2158.993655 |
| C | 752.4301155 | 1039.524124 | 2059.925241 |
| P | 851.4985294 | 1136.576888 | 1899.894561 |
| Y | 1108.581973 | 1299.640216 | 1802.841797 |
| M | 1402.685786 | 1430.680701 | 1639.778469 |
| E | 1531.728379 | 1559.723294 | 1508.737984 |
| F | 1678.796793 | 1706.791708 | 1379.695391 |
| F | 1825.865207 | 1853.860122 | 1232.626977 |
| K | 1953.96017 | 1981.955085 | 1085.558563 |
| N | 2068.003098 | 2095.998012 | 957.4636004 |
| E | 2197.045691 | 2225.040605 | 843.420673 |
| N | 2311.088618 | 2339.083533 | 714.3780799 |
| N | 2425.131546 | 2453.12646 | 600.3351525 |
| E | 2554.174139 | 2582.169053 | 486.292225 |
| L | 2667.258203 | 2695.253117 | 357.2496319 |
| P | 2764.310967 | 2792.305881 | 244.165568 |
| K | - | - | 147.1128041 |

Interface residue: IL1RI Lys 114, Lys 132163
Peptide: LPVAGDGGLVCPYMEFFKNENNELPK
Precursor ion 980.14722
Charge 3
Scan 3749
P(pep) 6.7E-16

#3749-3749 RT:33.90-33.90 NL: 9.82E3

| AA | A | B | Y |
|---|---|---|---|
| I | 86.09642579 | 114.0913404 | - |
| P | 183.1491896 | 211.1441043 | 954.5982434 |
| V | 282.2176035 | 310.2125182 | 857.5454795 |
| A | 353.2547173 | 381.2496319 | 758.4770656 |
| L | 466.3387813 | 494.3336959 | 687.4399519 |
| G | 523.360245 | 551.3551596 | 574.3558879 |
| L | 636.444309 | 664.4392236 | 517.3344242 |
| K | 764.539272 | 792.5341866 | 404.2503602 |
| E | 893.581865 | 921.5767797 | 276.1553972 |
| K | - | - | 147.1128041 |

Interface residue: IL1β Lys55
Peptide: IPVALGLKEK
Precursor ion 534.34576
Charge 2
Scan 1739
P(pep) 2.3E-5

| AA | A | B | Y |
|---|---|---|---|
| S | 60.04439023 | 89.03930485 | - |
| L | 173.1284542 | 201.233688 | 1362.679455 |
| N | 287.1713816 | 315.1662963 | 1249.595391 |
| C | 447.2020616 | 475.1969763 | 1135.552464 |
| T | 548.2497401 | 576.2446547 | 975.521784 |
| L | 661.3338041 | 689.3287187 | 874.4741055 |
| R | 817.4349151 | 845.4298297 | 761.3900416 |
| D | 932.4618581 | 960.4567727 | 605.2889306 |
| S | 1019.493886 | 1047.488801 | 490.2619875 |
| Q | 1147.552464 | 1175.547379 | 403.2299591 |
| Q | 1275.611041 | 1303.605956 | 275.1713816 |
| K | - | - | 147.1128041 |

Interface residue: IL1β Arg4-Lys 16
Peptide: SLNCTLRDSQQK
Precursor ion 725.37238
Charge 2
Scan 946
P(pep) 9.1E-8

| AA | A | B | Y |
|---|---|---|---|
| I | 86.09642579 | 114.0913404 | - |
| E | 215.1390189 | 243.1339335 | 3889.874167 |
| I | 328.2230828 | 356.2179975 | 3760.831573 |
| N | 442.2660103 | 470.2609249 | 3647.74751 |
| N | 556.3089377 | 584.3038523 | 3533.704582 |
| K | 684.4039007 | 712.3988153 | 3419.661655 |
| L | 797.4879647 | 825.4828793 | 3291.566692 |
| E | 926.5305578 | 954.5254724 | 3178.482628 |
| F | 1073.598972 | 1101.593886 | 3049.440035 |
| E | 1202.641565 | 1230.636479 | 2902.371621 |
| S | 1289.673593 | 1317.668508 | 2773.329028 |
| A | 1360.710707 | 1388.705622 | 2686.296999 |
| Q | 1488.769284 | 1516.764199 | 2615.259885 |
| F | 1635.837698 | 1663.832613 | 2487.201308 |
| P | 1732.890462 | 1760.885377 | 2340.132894 |
| N | 1846.93339 | 1874.928304 | 2243.08013 |
| W | 2033.012703 | 2061.007617 | 2129.037203 |
| Y | 2196.076031 | 2224.070946 | 1942.95789 |
| I | 2309.160095 | 2337.15501 | 1779.894561 |
| S | 2396.192123 | 2424.187038 | 1666.810497 |
| T | 2497.239802 | 2525.234716 | 1579.778469 |
| S | 2584.27183 | 2612.266745 | 1478.73079 |
| Q | 2712.330408 | 2740.325322 | 1391.698762 |
| A | 2783.367522 | 2811.362436 | 1263.640185 |
| E | 2912.410115 | 2940.405029 | 1192.603071 |
| N | 3026.453042 | 3054.447957 | 1063.560478 |
| M | 3157.493527 | 3185.488441 | 949.5175503 |
| P | 3254.546291 | 3282.541205 | 818.4770656 |
| V | 3353.614704 | 3381.609619 | 721.4243018 |
| F | 3500.683118 | 3528.678033 | 622.3558879 |
| L | 3613.767182 | 3641.762097 | 475.287474 |
| G | 3670.788646 | 3698.783561 | 362.20341 |
| G | 3727.81011 | 3755.805024 | 305.1819463 |
| T | 3828.857788 | 3856.852703 | 248.1604826 |
| K | - | | 147.1128041 |

Interface residue: IL1β Lys 103
Peptide: IEINNKLEFESAQFPNWYISTSQAENMPVFLGGTK
Precursor ion 1334.99622
Charge 3
Scan 3944
P(pep) 1.5E-12
#3944-3944 RT:35.88-35.88 NL: 4.49E2

| AA | A | B | Y |
|---|---|---|---|
| L | 86.09642579 | 114.0913404 | - |
| E | 215.1390189 | 243.1339335 | 3178.482628 |
| F | 362.2074328 | 390.2023474 | 3049.440035 |
| E | 491.2500259 | 519.2449405 | 2902.371621 |
| S | 578.2820543 | 606.2769689 | 2773.329028 |
| A | 649.319168 | 677.3140827 | 2686.296999 |
| Q | 777.3777455 | 805.3726602 | 2615.259885 |
| F | 924.4461594 | 952.4410741 | 2487.201308 |
| P | 1021.498923 | 1049.493838 | 2340.132894 |
| N | 1135.541851 | 1163.536765 | 2243.08013 |
| W | 1321.621164 | 1349.616078 | 2129.037203 |
| Y | 1484.684492 | 1512.679407 | 1942.95789 |
| I | 1597.768556 | 1625.763471 | 1779.894561 |
| S | 1684.800585 | 1712.795499 | 1666.810497 |
| T | 1785.848263 | 1813.843178 | 1579.778469 |
| S | 1872.880291 | 1900.875206 | 1478.73079 |
| Q | 2000.938869 | 2028.933784 | 1391.698762 |
| A | 2071.975983 | 2099.970897 | 1263.640185 |
| E | 2201.018576 | 2229.01349 | 1192.603071 |
| N | 2315.061503 | 2343.056418 | 1063.560478 |
| M | 2446.101988 | 2474.096902 | 949.5175503 |
| P | 2543.154752 | 2571.149666 | 818.4770656 |
| V | 2642.223166 | 2670.21808 | 721.4243018 |
| F | 2789.291579 | 2817.286494 | 622.3558879 |
| L | 2902.375643 | 2930.370558 | 475.287474 |
| G | 2959.397107 | 2987.392022 | 362.20341 |
| G | 3016.418571 | 3044.413485 | 305.1819463 |
| T | 3117.466249 | 3145.461164 | 248.1604826 |
| K | - | | 147.1128041 |

Interface residue: IL1β Lys 109
Peptide: LEFESAQFPNWYISTSQAENMPVFLGGTK
Precursor ion 1097.86499
Charge 3
Scan 4037
P(pep) 4.1E-13

#4037-4037 RT:36.72-36.72 NL:6.94E2

| AA | A | B | Y |
|---|---|---|---|
| D | 88.03930485 | 116.0342195 | - |
| S | 175.0713333 | 203.0662479 | 1694.878183 |
| Q | 303.1299108 | 331.1248254 | 1607.846155 |
| Q | 431.1884883 | 459.1834029 | 1479.787577 |
| K | 559.2834513 | 587.2783659 | 1351.729 |
| S | 646.3154797 | 674.3103943 | 1223.634037 |
| L | 759.3995436 | 787.3944582 | 1136.602008 |
| V | 858.4679575 | 886.4628721 | 1023.517944 |
| M | 989.5084421 | 1017.503357 | 924.4495303 |
| S | 1076.540471 | 1104.535385 | 793.4090457 |
| G | 1133.561934 | 1161.556849 | 706.3770173 |
| P | 1230.614698 | 1258.609613 | 649.3555535 |
| Y | 1393.678027 | 1421.672941 | 552.3027897 |
| E | 1522.72062 | 1550.715534 | 389.2394612 |
| L | 1635.804684 | 1663.799598 | 260.1968681 |
| K | - | - | 147.1128041 |

Interface residue: IL1β Arg11-Lys27
Peptide: DSQQKSLVMSGPYELK
Precursor ion 905.46307
Charge 2
Scan 1520
P(pep) 1.2E-11

| AA | A | B | Y |
|---|---|---|---|
| T | 74.06004029 | 102.0549549 | - |
| E | 203.1026334 | 231.097548 | 1432.764199 |
| D | 318.1295764 | 346.124491 | 1303.721606 |
| E | 431.1884883 | 475.1670841 | 1188.694663 |
| T | 548.2198479 | 576.2147626 | 1059.65207 |
| R | 704.320959 | 732.3158736 | 958.6043914 |
| T | 805.3686374 | 833.363552 | 802.5032804 |
| Q | 933.4272149 | 961.4221295 | 701.4556019 |
| I | 1046.511279 | 1074.506193 | 573.3970244 |
| L | 1159.595343 | 1187.590257 | 460.3129605 |
| S | 1246.627371 | 1247.622286 | 347.2288965 |
| I | 1359.711435 | 1387.70635 | 260.1968681 |
| K | - | - | 147.1128041 |

Hotspot residue: IL1RAcP Arg286
Peptide: TEDETRTQILSIK
Precursor ion 767.40955
Charge 2
P(pep) 7.2E-5
Scan 1492

#1492-1492 RT:19.87-19.87 NL: 3.50E1

| **Hydrogen bonds** | | | |
|---|---|---|---|
| *Structure 1* | *Dist [A]* | *Structure 2* | *Protein painting* |
| IL1RAcP:Asn 166 | 3.55 | IL1β:Gln 126 | Not found |
| IL1RAcP:Asn 168 | 3.05 | IL1β:Gly 140 | **IL1β:Lys 138** |
| IL1RAcP:Asn 168 | 3.89 | IL1β:Asp 142 | **IL1β:Lys 138** |
| IL1RAcP:Arg 286 | 2.49 | IL1β:Asp 54 | **IL1RAcP:Arg 286; IL1β:Lys 55** |
| IL1RAcP:Gln 165 | 3.06 | IL1β:Gln 141 | **IL1β:Lys 138** |
| **Salt bridges** | | | |
| *Structure 1* | *Dist [A]* | *Structure 2* | *Protein painting* |
| IL1RAcP:Arg 286 | 3.34 | IL1β:Asp 54 | **IL1RAcP:Arg 286; IL1b:Lys 55** |
| IL1RAcP:Glu 132 | 3.45 | IL1β:Lys 109 | **IL1β:Lys 109** |

FIG. 13C

| **Hydrogen bonds** | | | |
|---|---|---|---|
| Structure 1 | Dist A | Structure 2 | *Protein painting* |
| IL1RAcP:Gly 134 | 3.46 | IL1RI:Asp 120 | **IL1RI:Lys 114** |
| IL1RAcP:Asn 168 | 2.36 | IL1RI:Arg 163 | **IL1RI:Arg 163** |
| IL1RAcP:Thr 291 | 3.65 | IL1RI:Arg 208 | **IL1RAcP:Arg 286** |
| **Salt bridges** | | | |
| Structure 1 | Dist A | Structure 2 | *Protein painting* |
| IL1RAcP:Lys 218 | 2.95 | IL1RI:Asp 120 | **IL1RI:Lys 114** |
| IL1RAcP:His 226 | 3.49 | IL1RI:Asp 304 | **IL1RI:Lys 298** |

FIG. 13D

| | | | | | | | | | | | | | | | | | | | | | | |
|---|---|---|---|---|---|---|---|---|---|---|---|---|---|---|---|---|---|---|---|---|---|---|---|
| Arg286 pep | 1 | T | I | N | E | S | I | S | H | S | R | T | E | D | E | T | R | T | Q | I | L | S | 21 |
| Homo sapiens | 156 | T | I | N | E | S | I | S | H | S | R | T | E | D | E | T | R | T | Q | I | L | S | 176 |
| Macaca mulatta | 297 | T | I | N | E | S | I | S | H | S | R | T | E | D | E | T | R | T | Q | I | L | S | 317 |
| Pongo abelii | 297 | T | I | N | E | S | I | S | H | S | R | T | E | D | E | T | R | T | Q | I | L | S | 317 |
| Callithri acchus | 297 | T | I | N | E | S | I | S | H | S | R | T | E | D | E | T | R | T | Q | I | L | S | 317 |
| Pan troglodytes | 297 | T | I | N | E | S | I | S | H | S | R | T | E | D | E | T | R | T | Q | I | L | S | 317 |
| Gorilla gorilla | 294 | T | I | N | E | S | I | S | H | S | R | T | E | D | E | T | R | T | Q | I | L | S | 314 |
| Nomascus leucogenys | 297 | T | I | N | E | S | I | S | H | S | R | T | E | D | E | T | R | T | Q | I | L | S | 317 |
| Spermophilus tridecemlineatus | 298 | T | I | N | E | S | I | S | Y | T | K | T | E | D | E | T | R | T | Q | I | L | S | 318 |
| Rattus norvegicus | 156 | T | I | N | E | S | V | S | Y | S | S | T | E | D | E | T | R | T | Q | I | L | S | 176 |
| Mus musculus | 297 | T | I | N | E | S | V | S | Y | S | S | T | E | D | E | T | R | T | Q | I | L | S | 317 |
| Otolemur garnettii | 290 | T | I | N | E | S | I | S | L | T | R | T | E | D | E | M | R | T | Q | I | L | S | 309 |
| Mustela putorius | 62 | T | V | N | E | S | I | S | L | T | Q | T | E | D | E | T | R | T | Q | I | L | N | 82 |
| Oryctolagus cuniculus | 296 | T | I | N | E | S | L | S | Y | S | K | T | E | D | E | T | R | T | H | V | L | S | 316 |
| Felis catus | 299 | T | V | N | E | S | I | S | L | T | T | T | E | D | E | T | R | T | Q | V | L | S | 319 |
| Sus scrofa | 295 | S | I | N | E | S | V | S | L | S | K | I | E | D | E | T | R | T | Q | L | L | S | 315 |
| Cricetulus griseus | 298 | T | T | N | E | S | V | S | Y | S | T | T | E | D | E | T | R | T | Q | I | L | S | 317 |
| Heterocephalus glaber | 297 | T | I | S | E | S | T | S | Y | S | K | T | E | D | E | T | R | T | Q | V | L | S | 317 |
| Pteropus alecto | 465 | T | I | N | E | S | V | S | Q | T | K | T | E | D | E | K | R | T | Q | V | L | S | 484 |
| Canis familiaris | 299 | T | V | N | E | S | V | S | L | T | A | T | E | D | E | M | R | T | Q | I | L | N | 319 |
| Cavia porcellus | 293 | T | I | S | E | S | A | S | Y | S | T | M | E | D | E | T | R | T | Q | V | L | S | 313 |
| Bos taurus | 297 | S | V | N | E | S | V | I | L | K | V | T | E | D | E | T | R | T | Q | L | L | S | 317 |

FIG. 14

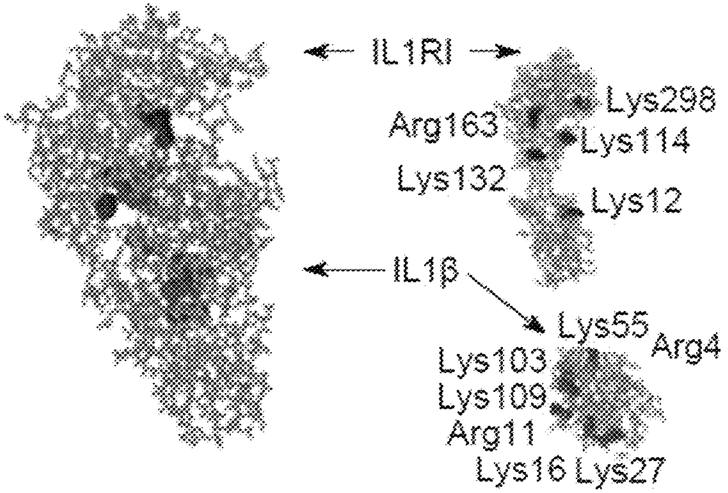
FIG. 16A
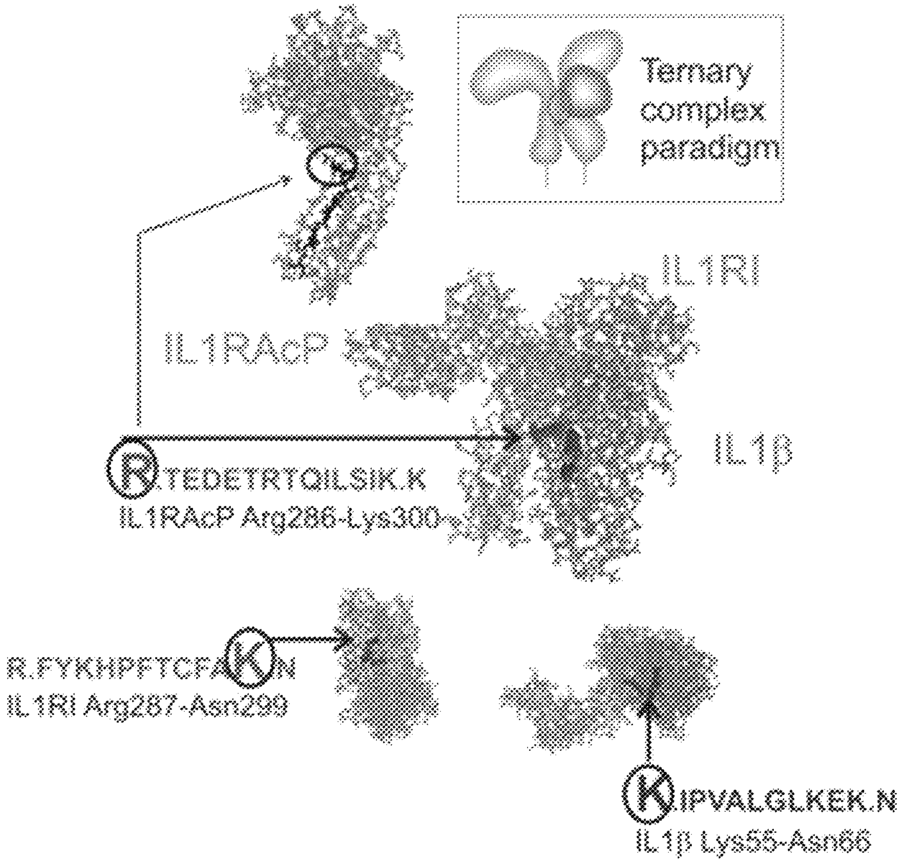
FIG. 16B
| AA | Dist [Å] | AA |
|---|---|---|
| IL1RAcP:Arg286 | 2.49 | IL1β:Asp 54 |
| IL1RI:Lys298 | 2.51 | IL1β:Ser 52 |
FIG. 16C

| Cluster | Element | FullFitness | Estimated ΔG |
|---|---|---|---|
| 17 | 0 | -2065.09 | -7.90 |

| Cluster | Element | FullFitness | Estimated ΔG |
|---|---|---|---|
| 1 | 0 | -2073.19 | -6.51 |

| Cluster | Element | FullFitness | Estimated ΔG |
|---|---|---|---|
| 18 | 0 | -2072.32 | -7.56 |

SEQUENCE LISTING

```
<160> NUMBER OF SEQ ID NOS: 42

<210> SEQ ID NO 1
<211> LENGTH: 607
<212> TYPE: PRT
<213> ORGANISM: Bos taurus
```

-continued

<400> SEQUENCE: 1

```
Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415
```

```
Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
        435                 440                 445

Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605
```

<210> SEQ ID NO 2
<211> LENGTH: 260
<212> TYPE: PRT
<213> ORGANISM: Bos taurus

<400> SEQUENCE: 2

```
Met Ser His His Trp Gly Tyr Gly Lys His Asn Gly Pro Glu His Trp
1               5                   10                  15

His Lys Asp Phe Pro Ile Ala Asn Gly Glu Arg Gln Ser Pro Val Asp
            20                  25                  30

Ile Asp Thr Lys Ala Val Val Gln Asp Pro Ala Leu Lys Pro Leu Ala
        35                  40                  45

Leu Val Tyr Gly Glu Ala Thr Ser Arg Arg Met Val Asn Asn Gly His
    50                  55                  60

Ser Phe Asn Val Glu Tyr Asp Asp Ser Gln Asp Lys Ala Val Leu Lys
65                  70                  75                  80

Asp Gly Pro Leu Thr Gly Thr Tyr Arg Leu Val Gln Phe His Phe His
                85                  90                  95

Trp Gly Ser Ser Asp Asp Gln Gly Ser Glu His Thr Val Asp Arg Lys
            100                 105                 110

Lys Tyr Ala Ala Glu Leu His Leu Val His Trp Asn Thr Lys Tyr Gly
        115                 120                 125

Asp Phe Gly Thr Ala Ala Gln Gln Pro Asp Gly Leu Ala Val Val Gly
    130                 135                 140

Val Phe Leu Lys Val Gly Asp Ala Asn Pro Ala Leu Gln Lys Val Leu
145                 150                 155                 160

Asp Ala Leu Asp Ser Ile Lys Thr Lys Gly Lys Ser Thr Asp Phe Pro
                165                 170                 175

Asn Phe Asp Pro Gly Ser Leu Leu Pro Asn Val Leu Asp Tyr Trp Thr
```

-continued

```
            180                 185                 190

Tyr Pro Gly Ser Leu Thr Thr Pro Pro Leu Leu Glu Ser Val Thr Trp
        195                 200                 205

Ile Val Leu Lys Glu Pro Ile Ser Val Ser Ser Gln Gln Met Leu Lys
    210                 215                 220

Phe Arg Thr Leu Asn Phe Asn Ala Glu Gly Glu Pro Glu Leu Leu Met
225                 230                 235                 240

Leu Ala Asn Trp Arg Pro Ala Gln Pro Leu Lys Asn Arg Gln Val Arg
                245                 250                 255

Gly Phe Pro Lys
            260


<210> SEQ ID NO 3
<211> LENGTH: 58
<212> TYPE: PRT
<213> ORGANISM: Bos taurus

<400> SEQUENCE: 3

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55


<210> SEQ ID NO 4
<211> LENGTH: 153
<212> TYPE: PRT
<213> ORGANISM: Homo sapiens

<400> SEQUENCE: 4

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150


<210> SEQ ID NO 5
<211> LENGTH: 316
<212> TYPE: PRT
```

<213> ORGANISM: Homo sapiens

<400> SEQUENCE: 5

Asp Lys Cys Lys Glu Arg Glu Glu Lys Ile Ile Leu Val Ser Ser Ala
1 5 10 15

Asn Glu Ile Asp Val Arg Pro Cys Pro Leu Asn Pro Asn Glu His Lys
20 25 30

Gly Thr Ile Thr Trp Tyr Lys Asp Asp Ser Lys Thr Pro Val Ser Thr
35 40 45

Glu Gln Ala Ser Arg Ile His Gln His Lys Glu Lys Leu Trp Phe Val
50 55 60

Pro Ala Lys Val Glu Asp Ser Gly His Tyr Tyr Cys Val Val Arg Asn
65 70 75 80

Ser Ser Tyr Cys Leu Arg Ile Lys Ile Ser Ala Lys Phe Val Glu Asn
85 90 95

Glu Pro Asn Leu Cys Tyr Asn Ala Gln Ala Ile Phe Lys Gln Lys Leu
100 105 110

Pro Val Ala Gly Asp Gly Gly Leu Val Cys Pro Tyr Met Glu Phe Phe
115 120 125

Lys Asn Glu Asn Asn Glu Leu Pro Lys Leu Gln Trp Tyr Lys Asp Cys
130 135 140

Lys Pro Leu Leu Leu Asp Asn Ile His Phe Ser Gly Val Lys Asp Arg
145 150 155 160

Leu Ile Val Met Asn Val Ala Glu Lys His Arg Gly Asn Tyr Thr Cys
165 170 175

His Ala Ser Tyr Thr Tyr Leu Gly Lys Gln Tyr Pro Ile Thr Arg Val
180 185 190

Ile Glu Phe Ile Thr Leu Glu Glu Asn Lys Pro Thr Arg Pro Val Ile
195 200 205

Val Ser Pro Ala Asn Glu Thr Met Glu Val Asp Leu Gly Ser Gln Ile
210 215 220

Gln Leu Ile Cys Asn Val Thr Gly Gln Leu Ser Asp Ile Ala Tyr Trp
225 230 235 240

Lys Trp Asn Gly Ser Val Ile Asp Glu Asp Asp Pro Val Leu Gly Glu
245 250 255

Asp Tyr Tyr Ser Val Glu Asn Pro Ala Asn Lys Arg Arg Ser Thr Leu
260 265 270

Ile Thr Val Leu Asn Ile Ser Glu Ile Glu Ser Arg Phe Tyr Lys His
275 280 285

Pro Phe Thr Cys Phe Ala Lys Asn Thr His Gly Ile Asp Ala Ala Tyr
290 295 300

Ile Gln Leu Ile Tyr Pro Val Thr Asn Phe Gln Lys
305 310 315

<210> SEQ ID NO 6
<211> LENGTH: 21
<212> TYPE: PRT
<213> ORGANISM: Artificial Sequence
<220> FEATURE:
<223> OTHER INFORMATION: synthetic construct; peptide

<400> SEQUENCE: 6

Thr Ile Asn Glu Ser Ile Ser His Ser Arg Thr Glu Asp Glu Thr Arg
1 5 10 15

Thr Gln Ile Leu Ser
20

<210> SEQ ID NO 7
<211> LENGTH: 21
<212> TYPE: PRT
<213> ORGANISM: Artificial Sequence
<220> FEATURE:
<223> OTHER INFORMATION: synthetic construct; peptide

<400> SEQUENCE: 7

His Leu Arg Asn Ile Ser Arg Ile Ser Ser Ile Thr Asp Thr Ser Glu
1 5 10 15

Thr Glu Thr Glu Gln
20

<210> SEQ ID NO 8
<211> LENGTH: 6
<212> TYPE: PRT
<213> ORGANISM: Artificial Sequence
<220> FEATURE:
<223> OTHER INFORMATION: synthetic construct; 6x His tag

<400> SEQUENCE: 8

His His His His His His
1 5

<210> SEQ ID NO 9
<211> LENGTH: 11
<212> TYPE: PRT
<213> ORGANISM: Homo sapiens

<400> SEQUENCE: 9

Phe Tyr Lys His Pro Phe Thr Cys Phe Ala Lys
1 5 10

<210> SEQ ID NO 10
<211> LENGTH: 23
<212> TYPE: PRT
<213> ORGANISM: Homo sapiens

<400> SEQUENCE: 10

Ile Ile Leu Val Ser Ser Ala Asn Glu Ile Asp Val Arg Pro Cys Pro
1 5 10 15

Leu Asn Pro Asn Glu His Lys
20

<210> SEQ ID NO 11
<211> LENGTH: 11
<212> TYPE: PRT
<213> ORGANISM: Homo sapiens

<400> SEQUENCE: 11

Leu Ile Val Met Asn Val Ala Glu Lys His Arg
1 5 10

<210> SEQ ID NO 12
<211> LENGTH: 26
<212> TYPE: PRT
<213> ORGANISM: Homo sapiens

<400> SEQUENCE: 12

Leu Pro Val Ala Gly Asp Gly Gly Leu Val Cys Pro Tyr Met Glu Phe
1 5 10 15

Phe Lys Asn Glu Asn Asn Glu Leu Pro Lys
20 25

<210> SEQ ID NO 13
<211> LENGTH: 10
<212> TYPE: PRT
<213> ORGANISM: Homo sapiens

<400> SEQUENCE: 13

Ile Pro Val Ala Leu Gly Leu Lys Glu Lys
1               5                   10

<210> SEQ ID NO 14
<211> LENGTH: 12
<212> TYPE: PRT
<213> ORGANISM: Homo sapiens

<400> SEQUENCE: 14

Ser Leu Asn Cys Thr Leu Arg Asp Ser Gln Gln Lys
1               5                   10

<210> SEQ ID NO 15
<211> LENGTH: 35
<212> TYPE: PRT
<213> ORGANISM: Homo sapiens

<400> SEQUENCE: 15

Ile Glu Ile Asn Asn Lys Leu Glu Phe Glu Ser Ala Gln Phe Pro Asn
1               5                   10                  15

Trp Tyr Ile Ser Thr Ser Gln Ala Glu Asn Met Pro Val Phe Leu Gly
            20                  25                  30

Gly Thr Lys
        35

<210> SEQ ID NO 16
<211> LENGTH: 29
<212> TYPE: PRT
<213> ORGANISM: Homo sapiens

<400> SEQUENCE: 16

Leu Glu Phe Glu Ser Ala Gln Phe Pro Asn Trp Tyr Ile Ser Thr Ser
1               5                   10                  15

Gln Ala Glu Asn Met Pro Val Phe Leu Gly Gly Thr Lys
            20                  25

<210> SEQ ID NO 17
<211> LENGTH: 16
<212> TYPE: PRT
<213> ORGANISM: Homo sapiens

<400> SEQUENCE: 17

Asp Ser Gln Gln Lys Ser Leu Val Met Ser Gly Pro Tyr Glu Leu Lys
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: synthetic construct; peptide

<400> SEQUENCE: 18

Thr Glu Asp Glu Thr Arg Thr Gln Ile Leu Ser Ile Lys
1               5                   10

<210> SEQ ID NO 19
<211> LENGTH: 21
<212> TYPE: PRT
<213> ORGANISM: Homo sapiens

<400> SEQUENCE: 19

```
Thr Ile Asn Glu Ser Ile Ser His Ser Arg Thr Glu Asp Glu Thr Arg
1               5                   10                  15

Thr Gln Ile Leu Ser
            20
```

<210> SEQ ID NO 20
<211> LENGTH: 21
<212> TYPE: PRT
<213> ORGANISM: Macaca mulatta

<400> SEQUENCE: 20

```
Thr Ile Asn Glu Ser Ile Ser His Ser Arg Thr Glu Asp Glu Thr Arg
1               5                   10                  15

Thr Gln Ile Leu Ser
            20
```

<210> SEQ ID NO 21
<211> LENGTH: 21
<212> TYPE: PRT
<213> ORGANISM: Pongo abelii

<400> SEQUENCE: 21

```
Thr Ile Asn Glu Ser Ile Ser His Ser Arg Thr Glu Asp Glu Thr Arg
1               5                   10                  15

Thr Gln Ile Leu Ser
            20
```

<210> SEQ ID NO 22
<211> LENGTH: 21
<212> TYPE: PRT
<213> ORGANISM: Callithrix jacchus

<400> SEQUENCE: 22

```
Thr Ile Asn Glu Ser Ile Ser His Ser Arg Thr Glu Asp Glu Thr Arg
1               5                   10                  15

Thr Gln Ile Leu Ser
            20
```

<210> SEQ ID NO 23
<211> LENGTH: 21
<212> TYPE: PRT
<213> ORGANISM: Pan troglodytes

<400> SEQUENCE: 23

```
Thr Ile Asn Glu Ser Ile Ser His Ser Arg Thr Glu Asp Glu Thr Arg
1               5                   10                  15

Thr Gln Ile Leu Ser
            20
```

<210> SEQ ID NO 24
<211> LENGTH: 21
<212> TYPE: PRT
<213> ORGANISM: Gorilla gorilla

<400> SEQUENCE: 24

```
Thr Ile Asn Glu Ser Ile Ser His Ser Arg Thr Glu Asp Glu Thr Arg
1               5                   10                  15
```

Thr Gln Ile Leu Ser
20

<210> SEQ ID NO 25
<211> LENGTH: 21
<212> TYPE: PRT
<213> ORGANISM: Nomascus leucogenys

<400> SEQUENCE: 25

Thr Ile Asn Glu Ser Ile Ser His Ser Arg Thr Glu Asp Glu Thr Arg
1 5 10 15

Thr Gln Ile Leu Ser
20

<210> SEQ ID NO 26
<211> LENGTH: 21
<212> TYPE: PRT
<213> ORGANISM: Spermophilus tridecemlineatus

<400> SEQUENCE: 26

Thr Ile Asn Glu Ser Ile Ser Tyr Thr Lys Thr Glu Asp Glu Thr Arg
1 5 10 15

Thr Gln Ile Leu Ser
20

<210> SEQ ID NO 27
<211> LENGTH: 21
<212> TYPE: PRT
<213> ORGANISM: Rattus norvegicus

<400> SEQUENCE: 27

Thr Ile Asn Glu Ser Val Ser Tyr Ser Ser Thr Glu Asp Glu Thr Arg
1 5 10 15

Thr Gln Ile Leu Ser
20

<210> SEQ ID NO 28
<211> LENGTH: 21
<212> TYPE: PRT
<213> ORGANISM: Mus musculus

<400> SEQUENCE: 28

Thr Ile Asn Glu Ser Val Ser Tyr Ser Ser Thr Glu Asp Glu Thr Arg
1 5 10 15

Thr Gln Ile Leu Ser
20

<210> SEQ ID NO 29
<211> LENGTH: 21
<212> TYPE: PRT
<213> ORGANISM: Otolemur garnetti

<400> SEQUENCE: 29

Thr Ile Asn Glu Ser Ile Ser Leu Thr Arg Thr Glu Asp Glu Met Arg
1 5 10 15

Thr Gln Ile Leu Ser
20

<210> SEQ ID NO 30
<211> LENGTH: 21
<212> TYPE: PRT
<213> ORGANISM: Mustela putorius

<400> SEQUENCE: 30

Thr Val Asn Glu Ser Ile Ser Leu Thr Gln Thr Glu Asp Glu Thr Arg
1 5 10 15

Thr Gln Ile Leu Asn
20

<210> SEQ ID NO 31
<211> LENGTH: 21
<212> TYPE: PRT
<213> ORGANISM: Felis catus

<400> SEQUENCE: 31

Thr Val Asn Glu Ser Ile Ser Leu Thr Thr Thr Glu Asp Glu Thr Arg
1 5 10 15

Thr Gln Val Leu Ser
20

<210> SEQ ID NO 32
<211> LENGTH: 21
<212> TYPE: PRT
<213> ORGANISM: Sus scrofa

<400> SEQUENCE: 32

Ser Ile Asn Glu Ser Val Ser Leu Ser Lys Ile Glu Asp Glu Thr Arg
1 5 10 15

Thr Gln Leu Leu Ser
20

<210> SEQ ID NO 33
<211> LENGTH: 21
<212> TYPE: PRT
<213> ORGANISM: Cricetulus griseus

<400> SEQUENCE: 33

Thr Thr Asn Glu Ser Val Ser Tyr Ser Thr Thr Glu Asp Glu Thr Arg
1 5 10 15

Thr Gln Ile Leu Ser
20

<210> SEQ ID NO 34
<211> LENGTH: 21
<212> TYPE: PRT
<213> ORGANISM: Heterocephalus glaber

<400> SEQUENCE: 34

Thr Ile Ser Glu Ser Thr Ser Tyr Ser Lys Thr Glu Asp Glu Thr Arg
1 5 10 15

Thr Gln Val Leu Ser
20

<210> SEQ ID NO 35
<211> LENGTH: 21
<212> TYPE: PRT
<213> ORGANISM: Pteropus alecto

<400> SEQUENCE: 35

Thr Ile Asn Glu Ser Val Ser Gln Thr Lys Thr Glu Asp Glu Lys Arg
1 5 10 15

Thr Gln Val Leu Ser
20

<210> SEQ ID NO 36
<211> LENGTH: 21
<212> TYPE: PRT
<213> ORGANISM: Canis familiaris

<400> SEQUENCE: 36

Thr Val Asn Glu Ser Val Ser Leu Thr Ala Thr Glu Asp Glu Met Arg
1 5 10 15

Thr Gln Ile Leu Asn
20

<210> SEQ ID NO 37
<211> LENGTH: 21
<212> TYPE: PRT
<213> ORGANISM: Cavia porcellus

<400> SEQUENCE: 37

Thr Ile Ser Glu Ser Ala Ser Tyr Ser Thr Met Glu Asp Glu Thr Arg
1 5 10 15

Thr Gln Val Leu Ser
20

<210> SEQ ID NO 38
<211> LENGTH: 21
<212> TYPE: PRT
<213> ORGANISM: Bos taurus

<400> SEQUENCE: 38

Ser Val Asn Glu Ser Val Ile Leu Lys Val Thr Glu Asp Glu Thr Arg
1 5 10 15

Thr Gln Leu Leu Ser
20

<210> SEQ ID NO 39
<211> LENGTH: 15
<212> TYPE: PRT
<213> ORGANISM: Artificial Sequence
<220> FEATURE:
<223> OTHER INFORMATION: synthetic construct; peptide

<400> SEQUENCE: 39

Arg Thr Glu Asp Glu Thr Arg Thr Gln Ile Leu Ser Ile Lys Lys
1 5 10 15

<210> SEQ ID NO 40
<211> LENGTH: 13
<212> TYPE: PRT
<213> ORGANISM: Homo sapiens

<400> SEQUENCE: 40

Arg Phe Tyr Lys His Pro Phe Thr Cys Phe Ala Lys Asn
1 5 10

<210> SEQ ID NO 41
<211> LENGTH: 12
<212> TYPE: PRT
<213> ORGANISM: Homo sapiens

<400> SEQUENCE: 41

Lys Ile Pro Val Ala Leu Gly Leu Lys Glu Lys Asn
1 5 10

<210> SEQ ID NO 42

-continued

```
<211> LENGTH: 21
<212> TYPE: PRT
<213> ORGANISM: Oryctolagus cuniculus

<400> SEQUENCE: 42

Thr Ile Asn Glu Ser Leu Ser Tyr Ser Lys Thr Glu Asp Glu Thr Arg
1               5                   10                  15

Thr His Val Leu Ser
            20
```

BINDING DOMAIN MAPPING

CROSS-REFERENCE TO RELATED APPLICATION

This application is a divisional of U.S. patent application Ser. No. 14/758,749 filed on Jun. 30, 2015, which is a National Stage Entry of International App. No. PCT/US2014/011619 filed on Jan. 15, 2014, which claims priority to U.S. Provisional Application No. 61/753,226, filed Jan. 16, 2013; and which applications are incorporated herein by reference in their entireties.

STATEMENT REGARDING GOVERNMENT FUNDING

This invention was made with government support under NIH IR21AR061075 and NIH 5R33CA173359 awarded by the National Institutes of Health. The government has certain rights in the invention.

REFERENCE TO SEQUENCE LISTING

The Sequence Listing concurrently submitted herewith as a text file named "G100_0004USD1_Sequence_Listing.txt," created on Sep. 6, 2018, and having a size of 21,774 bytes is hereby incorporated by reference pursuant to 3 7 C.F.R. § 1.52(e)(5).

FIELD

The present disclosure relates to compositions and methodology for revealing binding sites between proteins, proteins and nucleic acids, or proteins and small molecules.

INTRODUCTION

Protein-protein interactions are the fundamental functional event that drives all biologic systems at the subcellular and extracellular level. Interacting proteins drive communication within the cell and enable the cell to perceive the outside world. Protein self-interactions are constrained in a way that determines the correct folding of a protein. Protein-protein interactions define the motile machinery of the cell and the organism. Defects in protein folding, improper protein-protein interactions, or dysfunctional cellular machinery, is the functional cause of disease.

The size of the human binary interactome is estimated to comprise about 130,000 protein-protein interactions, of which only about 8% have been identified. For the vast majority of binary protein interactions that have been identified, the identity of the two interacting proteins is known but the amino acid sequence of their binding domain interface is unknown.

Characterization of the binding domain interface between interacting proteins is the starting point for the next generation of therapies that block such interactions. Traditional experimental approaches to interactomics, including Two-hybrid screening, Tandem Affinity Purification, X-ray tomography, Optical fluorescence microscopy, are error prone, time consuming, or require large amounts of protein and/or genetic tagging of the proteins. Moreover, nearly thirty percent (30%) of the identified interactions by these existing methods are artifacts. Importantly, beyond X-ray tomography/crystallography, protein interaction methods cannot identify the amino acid sequence of the interacting domains of the proteins, the regions where the interacting proteins are in intimate contact.

SUMMARY

The present disclosure embraces compositions, methodology, and the like for revealing binding sites between proteins, proteins and nucleic acids, or proteins and small molecules.

In one aspect, provided is an aryl hydrocarbon containing organic compound less than 30 Angstroms in total length taken from at least one of the following structure formulas listed below, or salts or solvates thereof, complexed or bound to a portion of a protein polypeptide chain of at least 3 amino acids where the amino acid in position 1 (P1) from the amino terminus is any amino acid, position 2 (P2) is K or R and the amino acid in position 3 (P3) is not P, (I)

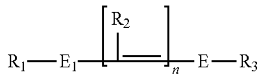

Q

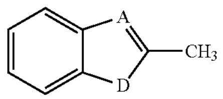

Q'

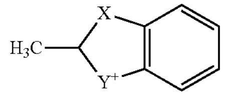

Polymethine Compounds

[wherein R1 represents H, O, halo, CO2H, NO2, SH, NR5R6, C1-6 alkyl, C1-6 alkoxy, cyano, carbonyl, pyrrolidinyl, pyrrolyl, pyrazolyl, imidazolyl, triazolyl, etc.;

R5, R6 represent H, C1-4 alkyl;

E1 represents benzene ring or ring Q

A represents CH or N;

D represents S, NH, N—C1-3 alkyl, O, or CH2;

R2 represents H, C1-4 alkyl, halo-C1-4 alkyl, HO, cyano;

n represents an integer of 1-4;

E=benzene ring or ring Q'

X represents CH or N

Y represents S, NH, N—C1-3 alkyl, O, or CH2

R3=H, O, halo, CO2H, NO2, SH, NR5R6, C1-6 alkyl, C1-6 alkoxy, cyano, carbonyl, pyrrolidinyl, pyrrolyl, pyrazolyl, imidazolyl, triazolyl, etc.)

(II)

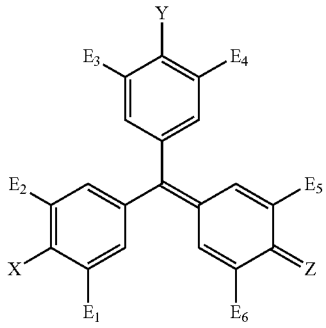

Triarylmethane compounds

[wherein X, Y, Z represent H, NR1R2, sulfa, O, halo, CO2H, NO2, SH, C1-6 alkyl, C1-6 alkoxy, etc.;

R1, R2 represent H, C1-6 alkyl, sulfophenyl;

E1, E2, E3, E4, E5, E6 represent H, sulfa, C1-6 alkyl, halo, CO2H, NO2, SH;]

(III)

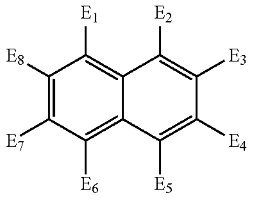

Naphthalene derivatives

[wherein E1, E2, E3, E4, E5, E6 represent H, O, C1-6 alkyl, C1-6 alkoxy, carbonyl, sulfo, NO2, NR1R2, azetidinyl, thiazolidinyl R1, R2 represent H, phenyl]

(IV)

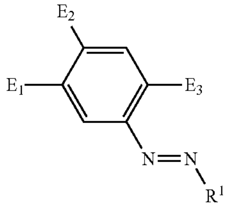

Q

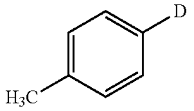

Q'

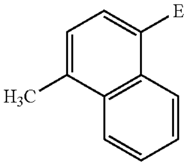

Aryl azo compounds

[wherein E1, E2, E3 represent H, halo, sulfo, O, C1-6 alkyl, C1-6 alkyl aryl;

R1 represents ring Q or ring Q';

D represents H, NR2R3;

R2, R3 represent C1-6 alkyl, C1-6 alkyl aryl;

E represents H, O, OH, C1-6 alkyloxy]

(V)

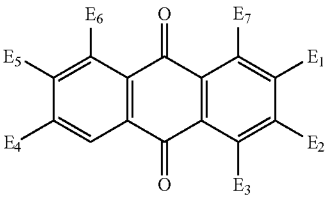

-continued

Q

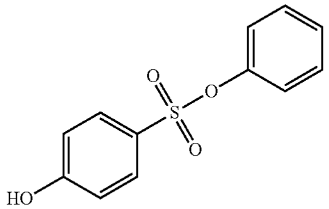

Q'

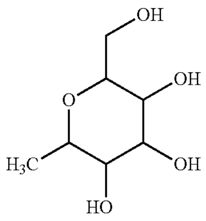

Q''

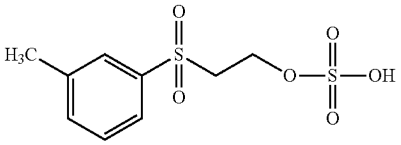

Anthraquinones

[wherein E1 represents H, NH, sulfo, Q, Q', C1-6 alkyl, OH, carboxy;

E2 represents H, NH, OH, C1-6 alkyl, sulfo;

E3 represents H, NH, OH, NR1R2, sulfo, C1-6 alkyl;

R1, R2 represent H, Q";

E4, E5, E6, E7 represent H, OH, NH, sulfa, C1-6 alkyl, carboxy]

(VI)

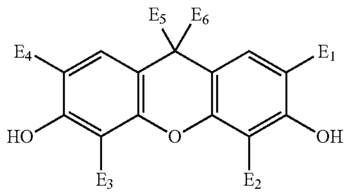

Q

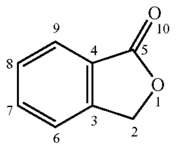

Xanthenes

[wherein E1, E2, E3, E4 represent H, NO2, OH, Halo, C1-6 alkyl;

E5, E6 represent H or Carbon in position 3 and oxygen in position 1 in group Q]

(VII)

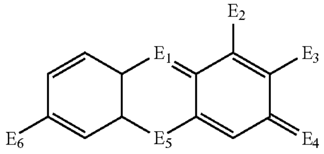

Thiazine

[wherein E1 represents N, O, S;

E2, E3 represent H, C in aryl;

E4 represents O, N, NR1R2;

R1, R2 represent C1-6 alkyl;

E5 represents N, O, S;

E6 represents H, NH, NC1-6 alkyl]

In one embodiment, an aryl hydrocarbon containing small molecule is complexed with a polypeptide chain wherein the polypeptide region complexed with the small molecule is on the surface of a single folded native protein, or two or more interacting proteins, and is exclude from an internal site within or between proteins where two protein polypeptide chains are in close proximity.

In another embodiment, the disclosure provides a method of mapping the protein-protein contact or binding domains within a single folded protein or between two or more different proteins that employs the steps of a) forming complexes with the compounds on the exposed surface of a native protein in solution, b) unfolding the protein to reveal the regions of the polypeptide chain that do not contain the complex(s), and c) analyzing the regions of the polypeptide chain that do not contain the complexes between the aryl hydrocarbons and the polypeptide chain. In a further embodiment, an unfolded protein has been cleaved by a protease such that the proteinase cleavage pattern is modified by the bound complexes. In an even further embodiment, in a modified cleavage pattern, the cleavage is performed by trypsin, Arg-C proteinase, Asp-N endopeptidase, Caspase1, Caspase2, Caspase3, Caspase4, Caspase5, Caspase6, Caspase7, Caspase8, Caspase9, Caspase10, Chymotrypsin, Clostripain (Clostridiopeptidase B), Enterokinase, Factor Xa, Glutamyl endopeptidase, GranzymeB, LysC, LysN, Pepsin, Proline-endopeptidase, Proteinase K, Staphylococcal peptidase I, Tobacco etch virus protease, Thermolysin, or Thrombin.

In another embodiment, a protein polypeptide chain in a native folded configuration in an aqueous environment in which two or more complexes with aryl hydrocarbons containing the compounds exist, such that the bound complexes remain following unfolding or denaturation of the protein polypeptide chain.

In another embodiment, the unfolded protein polypeptide chain that is bound to the complexes is further bound to an antibody or other ligand which recognizes regions of polypeptide chain that do not contain the complexes.

In another embodiment, a protein polypeptide in which the protease cleavage pattern reveals proteinase cleavage sites preferentially within the domains of the polypeptide chain that are close to protein-protein contact or binding domains within a single folded protein or between two different proteins.

In another embodiment, a protein polypeptide in which the ligand binding pattern reveals domains of the polypeptide chain that are close to protein-protein contact or binding domains within a single folded protein or between two different proteins.

In another embodiment, a protein complexed with an aryl hydrocarbon containing compound that is subject to mass spectrometry, x-ray crystallography, circular dichroism, or nuclear magnetic resonance, or absorption spectroscopy, or ligand binding assay, in which the presence or absence of the complexed aryl hydrocarbon containing compound modifies a) the mass/charge of the peptide, b) the susceptibility of the complexed region of the protein to a protease cleavage, or c) the binding of a ligand to the protein, or the diffraction or absorption pattern of the protein.

In another aspect, provided herein is a method for determining the contact region within a single folded protein or between a protein complexed with another molecule, comprising (a) introducing a mixture of small organic masking molecules to said protein, wherein said small organic masking molecules bind with high affinity to all exposed sites on said protein or protein complex, thereby coating said protein; (b) dissociating said protein or protein complex, such that the small organic masking molecules coat all areas of the protein or protein complex excluding the contact region; and (c) sequencing the contact region. In an embodiment, the molecule is a protein, nucleic acid, or small molecule.

In another aspect, protein painting was used to study the multiple hot spots participating in the three-way interaction of IL1b ligand, its receptor IL1R1, and the accessory protein IL1RAcP. Interleukin signaling requires the interaction of all three proteins. Aberrant function of this complex is involved in a variety of diseases, including cancer, rheumatoid arthritis, systemic lupus erythematosus, inflammatory bowel disease, systemic vasculitis, neonatal bronchial dysplasia, and inflammatory bone and cartilage destruction. The instant protein painting revealed a previously unknown 3-way hot spot between the accessory protein, the ligand, and the receptor. This novel information was used to create synthetic beta loop peptides corresponding to the three-way hot spot at the accessory protein. The peptide mimicking the interface blocked IL1beta signaling in ligand stimulated cells and could substitute for the entire truncated accessory protein as a competitive inhibitor. This same hot spot peptide mimic, and a monoclonal antibody raised against this sequence, blocked the three way complex formation between the IR1, IL1beta and the accessory protein. Both the peptide and the monoclonal antibody provide new therapies for treating diseases caused by aberrant interleukin signaling.

BRIEF DESCRIPTION OF THE DRAWINGS

FIG. 2: Illustrative affinity masking molecules.

(FIG. 8A) Proteins are pulsed with 10 molar excess small molecule molecular paints. (FIG. 8B) Unbound paint molecules are washed away with gel filtration chromatography (Sephadex G-25, Roche). (FIG. 8C) Protein complex is dissociated and denatured with 2 M urea. (FIG. 8D) Proteins are linearized by dithiothreitol (DTT) reduction and iodoacetamide alkylation. (FIG. 8E) Linearized proteins are subjected to trypsin digestion. (FIG. 8F) Tryptic fragments are analyzed by reversed-phase liquid chromatography nanospray tandem mass spectrometry (LC-MS/MS).

FIG. 9A-E: Paint molecules selected for their low dissociation rate and the capability to remain bound to protein after denaturation, reduction and alkylation. (FIG. 9A) Chemical properties of the paint molecules, including chemical name, molecular weight, dissociation rate, capability to remain bound to protein after reduction and alkylation, solubility in water for selected paint molecules. Selection criteria for paint molecules include: $k_{off}<6*10^{-5}$ $s^{-1}$, water soluble=yes, survives to reduction and alkylation=yes. These dyes have not been previously explored for protein binding kinetics and protein cleavage site blockage. (FIG. 9B-E) Molecular formula and absorbance spectrum for sodium 4-(4-(benzyl-et-amino)-ph-azo)-2,5-di-cl-benzenesulfonate; 10-dioxo-4-[3-(2-sulfonatooxyethylsulfonyl)anilino]anthracene-2-sulfonate; Phenyl 4-[(1-amino-4-hydroxy-9,10-dioxo-9,10-dihydro-2-anthracenyl) oxy]benzenesulfonate; and disodium; 4-amino-3-[[4-[4-[(1-amino-4-sulfonatonaphthalen-2-yl)diazenyl] phenyl] phenyl]diazenyl]naphthalene-1-sulfonate, respectively. The characteristic peak absorbance wavelengths determined above were employed for the measurement of binding kinetics shown in FIG. 1.

FIG. 10A-C: Small molecule molecular "paints" screened for use in protein painting methodology. Class, CAS number, name and molecular formula are shown. All molecular paints were purchased from Sigma except compounds CAS 514-73-8 and 8004-87-3 which were purchased from Fisher and CAS 2580-78-1 which was purchased from Acros Organics. Binding mechanisms involve hydrophobic and electrostatic forces. Small molecular "paints" may preferentially recognize charged amino acids[2] predominantly found on the surface of proteins and are essential to trypsin cleavage sites. Small molecular "paints" can insert aromatic rings into non-polar hydrophobic pockets of the protein surface, while the flanking portions of the dye and protein molecules can re-arrange depending on energy constraints. A variety of chemical classes (first column) were ranked for utility as molecular paints based on the following criteria using the workflow described in FIG. 8: a) extremely rapid on-rates ($M^{-1}$ $sec^{-1}$) and very slow off-rates ($sec^{-1}$), b) remain bound following protein dissociation or denaturation with 2 M urea, and c) bind to multiple sites on the exposed protein surface to achieve full coverage of all the trypsin cleavage sites.

FIG. 11: Selected molecular paints block all trypsin cleavage sites of carbonic anhydrase II. Amino acids (bottom sequence, larger size fonts) are consensus trypsin cleavage sites of carbonic anhydrase II that were identified by reverse-phase liquid chromatography nanospray tandem mass spectrometry in the absence of molecular paint (Unpainted). Trypsin cleaves the peptide bond on the carboxyl side the amino acids arginine and lysine. Molecular paints blocked all (100%) consensus trypsin cleavage sites (painted, indicated by a blue "X"). Carbonic anhydrase was chosen because it contains 80% of the trypsin cleavage consensus sites that represent all the variations of the amino acids at the carboxy-side of the arginine and lysine. To further confirm that all the possible trypsin cleavage consensus domains were conserved as binding sites for the molecular paints, we conducted similar experiments for aprotinin and albumin in addition to the IL1β-IL1RI-IL1RAcP complex which documented full coverage of all known trypsin cleavage consensus sites for any permissible amino acid.

FIG. 12A-J: Mass spectrometry identified trypsin cleavage sites within interface domains of the painted native IL1b-IL1RI complex. (FIG. 12A) Interfacing residues predicted by crystal structure (PDBePISA software[3] on PDB entry 1ITB) in the IL1β-IL1RI complex are shown (shaded residues). Resolution of our protein painting method is determined by the nearest trypsin cleavage site at or near the contact point/close interface, where there is solvent exclusion, hydrogen bonds and salt bridges. Trypsin cleavage sites (R or K) revealed by protein painting followed by mass spectrometry are labeled and compared to the crystal structure predicted interfaces. All the consensus trypsin cleavage sites that were within 9 amino acids of a contact point predicted by crystal structure were correctly identified by protein painting and mass spectrometry analysis (Fisher exact test p-value=0.0003, odds ratio=13.49206). It's important to note that an MS peptide revealed by protein painting constitutes a true positive independent of the MS protein coverage. (FIG. 12B-J) Peptides identified with mass spectrometry relative to the interface domains of IL1β-IL1RI complex.

FIG. 13A-D: Arg286 peptide mass spectrometry sequence and 3D model. (FIG. 13A) IL1RAcP peptide identified by protein painting followed by mass spectrometry relative to the closest proximity hot spot in the IL1β-IL1RI-IL1RAcP complex. Protein painting revealed this single domain as an interaction point incorporating an arginine at the outermost bend of the beta loop and was predicted to participate both in hydrogen bonding and salt bridge formation between the accessory protein and the receptor-ligand complex. This peptide was used to generate Arg 286 peptide inhibitor and was also used as the antigen for Arg286 pep monoclonal antibody production (FIG. 2). (FIG. 13B) Arg 286 peptide is represented as a ribbon structure in the context of the ternary complex. Arg286 amino acid is represented by solid spheres. IL1RAcP is depicted on the left backbone. (FIG. 13C) Hydrogen bonds and salt bridges predicted by crystal structure analysis (PDBePISA) of the IL1RAcP and IL1β complex (PDB entry 4EDP). Residues listed under Structure 1 and Structure 2 are predicted by crystal structure. The results from protein painting for the same domain are shown in the right hand column. Six out of 7 interactions predicted by crystallography were correctly found by protein painting. (FIG. 13D) Hydrogen bonds and salt bridges predicted by crystal structure analysis (PDBePISA) of the IL1RAcP and IL1RI complex. Residues listed under Structure 1 and Structure 2 are predicted by crystal structure. The results from protein painting for the same domain are shown in the right hand column. 5 out of 5 interactions predicted by crystallography were correctly found by protein painting.

FIG. 14: Arg286 peptide sequence conserved in evolution. Sequence of Arg286 peptide found by protein painting is compared among species. Identical residues are shown. This peptide sequence is conserved in evolution reflecting its important functional role. The numbers flanking the sequences are those provided by BLASTp software.

(FIG. 15A) Paint molecules coat the surface of native protein complexes but cannot gain access to solvent-inaccessible protein-protein interface domains. Interleukin Receptor-ligand complex depicted with bound paint molecules to scale. Insert, each molecular paint spans less than 3 amino acids. (FIG. 15B) Trypsin cleavage is blocked by presence of paint molecules which bind non-covalently near trypsin consensus sequences. Following dissociation of painted proteins the area of interaction remains unpainted and is susceptible to trypsin cleavage. (FIG. 15C-E) association (main plot) and dissociation (insert) binding curves (moles of paint per mole of protein) for paint molecules shown in the insert associating with carbonic anhydrase II. Saturation is reached within five minutes and the off rate is less than 10% dissociation after 2 hours. Data points are obtained by measuring the absorbance at the characteristic wavelength of the each molecular paint (FIG. 9). (FIG. 15F) Compared to native condition (insert, column 1), paint molecules remain bound to the protein in the presence of 2 M urea denaturation (black, main plot), DTT reduction (insert, column 2) and iodoacetamide alkylation (insert, column 3), prior to trypsinization.

FIG. 16A-F: Protein painting reveals hidden residues within hot spots of interaction between IL1β, IL1RI and IL1RAcP. (FIG. 16A) Identified opposing contact points revealed by the method for the ligand bound to its receptor (Fisher exact test p-value<0.0003). (FIG. 16B) IL1RAcP bound to the receptor ligand complex. Sequences identified for each protein were found to be opposing and juxtaposed, as noted. The sequence labeled Arg286 (represented in black in the protein model) was used to generate a synthetic peptide antagonist and was used as an antigen for a mouse IgG monoclonal antibody to Arg286 peptide. (FIG. 16C) Protein painting correctly revealed key contact points with closest proximity predicted by X-ray crystallography and PDBePISA structural analysis software (PDB entry 4DEP). (FIG. 16D) Synthetic antagonist peptide Arg286 inhibited SAPK/JNK signaling downstream from IL1RI as effectively as IL1RAcP (IL1 β concentration: 10 ng/mL, IL1RAcP concentration: 1 μg/mL, Arg286 peptide concentrations: 3.3, 16.7 and 33 μM). In lane 8, scrambled peptide obtained by randomly shuffling Arg286 sequence (33 μM) does not inhibit the signaling downstream from IL1RI. Data are representative of three independent experiments. (FIG. 16E) Arg286 peptide inhibition of ligand pull-down within the receptor complex by His-tagged IL1RAcP. Schematic representation of the complex is depicted in insert (IL1β, IL1RI and IL1RAcP concentrations: 0.44 μg/mL, 2 μg/mL and 0.72 μg/mL respectively; Arg286 peptide concentrations: 6.7, 3.3, 1.7, 0.8 and 0.4 μM). IL1RAcP in absence of IL1RI does not pull down IL1β, lane 8. (FIG. 16F) Arg286 peptide mAb specific for IL1RAcP peptide extinguishes complex formation (Arg286 peptide mAb concentration 0.4 mg/mL) depicted in insert.

(FIG. 17A) Trypsin binding sites that are blocked by MV lay on the surface of the folded native molecule but do not bind to trypsin cleavage sites on the inner folded domain of the protein. Trypsin sites blocked by MV are rendered in 30 solid representation. (FIG. 17B) MV binding to trypsin sites is confirmed by molecular docking. Example of molecular docking (SwissDock, worldwideweb.swissdock.vital-it.ch/docking) of MV and IL1R1. MV is predicted to bind to a cavity containing Lys161 trypsin binding site.

(FIG. 18A) Binding sites of DECI lay on the surface of the folded molecule as rendered in 3D solid representation. (FIG. 18B) DECI binding to trypsin sites is confirmed by molecular docking. Example of molecular docking (SwissDock, worlwideweb.swissdock.vital-it.ch/docking) of DECI and IL1R1. DECI is predicted to bind to a cavity containing Lys114 trypsin binding site.

(FIG. 19A) Trypsin binding sites that are blocked by ANSA lay on the surface of the molecule. Trypsin sites blocked by ANSA are rendered in 30 solid representation. (FIG. 19B) ANSA binding to trypsin sites is confirmed by molecular docking. Example of molecular docking (SwissDock, worldwideweb.swissdock.vital-it.ch/docking) of ANSA and IL1R1. ANSA is predicted to bind to a cavity containing Lys70 trypsin binding site.

DETAILED DESCRIPTION

Figure 1:
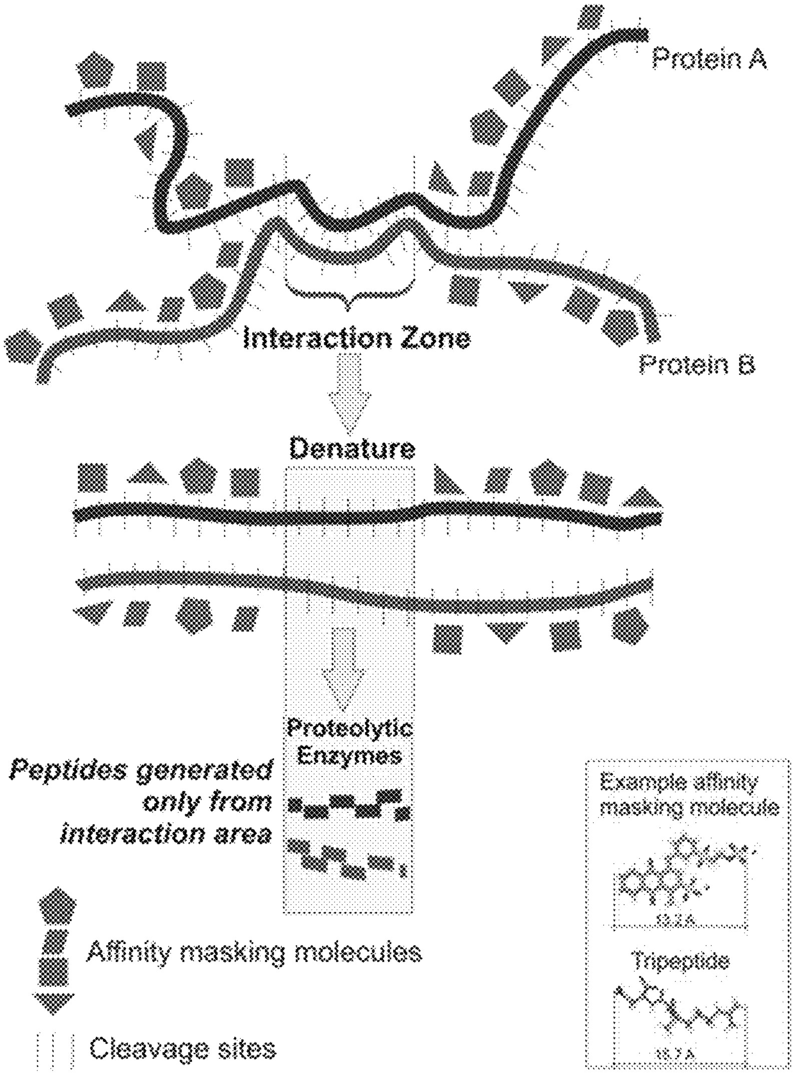
FIG. 1: Masking proteins with small organic molecule pigments to identify binding interactions. Low molecular weight organic masking molecules bind protein polypeptides with high affinity and span a small region comprising approximately 3 amino acids. Once bound to the protein surface, they block the trypsin cleavage site at the domain that is masked by the organic molecule.
Figure 3:
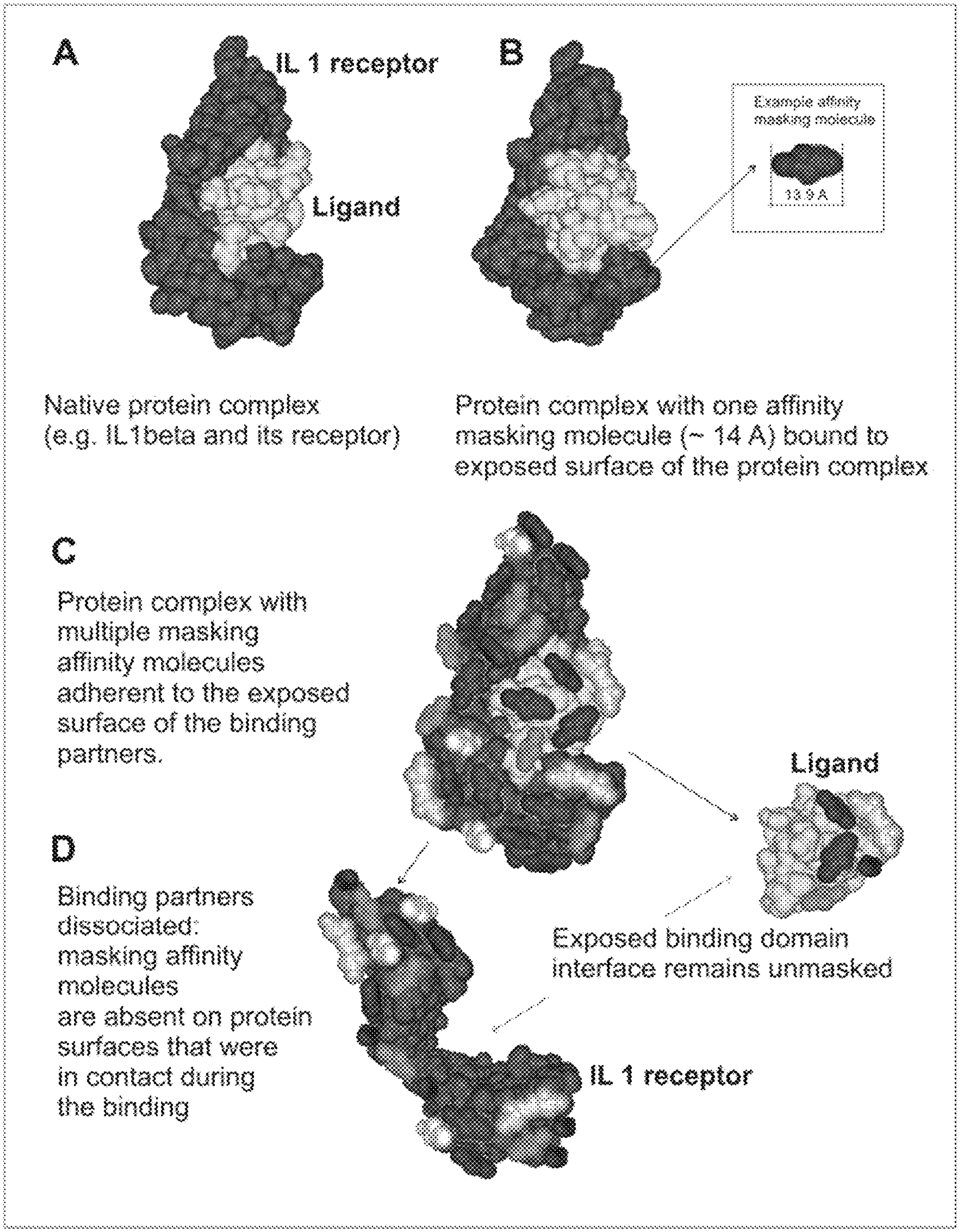
FIG. 3: Illustrative model showing that one or more small masking molecules coat the surface of interacting proteins only on surfaces that are not in contact.

The present disclosure provides specialized chemistry and methodology for determining binding sites between proteins, proteins and nucleic acids, or proteins and small molecules. Applicants discovered that when mixing a mixture of affinity masking small organic molecules with a native protein complex, the masking molecules bind with high affinity to all sites on the protein not covered by the interaction domains. Following masking, the associated proteins, for example, are dissociated leaving the masking molecules coating all areas of the protein amino acid sequence that were not participating in the interaction interface. Thus the dissociated proteins will have their interaction zone exposed while all the other protein domains will be coated or masked. The interaction zone, thus identified and exposed, can then be studied.

Harnessing Applicants' technology, for example, the masked protein can be MS sequenced in a manner that will directly and specifically generate the sequence of the interacting zone. Additionally, the masked protein can be used in a ligand (e.g. antibody) binding assay in which the ligand binding will only take place if the interaction zone is unmasked.

As described below, Applicants employ small organic molecule masking pigments that bind to the surface of proteins, for example, and can be used to "paint" the exposed regions of a protein in solution. In so doing, Applicants provide compositions and methodology for the rapid and direct positive identification and sequencing of the contact interface region between two interacting native unmodified proteins, for instance.

The instant composition and methodology provide a means for directly identifying protein-ligand structure and sequence in living cells, in cell lysates, and in protein solutions/mixtures. In the past these binding domains could only be determined indirectly by expensive and time consuming xray crystallography, site directed mutagenesis, or artificially adding genetic tags. The present technology employs native proteins interacting naturally without any need to genetically modify, tag or perturb the protein binding partners. No other existing technology is similar and no other technology can directly read-out the amino acid sequence of the protein binding domains. The instant methodology and compositions can also elucidate protein folding, a holy grail for biotechnology. Misfolded proteins are the cause of cardiovascular, neoplastic, neurologic, and immune diseases.

Of course, and as exemplified below, the instant compositions and methodologies find use in a variety of applications, including but not limited to individual pairs of proteins or it can be used in one step to globally sequence or identify all the simultaneous protein-protein interaction regions (the interactome) in a population of proteins: for example an organelle, cell, or tissue lysate. The disclosure can be used to characterize the step-wise folding of an individual protein at the amino acid level, or to map the sequence of binding events over time. The technology can also be used to discover or evaluate drugs that block protein-protein interactions. Likewise, the disclosure can be used to map antibody-antigen binding domains for antibody-based therapy, vaccine development, and infectious disease research. Similarly, the disclosure can be used to directly generate or screen ligands (including drugs or nucleic acids) or antibodies that are specific for the interaction face region of a protein.

As explained below, the instant methodology will provide a positive signal only if two native proteins, for example, are interacting. As used herein, "interacting" means two proteins, for example, are in contact at least at one point in the protein amino acid chain of each protein in the pair. The same principle applies to protein contact regions for protein-DNA interactions or any other protein-ligand interaction.

In one application, and as described below, protein painting was used to study the multiple hot spots participating in the three-way interaction of IL1b ligand, its receptor IL1R1, and the accessory protein IL1RAcP. Interleukin signaling requires the interaction of all three proteins. Aberrant function of this complex is involved in a variety of diseases, including cancer, rheumatoid arthritis, systemic lupus erythematosus, inflammatory bowel disease, systemic vasculitis, neonatal bronchial dysplasia, and inflammatory bone and cartilage destruction. The instant protein painting revealed a previously unknown 3-way hot spot between the accessory protein, the ligand, and the receptor. This novel information was used to create synthetic beta loop peptides corresponding to the three-way hot spot at the accessory protein. The peptide mimicking the interface blocked ILlbeta signaling in ligand stimulated cells and could substitute for the entire truncated accessory protein as a competitive inhibitor. This same hot spot peptide mimic, and a monoclonal antibody raised against this sequence, blocked the three way complex formation between the IR1, IL1beta and the accessory protein. Both the peptide and the monoclonal antibody provide new therapies for treating diseases caused by aberrant interleukin signaling.

A. Masking Proteins with Small Organic Molecule Pigments

As described below, Applicants employ small organic molecule masking pigments that bind to the surface of proteins, for example, and can be used to "paint" the exposed regions of a protein in solution. Low molecular weight organic masking molecules bind protein polypeptides with high affinity and slow off-rates, and span a small region comprising approximately 3 amino acids. Once bound to the protein surface, they block the trypsin (or other protease) cleavage site at the domain that is masked by the organic molecule.

The technology can be applied to binary protein interactions or large multi-protein complexes including transcription, euchromatin or heterochromatin complexes. A positive signal occurs only if a ligand-protein or protein-protein interaction (native unmodified proteins) has taken place and can thereby be of general utility in diagnostics, therapeutics, and medical research.

While in no way limiting, exemplary small organic molecule pigments include an aryl hydrocarbon containing organic compound less than 30 Angstroms in total length taken from at least one of the following structure formulas listed below, or salts or solvates thereof, complexed or bound to a portion of a protein polypeptide chain of at least 3 amino acids where the amino acid in position 1 (P1) from the amino terminus is any amino acid, position 2 (P2) is K or R and the amino acid in position 3 (P3) is not P, (I)

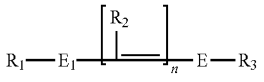

Q

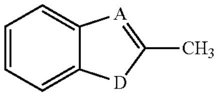

Q'

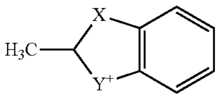

Polymethine compounds

[wherein R1 represents H, O, halo, CO2H, NO2, SH, NR5R6, C1-6 alkyl, C1-6 alkoxy, cyano, carbonyl, pyrrolidinyl, pyrrolyl, pyrazolyl, imidazolyl, triazolyl, etc.;

R5, R6 represent H, C1-4 alkyl;

E1 represents benzene ring or ring Q

A represents CH or N;

D represents S, NH, N—C1-3 alkyl, O, or CH2;

R2 represents H, C1-4 alkyl, halo-C1-4 alkyl, HO, cyano;

n represents an integer of 1-4;

E=benzene ring or ring Q'

X represents CH or N

Y represents S, NH, N—C1-3 alkyl, O, or CH2

R3=H, O, halo, CO2H, NO2, SH, NR5R6, C1-6 alkyl, C1-6 alkoxy, cyano, carbonyl, pyrrolidinyl, pyrrolyl, pyrazolyl, imidazolyl, triazolyl, etc.)

(II)

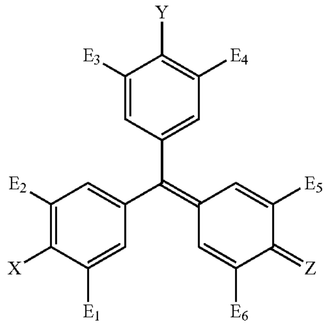

Triarylmethane compounds

[wherein X, Y, Z represent H, NR1R2, sulfa, O, halo, CO2H, NO2, SH, C1-6 alkyl, C1-6 alkoxy, etc.;

R1, R2 represent H, C1-6 alkyl, sulfophenyl;

E1, E2, E3, E4, E5, E6 represent H, sulfa, C1-6 alkyl, halo, CO2H, NO2, SH;]

(III)

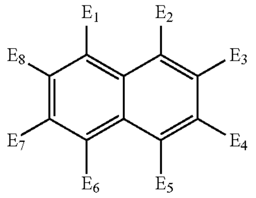

Naphthalene derivatives

[wherein E1, E2, E3, E4, E5, E6 represent H, O, C1-6 alkyl, C1-6 alkoxy, carbonyl, sulfo, NO2, NR1R2, azetidinyl, thiazolidinyl R1, R2 represent H, phenyl]

(IV)

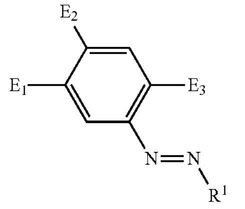

Q

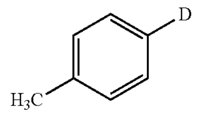

Q'

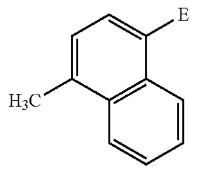

Arylazo compounds

[wherein E1, E2, E3 represent H, halo, sulfo, O, C1-6 alkyl, C1-6 alkyl aryl;

R1 represents ring Q or ring Q';

D represents H, NR2R3;

R2, R3 represent C1-6 alkyl, C1-6 alkyl aryl;

E represents H, O, OH, C1-6 alkyloxy]

(V)

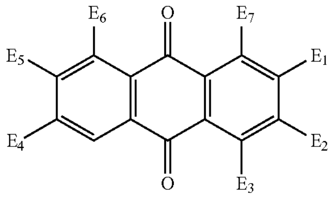

Q

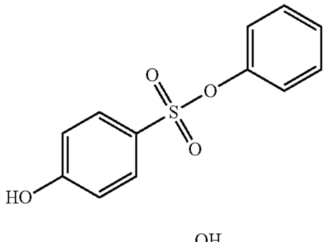

Q'

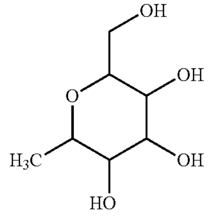

-continued

Q''

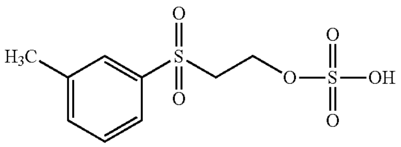

Anthraquinones

[wherein E1 represents H, NH, sulfo, Q, Q', C1-6 alkyl, OH, carboxy;

E2 represents H, NH, OH, C1-6 alkyl, sulfo;

E3 represents H, NH, OH, NR1R2, sulfo, C1-6 alkyl;

R1, R2 represent H, Q'';

E4, E5, E6, E7 represent H, OH, NH, sulfa, C1-6 alkyl, carboxy]

(VI)

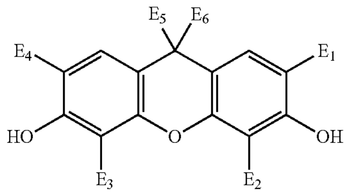

Q

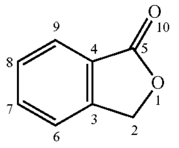

Xanthenes

[wherein E1, E2, E3, E4 represent H, NO2, OH, Halo, C1-6 alkyl;

E5, E6 represent H or Carbon in position 3 and oxygen in position 1 in group (VII)

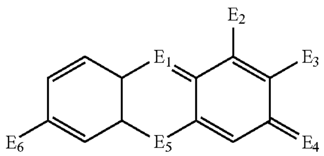

Thiazine

[wherein E1 represents N, O, S;

E2, E3 represent H, C in aryl;

E4 represents O, N, NR1R2;

R1, R2 represent C1-6 alkyl;

E5 represents N, O, S;

E6 represents H, NH, NC1-6 alkyl]

FIG. 2 provides affinity masking molecule examples, including but not limited to Alizarin Blue Black B (ABB), Disperse Blue 3 (DB3), Remazol Brilliant Blue R (RBB), Pigment Red 177 (PR1), Acid Black 48 (AB4), Disperse Yellow 3 (DB3), Acid Black 1 (AB1), Disperse Orange 3 (DO3), Disperse Yellow 9 (DY9), Rhodamine 123 (R12), Toluidine Blue O (TBO), Pararosaniline Base (PR), Brilliant Blue R-250 (BB), Acid Blue 22 (AB2), Cibacron Blue F3GA (CB), Acrylic Acid (AAc), and Vinyl Sulfonic Acid (VSA).

Table 1 below provides suitable small organic compounds useful for blocking protease sites.
TABLE 1
| Small organic compounds used for blocking protease sites. | |
|---|---|
| Pinacyanol chloride | 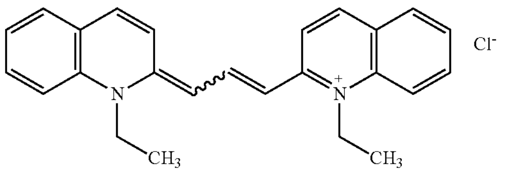 |
| 1,1'-Diethyl-4,4'-cyanine iodide | 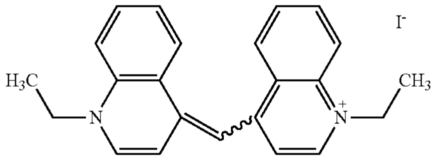 |
| Fluorescein | 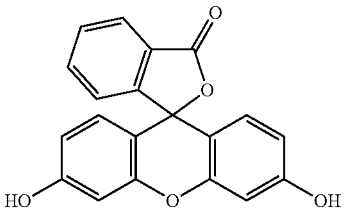 [SMILES: O=C1OC2(c3ccc(O)cc3Oc3cc(O)ccc32)c2ccccc21] |
| 3,3'-Diethylthiadicarbocyanine iodide | 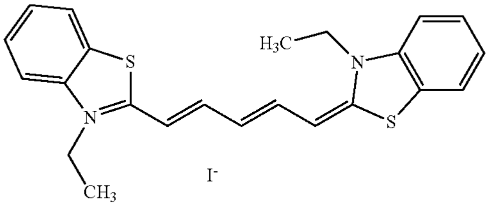 |
| Nile Red | 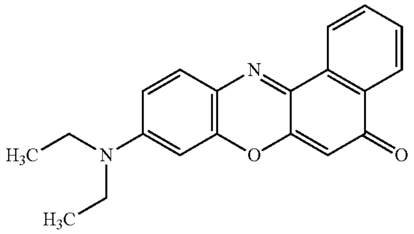 [SMILES: CCN(CC)c1ccc2nc3c4ccccc4c(=O)cc-3oc2c1] |
| Thioflavin T | 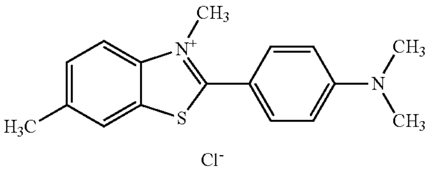 |
| 8-Anilino-1-naphthalenesulfonic acid | 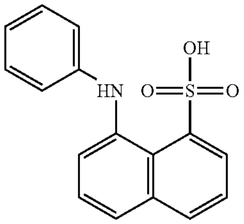 [SMILES: O=S(=O)(O)c1cccc2cccc(Nc3ccccc3)c12] |

TABLE 1-continued
| Small organic compounds used for blocking protease sites. | |
|---|---|
| 4,4'-Dianilino-1,1'-binaphthyl-5,5'-disulfonic acid dipotassium salt | 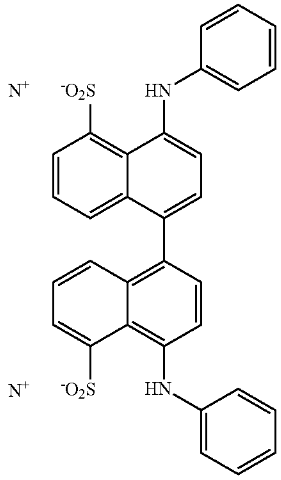 |
| Orange G | 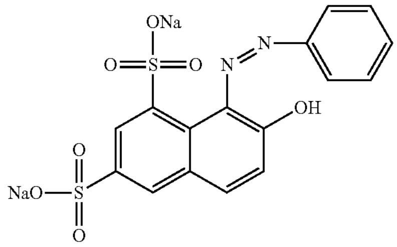 |
| sodium 4-[(4-methoxy-1-naphthyl)diazenyl]benzenesulfonate | 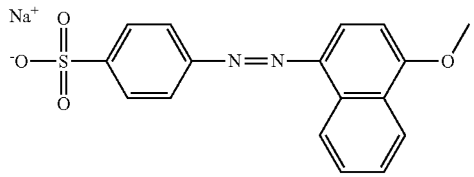 |
| Phenyl 4-[(1-amino-4-hydroxy-9,10-dioxo-9,10-dihydro-2-anthracenyl)oxy]benzenesulfonate | 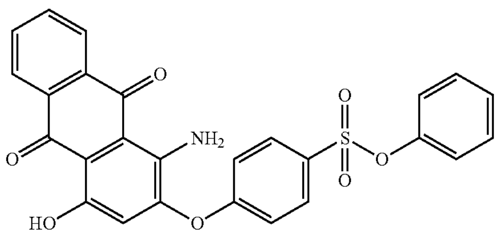 [SMILES: Nc1c(Oc2ccc(S(=O)(=O)Oc3ccccc3)cc2)cc(O)c2c1C(=O)c1ccccc1C2=O] |
| Sodium 4-(4-(benzyl-et-amino)-ph-azo)-2,5-di-cl-benzenesulfonate | 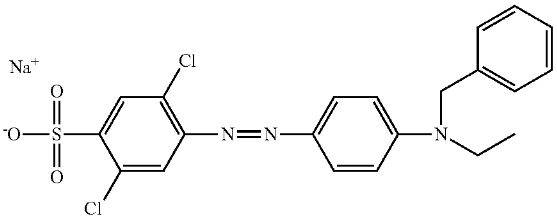 |

TABLE 1-continued
| Small organic compounds used for blocking protease sites. | |
|---|---|
| Ethyl Orange sodium salt | 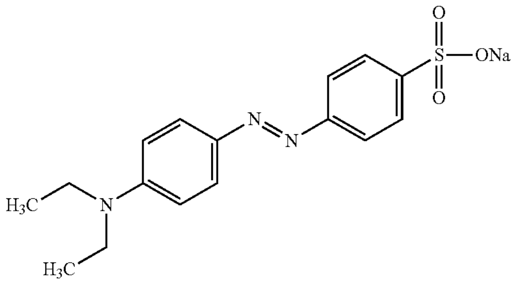 |
| Orange II sodium salt | 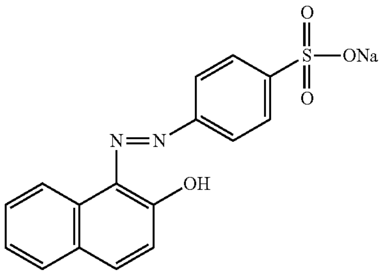 |
| Crocein MOO | 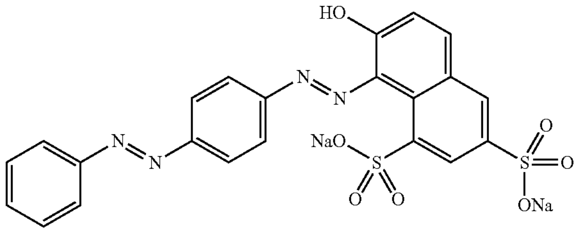 |
| Copper phthalocyanine tetrasulfonic acid tetrasodium salt | 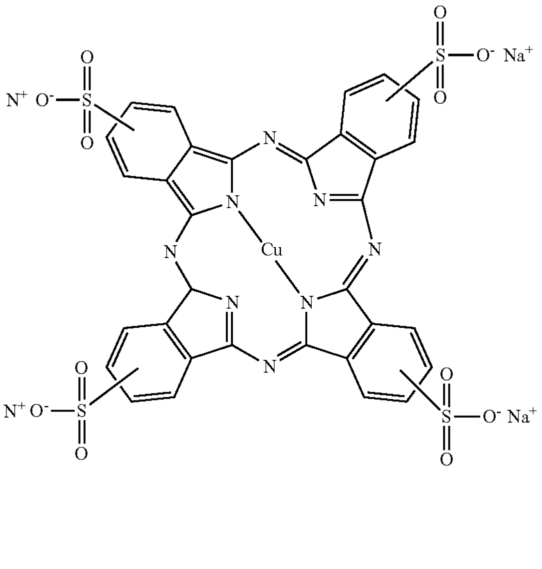 |
| Xanthene | 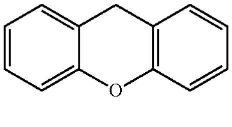 [SMILES: c1ccc2c(c1)Cc1ccccc1O2] |

TABLE 1-continued
| Small organic compounds used for blocking protease sites. | |
|---|---|
| Eosin B | 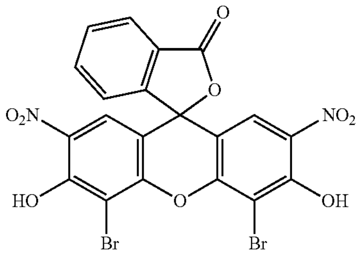 [SMILES: O=C1OC2(c3ccccc31)c1cc([N+](=O)[O-])c(O)c(Br)c1Oc1c2cc([N+](=O)[O-])c(O)c1Br] |
| Eosin Y | 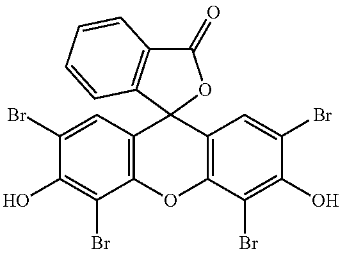 [SMILES: O=C1OC2(c3ccccc31)c1cc(Br)c(O)c(Br)c1Oc1c2cc(Br)c(O)c1Br] |
| Congo Red | 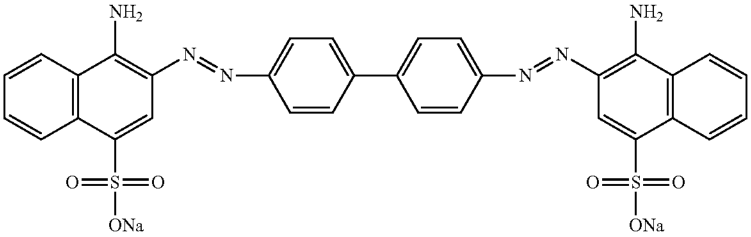 |
| Methyl Blue | 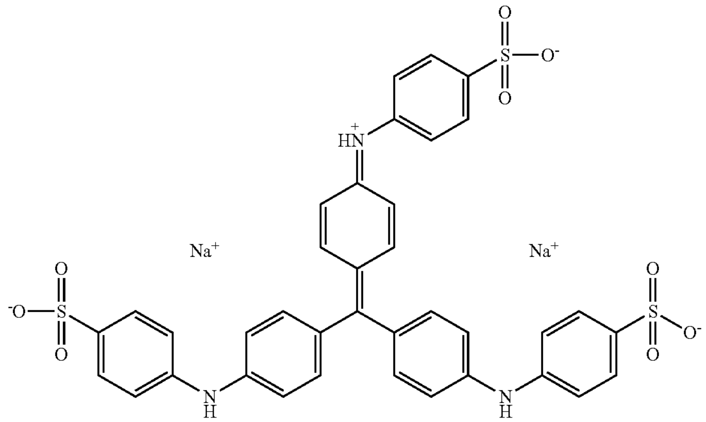 |
| Acid Fuchsin | 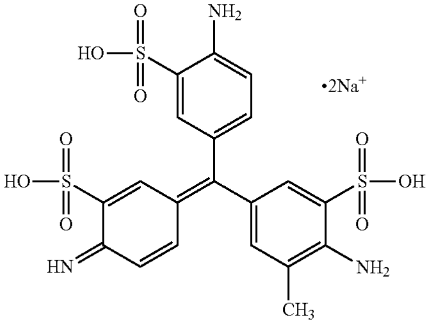 [SMILES: Cc1cc(/C(=C2\C=CC(=N)C(S(=O)(=O)O)=C2)c2ccc(N)c(S(=O)(=O)O)c2)cc(S(=O)(=O)O)c1N] |

TABLE 1-continued

| Small organic compounds used for blocking protease sites. | |
|---|---|
| Methyl violet | 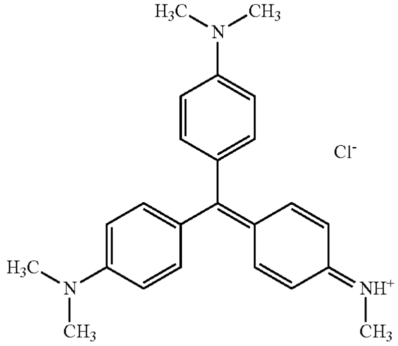 |
| Aniline Blue diammonium salt | 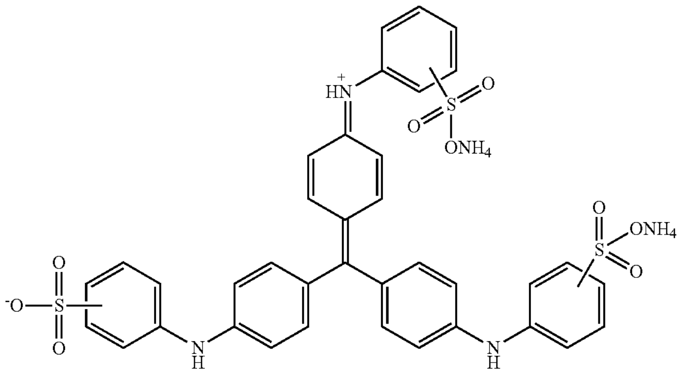 |
| Azure A chloride | 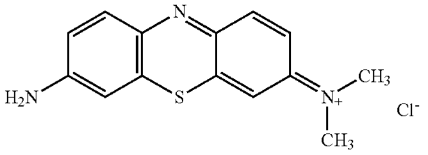 |
| Carmine | 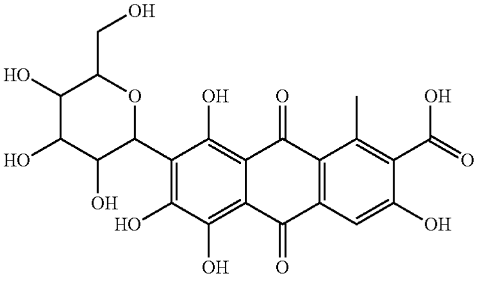 [SMILES: Cc1c(C(=O)O)c(O)cc2c1C(=O)c1c(O)c(C3OC(CO)C(O)C(O)C3O)c(O)c(O)c1C2=O] |
| Remazol Brilliant Blue R | 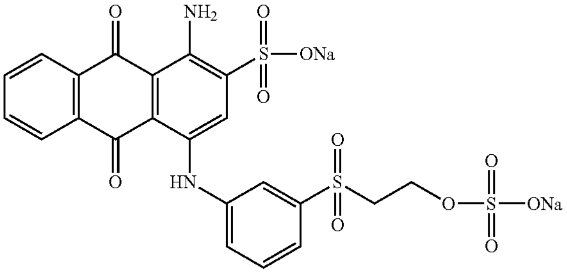 |

While FIG. 2 provides exemplary masking molecules, suitable masking pigments must be small enough in size so that the masking of the exposed surface of the individual protein molecule can be accomplished with adequate resolution. After screening large numbers of binding molecules the pigment masks shown in FIG. 2 are an example of the types of molecules that can bind (with very high affinity) and mask proteins with a resolution of approximately 3 amino acids. This provides sufficient resolution to effectively mask surface domains even over complex 3-D shape curvatures and can potentially achieve a masking density to cover all (trypsin or other protease) cleavage sites in any given protein.

Applicants established that these masking molecules will bind to proteins with very high affinity with a very low dissociation constant ($k<1^{-10}$) and a very slow off rate. This insures that the protein painting is stable and can remain adherent following partial or complete linearization of the protein polypeptide chain. Applicants demonstrate that the masking molecules will remain adherent to the protein molecule after exposure to levels of denaturant or detergent treatments that can dissociate protein-protein binding partners. Once the masking molecules are bound to the protein in solution, and the unbound masking molecules are washed away, the bound masking molecules prevent trypsin cleavage at a location at or near the masking pigment binding site.

The masking pigments bind to regions of the protein surface using different mechanisms. Some prefer hydrophobic sites while other prefer hydrophilic or anionic or cationic regions. Applicants determined that the binding affinity and protein binding region specificity is a function of the side chain composition of the ring substitutions and the primary structure of the molecule. Applicants discovered that one class of pigment mask molecule will bind to the protein molecule at multiple, but limited, number of specific sites. Adding additional classes of pigment mask molecule, which recognize different classes of protein domain, can fill in the gaps such that a proper mixture of molecules will attain full coverage of all the exposed regions of the protein or block all the protease cleavage sites or all the ligand binding sites. For interleukin B receptor and its ligand, the applicants have found that at least three classes of masking molecules can attain virtually full coverage (See Experimental Example 2).

Consequently, in one embodiment, two or more masking molecules with a resolution covering less than 5 contiguous amino acids are selected for the masking of a protein surface. The masking molecules are applied in solution to the solution phase native protein when it is bound to its binding partner.

In one embodiment, a set of masking molecules is selected from a reference list or panel. The set or mixture of masking pigments can be optimally chosen prior to use depending on the known primary and secondary structure of the protein candidates to be analyzed.

In a second embodiment, a set of pigments or masks that are known to prefer phosphorylated amino acids, or other post-translationally modified (PTM) amino acids are selected. Proteins and/or peptides or combinations of proteins/peptides with other molecules such as nucleic acids, can be screened for structures that bind phosphorylated or other post translationally modified regions. The presence of phosphorylation sites or other PTM in the binding interaction can be identified.

In a further embodiment a mixture of a large variety of masking proteins is used to cover the exposed surfaces of diverse proteins in a complex mixture such as a cell lysate, or a cell suspension.

In a further embodiment, bioinformatic analysis can automatically reconstruct the amino acid sequence of the binding domain based on the following parameters: a. the selected panel of masking pigments, b. the known amino acid structure of the proteins being studied, and c. the difference in ms peptides generated before and after the binding reaction.

In a further embodiment, provided herein is a diagnostic kit for determining whether one or more protein-ligand (ligand includes drug, or non-protein molecule such as a nucleic acid or carbohydrate) binding events has occurred in a mixture of at least 1 protein and 1 ligand.

In a further embodiment of the invention, the proteins or the masking pigments can be pre treated or co-incubated with substances that will enhance the binding affinity or specificity by reacting with the protein or with the masking pigment.

In a further embodiment the affinity masking pigments can be administered to the protein-protein or protein-ligand complex in an automated fashion using appropriate fluidics and molecular size exclusion chromatography, or other means, to rapidly separate the free unbound masking molecules from the proteins with the bound pigments. The quantity of bound or free masking pigments can be monitored by taking advantage of the light absorbance or transmission spectrum of the particular masking molecule.

B. Direct Sequencing of Interacting Domains.

The interaction zone exposed following masking (painting) and protein dissociation is digested with proteolytic enzymes and sequenced by mass spectrometry (MS) (FIG. 1). The masking molecules remain on the two proteins after they are dissociated and linearized. Proteolytic enzymes such as trypsin will not cleave the regions of the protein that are masked or "painted". The proteolytic enzymes will only cleave the protein domains that participated in the protein-protein interaction zone and are not blocked by the masking molecules. Following proteolysis, therefore, proteolytic peptides will only be generated from the interacting zone. The cleaved peptides are sequenced by mass spectrometry. The derived mass spectrometry sequence will comprise only the region of interaction, since the peptides will be cleaved only from the regions of the proteins that are touching each other and therefore protected from exposure or interaction with the affinity masking molecules. (FIG. 1). In another iteration, the mask can be applied individually to each of two native proteins and then after they interact. The difference between the sequences revealed before and after the proteins bind will reveal the binding site.

This method can be applied to one binary set of interacting proteins or it can be applied to a large population of native proteins containing a subset of interacting proteins. If applied to a cell protein lysate the output will be the amino acid sequences from only the subset of protein domains that were participating in the protein-protein interactions at the time the masking molecules are introduced. If the method is applied to a single folded native protein, or a protein during various stages of folding, the output can be the regions of the protein masked during the folding process. If the method was used over time following cell stimulation with a ligand, or treatment with an inhibitor, all sets of protein interaction zones that change following this perturbation could be directly and specifically sequenced.

C. Ligand Detection of Interaction Events

After the masking or painting step described above, followed by dissociation of the binding partners, a ligand (e.g., antibody, a protein, or a non-protein molecule) will only recognize the exposed unpainted domain if it has been previously occupied by a binding partner. Thus the ligand will only detect interaction events. Consider an antibody, drug, peptide, aptamer, or other ligand that is specific for the interaction domain interface of two proteins. This ligand can be applied to a cell lysate (or a living cell) after the native interacting proteins have been masked (painted) and then dissociated. A positive binding event will only occur if the lysate contains protein interaction events. If the masked and dissociated interacting protein is used as an antigen or immunogen or vaccine only the interaction binding domain will generate an antibody. The result will be the automatic generation of an antibody specific for the interaction domain.

D. Illustrative Applications

The instant technology finds use in a variety of applications. Drugs that block protein-protein interactions are the next frontier for pharmaceutical companies. Applicants provide a novel product for a) de novo discovering the protein binding domain targets for this new class of drugs, and b) finding and assaying drugs that block protein interactions. Protein-protein interaction studies, drug interaction studies, elucidation of protein folding, detection of protein-nucleic acid interactions, identification of protein misfolding sequences and the subsequent exposed binding sites, detection of heterochromatin and euchromatin in nucleic acids, miRNA binding, inhibition of protein-protein or protein-nucleic acid interactions, and production of antibodies to specific protein-ligand regions.

The instant technology can be used to characterize the step-wise folding of an individual protein at the amino acid level, or to map the sequence of binding events over time. It can also be used to discover or evaluate drugs that block protein-protein interactions. The methodology and compositions can be used to map antibody-antigen binding domains for antibody-based therapy, vaccine development, and infectious disease research. The disclosure can be used to directly generate or screen ligands (including drugs or nucleic acids) or antibodies that are specific for the interaction face region of a protein. The technology can be applied to study, characterize, or mark in vitro, or in vivo native protein interaction domains.

E. Exemplary Products

The instant technology finds use in a variety of applications and several products may derive. In one embodiment, provided is a diagnostic kit for determining whether one or more protein-ligand (ligand includes drug, or non-protein molecule such as a nucleic acid or carbohydrate) binding events has occurred in a mixture of at least 1 protein and 1 ligand. This diagnostic kit could be used in personalized medicine approaches for determining, in vitro prior to treatment, if the desired protein-drug interaction will occur in a given patient's sample.

In another embodiment, the present disclosure contemplates enhancing protein-ligand interaction specificity for in vitro assays and coupling reactions. The proteins or the masking dyes can be pre-treated or co-incubated with substances that will enhance the binding affinity or specificity by reacting with the protein or with the masking pigment.

Bioinformatic analysis can replace X-ray crystallography for determining protein structure. Bioinformatic analysis can automatically reconstruct the amino acid sequence of the binding domain based on the following parameters: a. the selected panel of masking pigments, b. the known amino acid structure of the proteins being studied, and c. the difference in mass spectrometry identified peptides generated before and after the binding reaction.

The instant disclosure contemplates producing novel antibodies with a specific affinity to the binding interaction. If the masked and dissociated interacting protein is used as an antigen, immunogen, or vaccine, only the interaction binding domain will generate an antibody. The result will be the automatic generation of an antibody specific for the interaction domain.

The present disclosure provides compositions and methodology for revealing binding sites between proteins, proteins and nucleic acids, or proteins and small molecules. The below examples are illustrative and non-limiting.

EXAMPLE 1

Small Organic Paint Molecules

Masking paint molecules must be small enough in size so that the masking of the exposed surface of the individual protein molecule can be accomplished with adequate high resolution. After screening a number of molecules derived from dye chemistry, paints shown in Table 2 are an example of the types of molecules that can bind (with very high affinity) and mask protein domains with a resolution of approximately 3 amino acids. This provides sufficient resolution to effectively mask surface domains even over complex 3-D shape curvatures and can potentially achieve a masking density to cover all (trypsin or other protease) cleavage sites in any given protein. The instant paint molecules are ten to one-hundred times smaller than affinity peptides described in the literature. Protein peptides, that bind larger proteins, can not be used for the present technology because of their large size, much lower resolution of coating, susceptibility to proteinases, and lower affinity.

TABLE 2

| Chemical structure and IUPAC nomenclature of the candidate protein painting molecules. |
|---|
| Xanthenes |
| 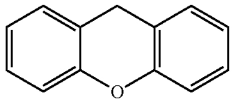<br>9H-xanthene |

TABLE 2-continued
| Chemical structure and IUPAC nomenclature of the candidate protein painting molecules. |
|---|
| 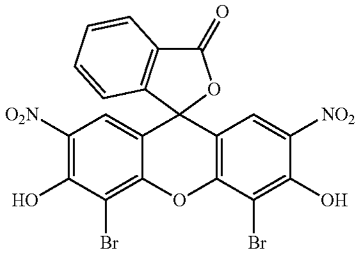<br>disodium 2-(4,5-dibromo-2,7-dinitro-3-oxido-6-oxoxanthen-9-yl)benzoate |
| 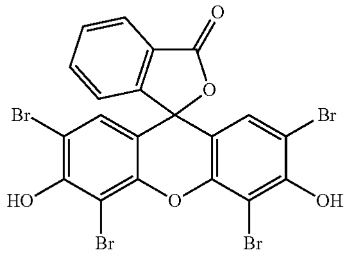<br>disodium 2-(2,4,5,7-tetrabromo-3-oxido-6-oxoxanthen-9-yl)benzoate |
| Triarylmethanes |
| 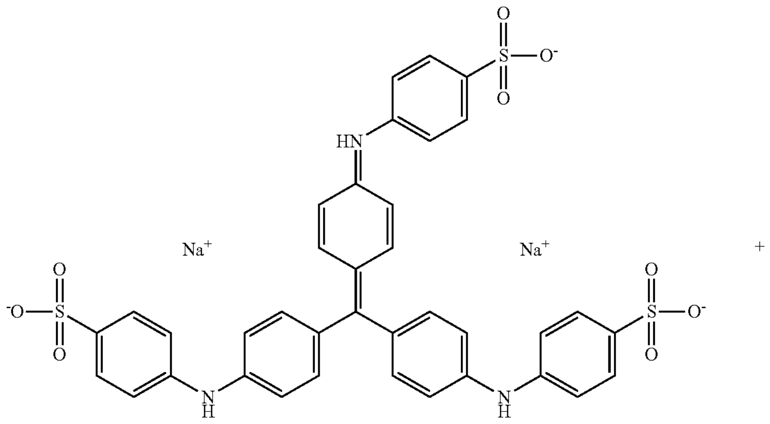<br>4-[4-[bis[4-(4-sulfoanilino)phenyl] methylidene]cyclohexa-2,5-dien-1-ylidene]azaniumylbenzenesulfonate |

TABLE 2-continued

Chemical structure and IUPAC nomenclature of the candidate protein painting molecules.

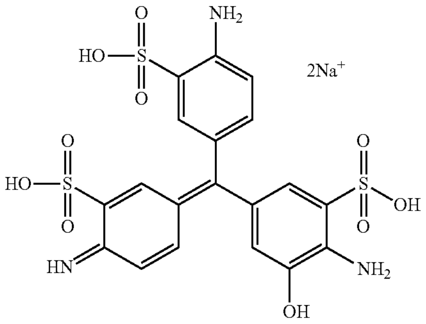

tetrasodium (3Z)-5-amino-3-[[4-[4-[(2Z)-2-(8-amino-1-oxo-3,6-disulfonatonaphthalen-2-ylidene)hydrazinyl]-3-methylphenyl]-2-methylphenyl]hydrazinylidene]-4-oxonaphthalene-2,7-disulfonate Azo compounds

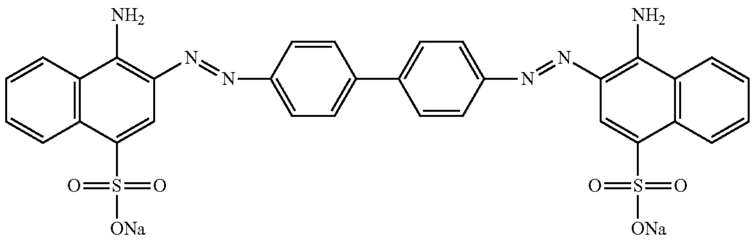

sodium 4-amino-3-[[4-[4-[(1-amino-4-sulfonatonaphthalen-2-yl)dianzenyl]phenyl] phenyl]diazenyl]naphthalene-1-sulfonate

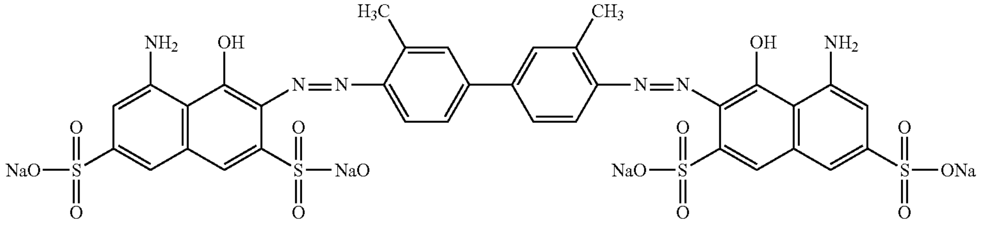

disodium (3Z)-3-[(4-amino-3-sulfonatophenyl)-(4-amino-3-sulfophenyl)methylidene]-6-imino-5-methylcyclohexa-1,4-diene-1-sulfonate Thiazines

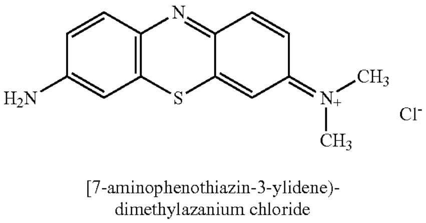 [SMILES: C[N+](C)=c1ccc2nc3ccc(N)cc3sc-2c1 ; [Cl-]]

[7-aminophenothiazin-3-ylidene)-dimethylazanium chloride

TABLE 2-continued

| Chemical structure and IUPAC nomenclature of the candidate protein painting molecules. |
|---|
| 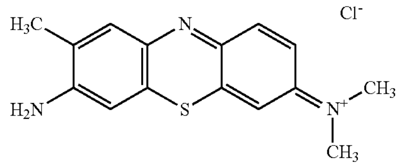 |
| [7-amino-8-methylphenothiazin-3-ylidene)-dimethylazanium chloride |
| 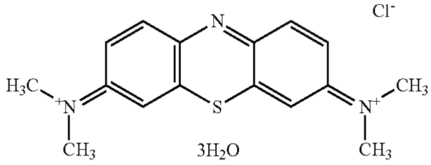 |
| [7-(dimethylamino)phenothiazin-3-ylidene]-dimethylazanium chloride |
| Anthraquinones |
| 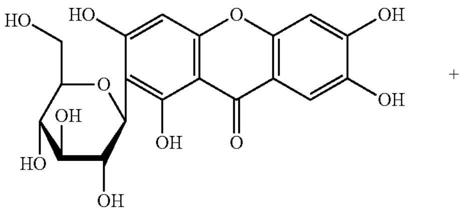 |
| 1,3,6,7-tetrahydroxy-2-[3,4,5-trihydroxy-6-(hydroxymethyl)oxan-2-yl]xanthen-9-one |
| 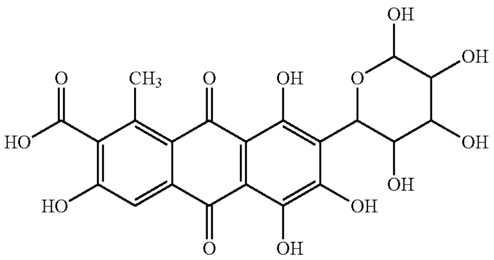 |
| 3,5,6,8-tetrahydroxy-1-methyl-9,10-dioxo-7-[3,4,5-trihydroxy-6-(hydroxymethyl)oxan-2-yl]anthracene-2-carboxylic acid |
| 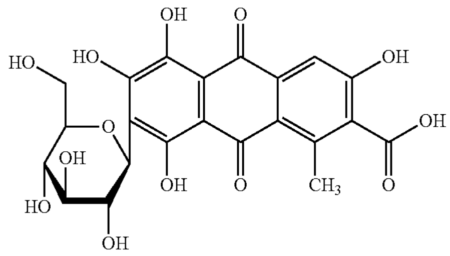 |
| 3,5,6,8-tetrahydroxy-1-methyl-9,10-dioxo-7-[(2R,3R,4R,5S,6R)-3,4,5-trihydroxy-6-(hydroxymethyl)oxan-2-yl]anthracene-2-carboxylic acid |

TABLE 2-continued

| Chemical structure and IUPAC nomenclature of the candidate protein painting molecules. |
|---|
| 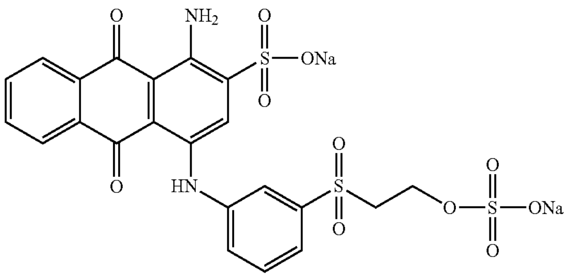 |
| 1-amino-9,10-dioxo-4-[3-(2-sulfooxyethylsulfonyl)anilo]anthracene-2-sulfonic acid |
| 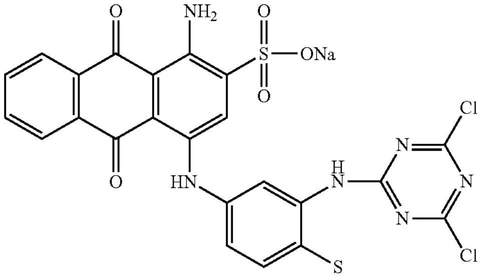 |
| 1-Amino-4-[3-(4,6-dichlorotriazin-2-ylamino 4-sulfophenylamino]anthraquinone-2-sulfonic acid |

High affinity binding and blockade of protease cleavage sites. Applicants identified classes of organic dye chemistries that bind with high affinity to the majority (if not all) the trypsin cleavage consensus sites on a variety of proteins. Instead of just binding the protein at one sitell these novel organic molecules (Table 2) bind at many sites including all the trypsin cleavage domains, thus achieving the capability of "painting" the entire exposed surface of the folded or unfolded protein. Applicants established that these masking molecules will bind to proteins with very high affinity with a high on-rate (KD<10-10M) and a low off rate. This insures that the protein painting is stable and can remain adherent following partial or complete linearization of the protein polypeptide chain.

Paints remain bound after protein dissociation, reduction and alkylation. Applicants have shown that the masking molecules will remain adherent to the protein molecule after exposure to levels of denaturant or detergent treatments that can dissociate protein-protein binding partners. Applicants have shown that once the masking molecules are bound to the protein in solution, and the unbound masking molecules are washed away, the bound masking molecules prevent trypsin cleavage at a location at or near the masking pigment binding site.

Paints are excluded from hidden domains. Applicants demonstrate in Example 2 below that the paint molecules will bind to the native protein surface in solution but are excluded from internal protein-protein interaction domains that are hidden from the surface. This is a highly novel concept. Previous cross-linking methods to study protein interactions attach proteins together covalently at regions of interaction. Thus, the cross-linking methods function in a manner completely opposite to applicants' technology which leaves only the interacting domains unmodified and unmasked. Moreover, applicants' method leaves the unpainted binding domains exposed and ready for any type of structural or functional analysis.

Palettes of paints achieve different binding mechanisms. The instant organic dye derivative molecules bind to regions of the protein surface using different mechanisms for each type of "paint". Some paints prefer hydrophobic sites while others prefer hydrophilic or anionic or cationic regions. Applicants have determined that the binding affinity and protein binding region specificity is a function of the side chain composition of the ring substitutions and the primary structure of the molecule. Applicants have shown that even one class of pigment mask molecules will bind to the protein molecule at a multiple number of specific sites. Adding additional classes of paint mask molecules, which recognize different classes of protein domains, can fill in the gaps such that a proper mixture of paint molecules will attain full coverage of all the exposed regions of the protein or block all the protease cleavage sites or all the ligand binding sites.

EXAMPLE 2

Figure 4:
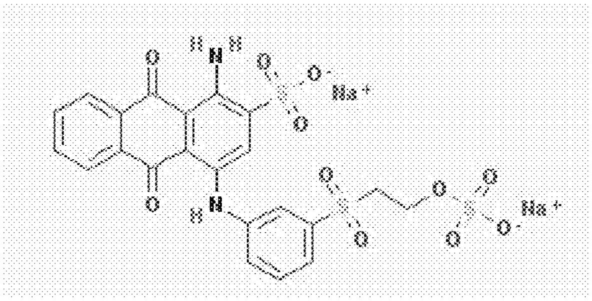
FIG. 4: Chemical structure of masking molecule Remazol Brilliant Blue R (RBB).

Binding of Masking Affinity Molecules to the Surface of Proteins Blocks Trypsin Recognition Sites and Masks Trypsin Generation of Cleavage Fragments Methods: Bovine serum albumin (BSA), aprotinin, and carbonic anhydrase II (1 mg/mL in PBS) were mixed with 10 molar excess disodium 1-amino-9,10-dioxo-4-[3-(2-sulfonatooxyethylsulfonyl) anilino] anthracene-2-sulfonate (RBB FIG. 4). Protein solutions were prepared in parallel with the same concentration without adding RBB, as controls. The solutions were immediately passed through a Sephadex column (PD MiniTrap G 25, GE Healthcare) and denatured with 8 M urea, reduced with 1 M dithiothreitol, alkylated with 0.5 M iodoacetamide, digested with trypsin, and subjected to mass spectrometry analysis (LTQ Orbitrap, Thermo Scientific).

Figure 5:
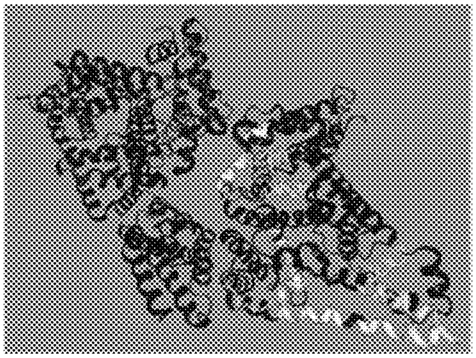
FIG. 5: Masked regions of BSA identified. The masked region is shown (light areas).
Figure 6:
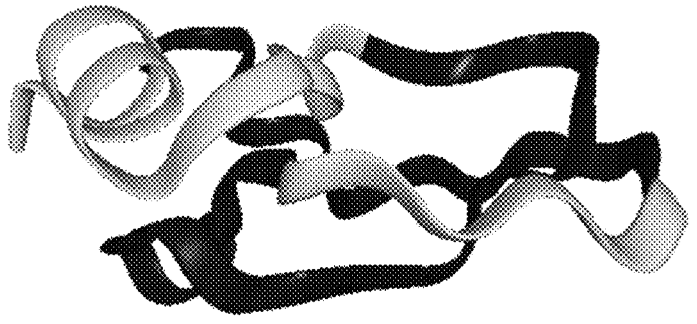
FIG. 6: Masked regions of native protein aprotinin identified on the native protein aprotinin. Masked regions are shown (light areas).

Results: Comparison of the MS derived amino acid sequences indicated that the masking molecules effectively blocked trypsin cleavage and over multiple regions of the proteins as shown below the top sequence (1M) is in the presence of the masking molecules and the bottom sequence is in the absence of the masking molecule (0M). The sequences in bold in the (0M) line identifies the masked region, the sequences in italics in both (0M) and (1M) lines are MS identified peptide fragments. Masked regions are shown in a three-dimensional representation of the proteins in FIGS. 5 and 6.

Bovine serum albumin (SEQ ID NO: 1):
1M...MKWVTFISLLLLFSSAYSRGVFRRDTHKSEIAHRFKDLGEEHFKGLVLIAFSQYLQQCPF
0M...MKWVTFISLLLLFSSAYSRGVFRRDTHKSEIAHRFKDLGEEHFK*GLVLIAFSQYLQQCPF*

1M...DEHVK*LVNELTEFAK*TCVADESHAGCEKSLHTLFGDELCKVASLRETYGDMADCCEKQEP
0M...*DEHVKLVNELTEFAK*TCVADESHAGCEK*SLHTLFGDELCK*VASLRETYGDMADCCEKQEP

1M...ERNECFLSHKDDSPDLPKLKPDPNTLCDEFKADEKKFWGKYLYEIARRHPYFYAPELLYY
0M...ERNECFLSHKDDSPDLPK*LKPDPNTLCDEFK*ADEKKFWGK*YLYEIARRHPYFYAPELLYY*

1M...ANKYNGVFQECCQAEDKGACLLPKIETMREKVLASSARQRLRCASIQKFGERALKAWSVA
0M...*ANK*YNGVFQECCQAEDKGACLLPKIETMREKVLASSARQRLRCASIQKFGERALKAWSVA

1M...RLSQKFPKAEFVEVTKLVTDLTKVHKECCHGDLLECADDRADLAKYICDNQDTISSKLKE
0M...RLSQKFPKAEFVEVTKLVTDLTKVHKECCHGDLLECADDRADLAKYICDNQDTISSKLKE

1M...CCDKPLLEKSHCIAEVEKDAIPENLPPLTADFAEDKDVCKNYQEAKDAFLGSFLYEYSRR
0M...CCDKPLLEKSHCIAEVEKDAIPENLPPLTADFAEDKDVCKNYQEAK*DAFLGSFLYEYSR*R

1M...HPEYAVSVLLRLAKEYEATLEECCAKDDPHACYSTVFDKLKHLVDEPQNLIKQNCDQFEK
0M...HPEYAVSVLLRLAK*EYEATLEECCAKDDPHACYSTVFDK*LK*HLVDEPQNLIK*QNCDQFEK

1M...*LGEYGFQNALIVR*YTR*KVPQVSTPTLVEVSR*SLGKVGTRCCTKPESERMPCTEDYLSLIL
0M...*LGEYGFQNALIVR*YTR*KVPQVSTPTLVEVSR*SLGKVGTRCCTKPESER*MPCTEDYLSLIL*

1M...NRLCVLHEKTPVSEKVTKCCTESLVNRRPCFSALTPDETYVPKAFDEKLFTFHADICTLP
0M...*NR*LCVLHEKTPVSEKVTKCCTESLVNR*RPCFSALTPDETYVPK*AFDEKLFTFHADICTLP

1M...DTEKQIKKQTALVELLKHKPKATEEQLK*TVMENFVAFVDK*CCAADDKEACFAVEGPKLVV
0M...DTEKQIKKQTALVELLKHKPKATEEQLK*TVMENFVAFVDKCCAADDKEACFAVEGPKLVV*

1M...*STQTALA*
0M...*STQTALA*

Carbonic anhydrase II, *Bos taurus* (SEQ ID NO: 2).
1M...MSHHWGYGKHNGPEHWHKDFPIANGERQSPVDIDTKAVVQDPALKPLALVYGEATSRR*MVNNG HSFNVEYDDSQDKA*
0M...MSHHWGYGK*HNGPEHWHKDEPIANGERQSPVDIDTKAVVQDPALKPLALVYGEATSRRMVNNG HSFNVEYDDSQDKA*

1M...*VLK*DGPLTGTYRLVQFHFHWGSSDDQGSEHTVDRKKYAAELHLVHWNTKYGDFGTAAQQPDGL AVVGVFLK*VGDANP*
0M...*VLK*DGPLTGTYR*LVQFHFHWGSSDDQGSEHTVDRKKYAAELHLVHWNTKYGDFGTAAQQPDGL AVVGVFLKVGDANP*

1M...*ALQKVLDALDSIKTK*GKSTDFPNFDPGSLLPNVLDYWTYPGSLTTPPLLESVTWIVLK*EPISV SSQQMLK*FRTLNFN
0M...*ALQKVLDALDSIKTK*GKSTDFPNFDPGSLLPNVLDYWTYPGSLTTPPLLESVTWIVLK*EPISV SSQQMLK*FR*TLNFN*

1M...AEGEPELLMLANWRPAQPLKNRQVRGFPK
0M...*AEGEPELLMLANWR*PAQPLKNRQVRGFPK

Aprotinin, *Bos taurus* (SEQ ID NO: 3):
1M...*RPDFCLEPPYTGPCK*ARIIRYFYNAK*AGLCQTFVYGGCR*AKRNNFKSAEDCMRTCGGA
0M...*RPDFCLEPPYTGPCK*AR*IIRYFYNAKAGLCQTFVYGGCR*AKR*NNFKSAEDCMR*TCGGA

EXAMPLE 3

Application of the Masking Molecule(s) to Directly Sequence Interface Contact Areas Between Interacting Proteins The IL1beta receptor and its protein ligand were chosen to demonstrate a utility of the present technology. Three-dimensional structure of this complex is known by X ray crystallography (*Nature,* 386, 190-194, 1997).

Methods: The receptor protein and ligand protein were purchased from Adipogen and Biolegend, respectively. A solution containing the receptor protein and ligand was prepared (0.05 mg/mL in PBS) and placed at 37 C for 1 hour to allow binding between the two molecules to take place. The affinity masking molecule disodium 1-amino-9,10-dioxo-4-[3-(2-sulfonatooxyethylsulfonyl) anilino] anthracene-2-sulfonate (RBB) was added at a 10:1 molar excess. In order to separate the excess unbound masking molecule, the solution was immediately passed through a Sephadex column (PD MiniTrap G 25, GE Healthcare). The complexed proteins coated with the masking molecules were denatured with 8 M urea, reduced with 1 M dithiothreitol, alkylated with 0.5 M iodoacetamide, digested with trypsin, and subjected to mass spectrometry analysis (LTQ Orbitrap, Thermo Scientific).

The mass spectrometry sequence was obtained for the proteins when they were coated with the dye in the associated or dissociated states. The sequence shown in the lower line is in the presence of the complex (C). In the presence of the protein complex, the masking molecule cannot gain access to the binding interface regions of the two protein molecules therefore these regions will become available for mass spectrometry sequencing by trypsin cleavage as shown in FIG. 1.

Figure 7A:
FIG. 7A-B: Exemplary binding sites identified shown for a receptor protein (FIG. 7A) and a ligand protein (FIG. 7B).
Figure 7B:
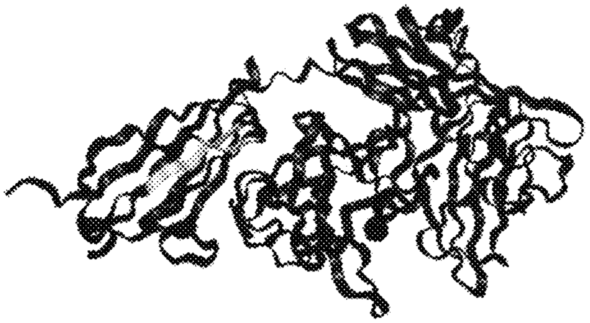
Figure 8A:
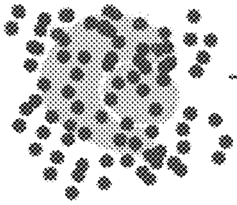
FIG. 8A-F: Protein painting workflow.
Figure 8B:
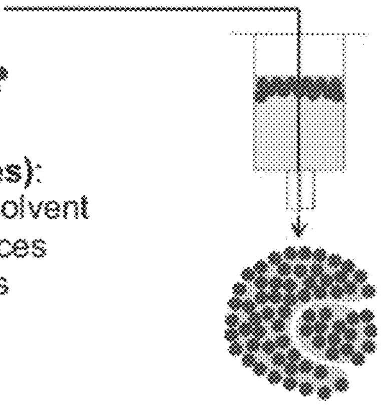
Figure 8C:
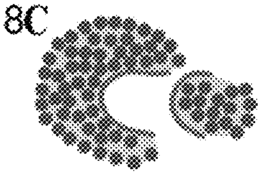
Figure 8D:
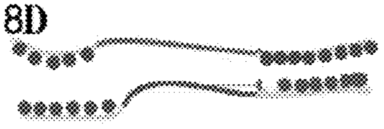
Figure 8E:
Figure 8F:
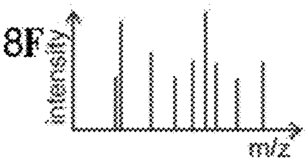

Results: The following internal regions known to play role in the binding domain based on crystallography were found by the invention method. These regions were sequenced only in the complexed proteins because the internal interface region was not masked by the affinity masking molecule. An example of one of these binding sites is shown in FIG. 7. In fact, the ligand binding site identified in FIG. 7 is considered to be a hot spot for the interaction and necessary for the binding to the receptor.

The area in italics in the lower sequence is sequenced only in the presence of the complex (C). The regions identified in the red boxes by the inventive method are predicted by X-ray crystallography to comprise hot spots of direct interaction, which indicates close proximity contact between the interacting proteins. The majority of the predicted internal interface sequences were correctly revealed by the invention.

IL1beta (SEQ ID NO: 4):

1M. . .APVRSLNCTLRDSQQK*SLVMSGPYELK*ALHLQGQDMEQQVVFSMSFVQGEESNDKIPVAL<br>
C. . .APVRSLNCTLRDSQQK*SLVMSGPYELK*ALHLQGQDMEQQVVFSMSFVQGEESNDKIPVAL

1M. . .GLKEKNLYLSCVLKDDKPTLQLESVDPKNYPKKKMEKRFVFNKIEINNKLEFESAQFPNW<br>
C. . .GLK*EKNLYLSCVLKDDKPTLQLES*VDPKNYPKKKMEKR*FVFNKIEINN*KLEFESAQFPNW

1M. . .YISTSQAENMPVFLGGTKGGQDITDFTMQFVSS<br>
C. . .YISTSQAENMPVFLGGT*KGGQDITDFTMQFVSS*

Il1 receptor (SEQ ID NO: 5):

1M. . .DKCKEREEKIILVSSANEIDVRPCPLNPNEHKGTITWYKDDSKTPVSTEQASRIHQHKEK<br>
C. . .DKCKEREEKIILVSSANEIDVRPCPLNPNEHK*GTITWYKDDSKTPVSTEQASR*IHQHKEK

1M. . .LWFVPAKVEDSGHYYCVVRNSSYCLRIKISAK*FVENEPNLCYNAQAIFK*QK*LPVAGDGGL*<br>
C. . .LWFVPAK*VEDSGHYYCVVR*NSSYCLRIKISAK*FVENEPNLCYNAQAIFK*QK*LPVAGDGGL*

1M. . .*VCPYMEFFK*NENNELPKLQWYKDCKPLLLDNIHFSGVKDR*LIVMNVAEK*HRGNYTCHASY<br>
C. . .*VCPYMEFFKNENNELPK*LQWYKDCK*PLLLDNIHFSGVK*DR*LIVMNVAEK*HRGNYTCHASY

1M. . .TYLGKQYPITRVIEFITLEENKPTRPVIVSPANETMEVDLGSQIQLICNVTGQLSDIAYW<br>
C. . .TYLGKQYPITRVIEFITLEENKPTRPVIVSPANETMEVDLGSQIQLICNVTGQLSDIAYW

1M. . .KWNGSVIDEDDPVLGEDYYSVENPANKRRSTLITVLNISEIESRFYKHPFTCFAKNTHGI<br>
C. . .KWNGSVIDEDDPVLGEDYYSVENPANKRR*STLITVLNISEIESRFYKHPFTCFA*KNTHGI

1M. . .DAAYIQLIYPVTNFQK<br>
C. . .DAAYIQLIYPVTNFQK

EXAMPLE 4

Small Organic Molecules that Bind to the Surface of Folded Proteins and do not Complex with Internal Domains of Protein-Protein Interactions Examples of additional small aryl hydrocarbon ring containing small organic molecules bind to the surface of a native protein and remain complexed following denaturation or unfolding of the protein, demonstrates two aspects of the subject invention: a. The binding of the small organic molecules is localized to multiple sites restricted to the surface of the protein, and excluded from internal domains of protein-protein interactions and b. The trypsin cleavage pattern analyzed by mass spectrometry with and without prior binding to the small molecule, and following unfolding of the protein, reveals binding locations of the small molecule because they block trypsin cleavage sites. Three dimensional representations and molecular docking studies show that these small organic molecules bind only to trypsin cleavage sites on the surface of the folded molecule and fail to bind to trypsin cleavage sites on the inner protected interaction contact points of the folded protein. Thus, these molecules can be employed to reveal a) the inner contact domains of a single folded protein or b) the contact domains of two or more interacting proteins.

Molecule 1: N-(4-{bis[4-(dimethylamino)phenyl]methylene}-2,5-cyclohexadien-1-ylidene)methanaminium chloride (MV), CAS 8004-87-3

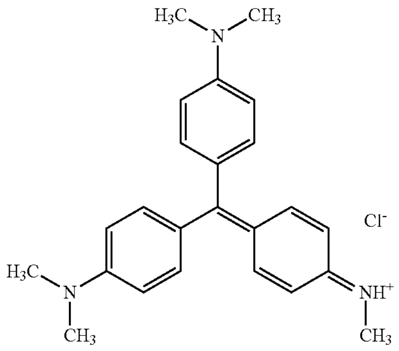

1.1 Linear representation of IL1R1 molecule, soluble portion. Trypsin sites blocked by MV are in bold:

(SEQ ID NO: 5)

1 DKCKEREEKIILVSSANEIDVRPCPLNPNEHKGTITWYKDDSKTPVSTEQASRIHQHKEK 60

61 LWFVPAKVEDSGHYYCVVRNSSYCLRIKISAKFVENEPNLCYNAQAIFKQKLPVAGDGGL 120

121 VCPYMEFFKNENNELPKLQWYKDCKPLLLDNIHFSGVKDRLIVMNVAEKHRGNYTCHASY 180

181 TYLGKQYPITRVIEFITLEENKPTRPVIVSPANETMEVDLGSQIQLICNVTGQLSDIAYW 240

241 KWNGSVIDEDDPVLGEDYYSVENPANKRRSTLITVLNISEIESRFYKHPFTCFAKNTHGI 300

301 DAAYIQLIYPVTNFQK. 316

Figure 17A:
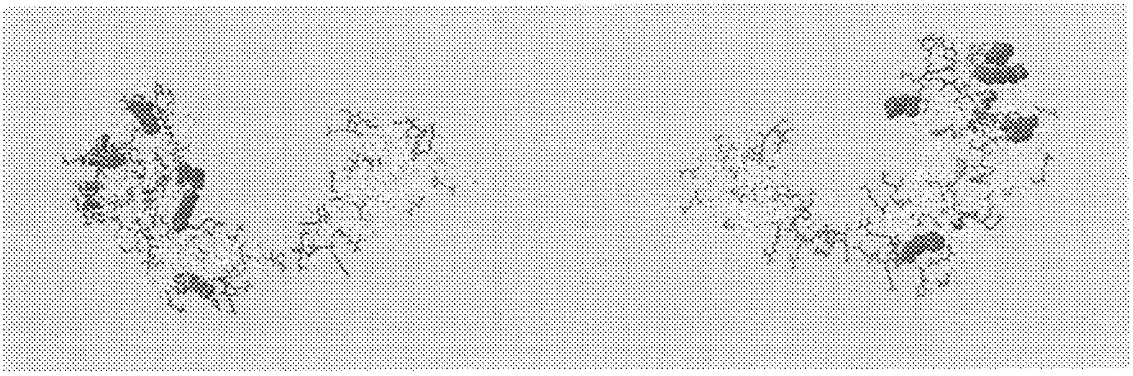
FIG. 17A-B: Three-dimensional representation of IL1R1 molecule, soluble portion.

1.2 Three-dimensional representation of IL1R1 molecule, soluble portion (see FIG. 17*a*).

Figure 17B:
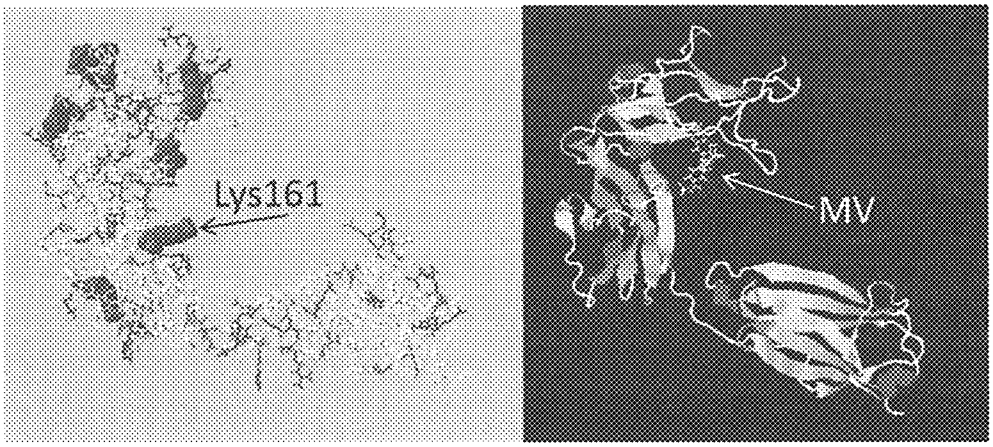

1.3 MV binding to trypsin sites is confirmed by molecular docking (see FIG. 17*b*).

Molecule 2. 3,3'-Diethylthiacarbocyanine iodide (DECI), CAS 905-97-5

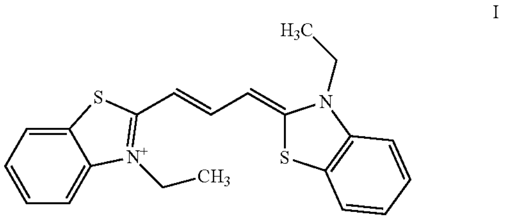 [SMILES: CCN1/C(=C/C=C/c2sc3ccccc3[n+]2CC)Sc2ccccc21]

2.1 Linear representation of IL1R1 molecule, soluble portion. Trypsin sites blocked by DECI are in bold:

(SEQ ID NO: 5)

1 DKCKEREEKIILVSSANEIDVRPCPLNPNEHKGTITWYKDDSKTPVSTEQASRIHQHKEK 60

61 LWFVPAKVEDSGHYYCVVRNSSYCLRIKISAKFVENEPNLCYNAQAIFKQKLPVAGDGGL 120

121 VCPYMEFFKNENNELPKLQWYKDCKPLLLDNIHFSGVKDRLIVMNVAEKHRGNYTCHASY 180

181 TYLGKQYPITRVIEFITLEENKPTRPVIVSPANETMEVDLGSQIQLICNVTGQLSDIAYW 240

241 KWNGSVIDEDDPVLGEDYYSVENPANKRRSTLITVLNISEIESRFYKHPFTCFAKNTHGI 300

301 DAAYIQLIYPVTNFQK. 316

Figure 18A:
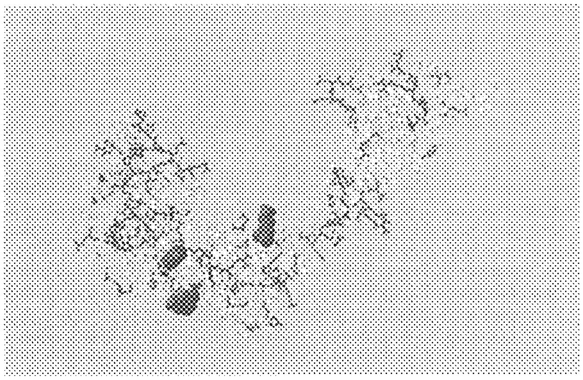
FIG. 18A-B: Three-dimensional representation of IL1R1 molecule, soluble portion.

2.2 Three-dimensional representation of IL1R1 molecule, soluble portion (see FIG. 18*a*).

Figure 18B:
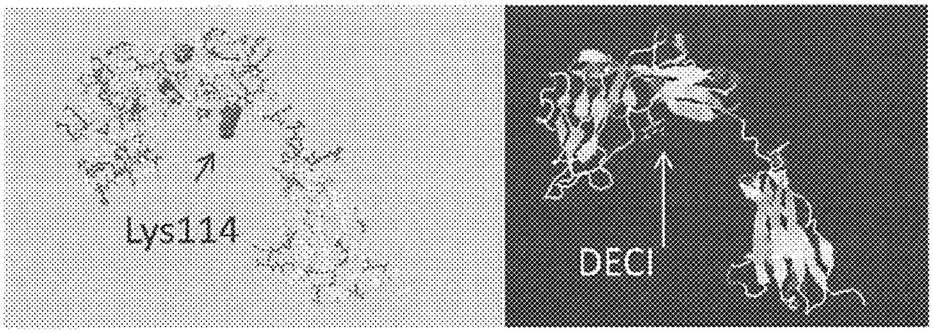

2.3 DECI binding to trypsin sites is confirmed by molecular docking (see FIG. 18*b*).

Molecule 3. 8-Anilino-1-naphthalenesulfonic acid (ANSA), CAS 82-76-8

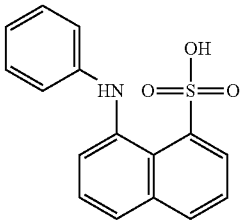 [SMILES: O=S(=O)(O)c1cccc2cccc(Nc3ccccc3)c12]

3.1 Linear representation of IL1R1 molecule, soluble portion. Trypsin sites blocked by ANSA are in bold:

(SEQ ID NO: 5)

1 DKCKEREEKIILVSSANEIDVRPCPLNPNEHKGTITWYKDDSKTPVSTEQASRIHQHKEK 60

61 LWFVPAKVEDSGHYYCVVRNSSYCLRIKISAKFVENEPNLCYNAQAIFKQKLPVAGDGGL 120

121 VCPYMEFFKNENNELPKLQWYKDCKPLLLDNIHFSGVKDRLIVMNVAEKHRGNYTCHASY 180

181 TYLGKQYPITRVIEFITLEENKPTRPVIVSPANETMEVDLGSQIQLICNVTGQLSDIAYW 240

241 KWNGSVIDEDDPVLGEDYYSVENPANKRRSTLITVLNISEIESRFYKHPFTCFAKNTHGI 300

301 DAAYIQLIYPVTNFQK. 316

Figure 19A:
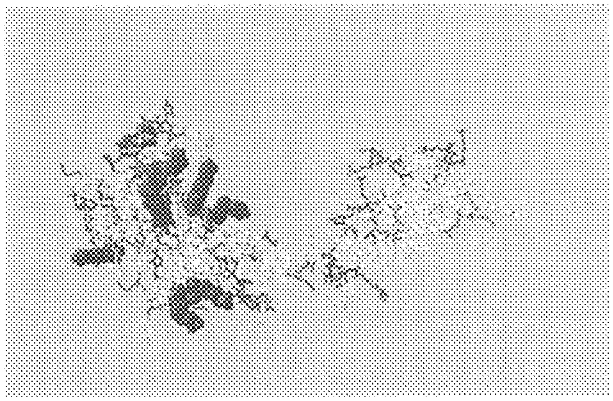
FIG. 19A-B: Three-dimensional representation of IL1R1 molecule, soluble portion.
Figure 19B:
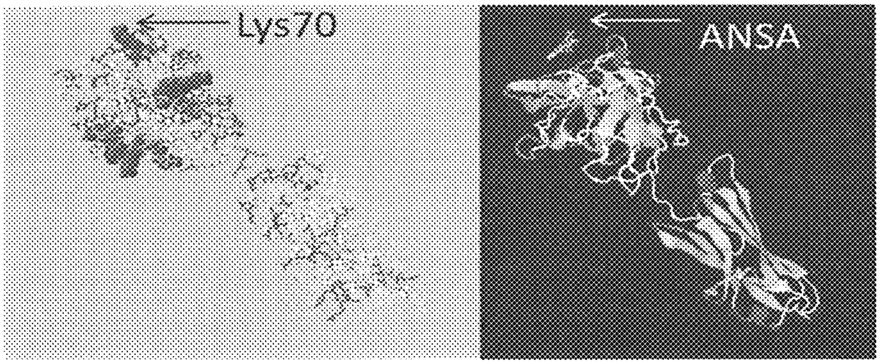

3.2 Three-dimensional representation of IL1R1 molecule, soluble portion (see FIG. 19*a*). 3.3 ANSA binding to trypsin sites is confirmed by molecular docking (see FIG. 19*b*).

EXAMPLE 5

Protein Painting Reveals 3-Way Hot-Spot Between IL1beta, IL1R1, and IL1RAcP

Protein painting can be demonstrated by studying multiple hot spots participating in the three-way interaction of IL1b ligand, its receptor IL1R1, and the accessory protein IL1RAcP. Interleukin signaling requires the interaction of all three proteins. Aberrant function of this complex is involved in a variety of diseases, including cancer, rheumatoid arthritis, systemic lupus erythematosus, inflammatory bowel disease, systemic vasculitis, neonatal bronchial dysplasia, and inflammatory bone and cartilage destruction. These diseases constitute a multi-billion-dollar market.

In so doing, the present inventors discovered a previously unknown 3-way hot spot between the accessory protein, the ligand, and the receptor. This novel information was used to create synthetic beta loop peptides corresponding to the three-way hot spot at the accessory protein. The peptide mimicking the interface blocked IL1beta signaling in ligand stimulated cells and could substitute for the entire truncated accessory protein as a competitive inhibitor. This same hot spot peptide mimic, and a monoclonal antibody raised against this sequence, blocked the three way complex formation between the IR1, 1L1beta and the accessory protein. Both the peptide and the monoclonal antibody now constitute new therapies for the treatment of diseases caused by aberrant interleukin signaling.

(1) General Overview

"Hot-spots" of protein-protein interaction constitute important drug targets. The instant application introduces aryl hydrocarbon containing organic dyes as "protein paints" for a new method using mass spectrometry to sequence only the hidden, unmodified contact interfaces between interacting native proteins. The instant protein painting technology can be used to sequence hot-spot domains between two, or three, interacting proteins, and use this information to create hot-spot mimic peptides and mAbs that block the interaction.

Protein-protein interfaces contain amino acid patches that are "hot spots" of interaction. Hot spots are important drug targets because they contribute the majority of the coupling stability and free energy of binding sites. For the vast majority of characterized binary protein-protein interactions, the identity of the two interacting proteins may be known, but the specific amino acid sequence of their hot spot domain remains unknown. Hot spots are difficult and time consuming to functionally define by existing methods because they are hidden inside the contact interface. Other than tomography/crystal structure analysis, current methods cannot directly identify the amino acid sequence of the physically interacting domains of native proteins, without substantial modification of the binding interface residues by crosslinking[5], step-wise mutation, or genetic tagging[2].

Figure 9C:
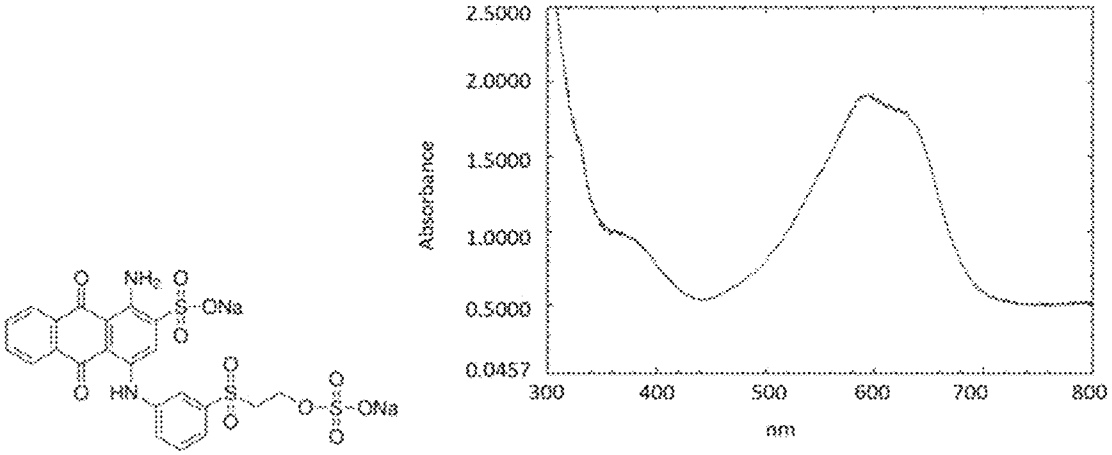
Figure 9D:
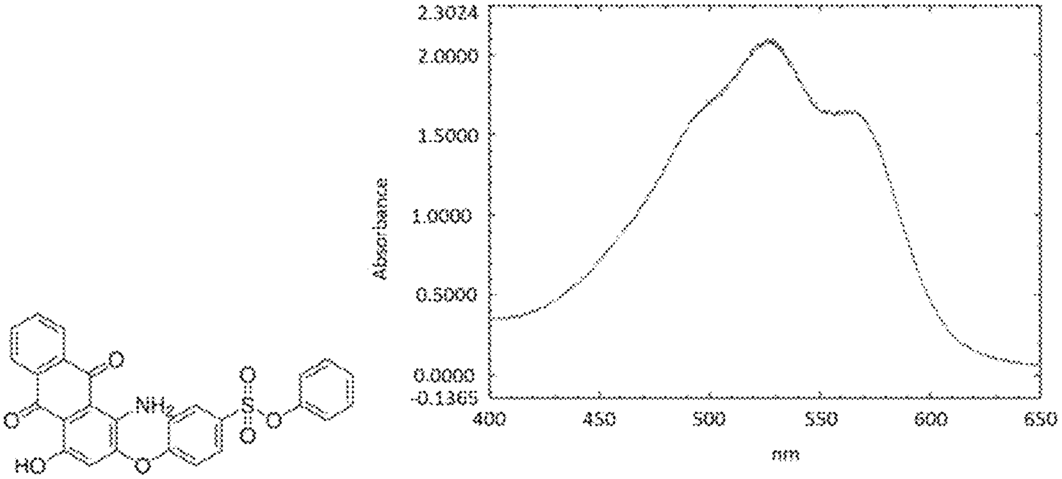
Figure 9E:
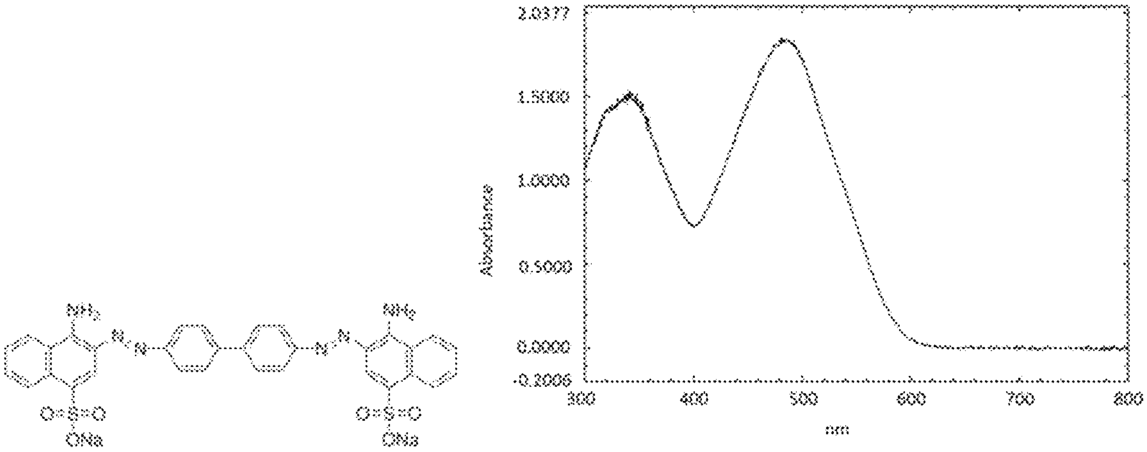
Figure 12B:
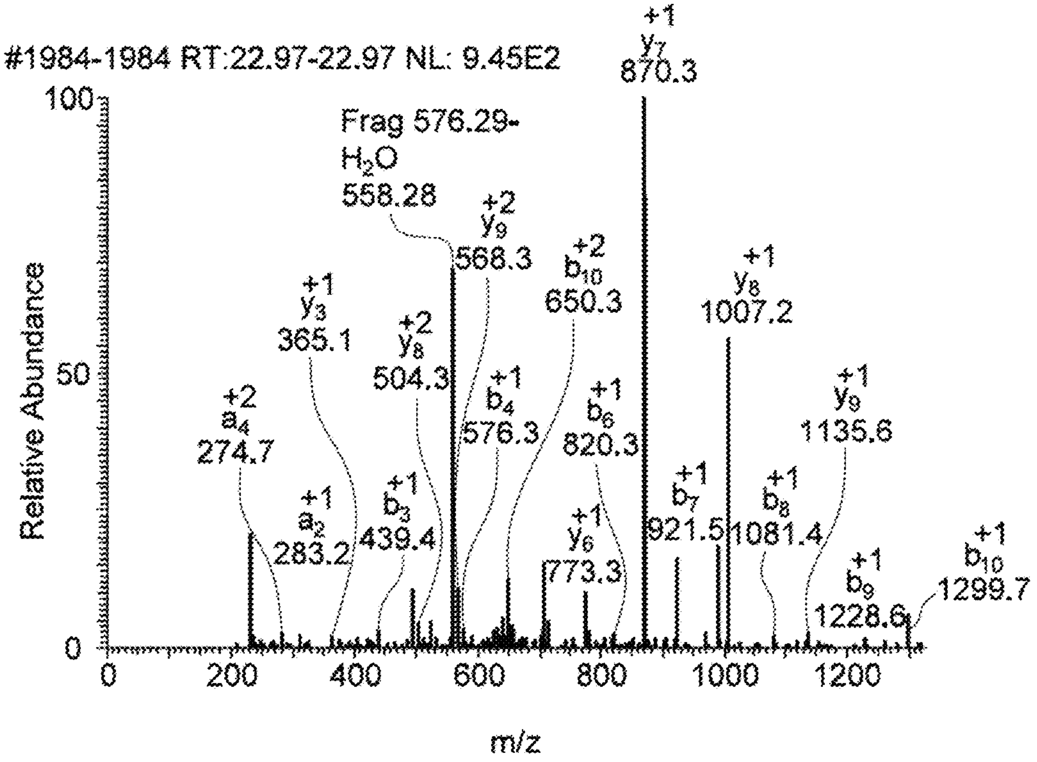
Figure 12C:
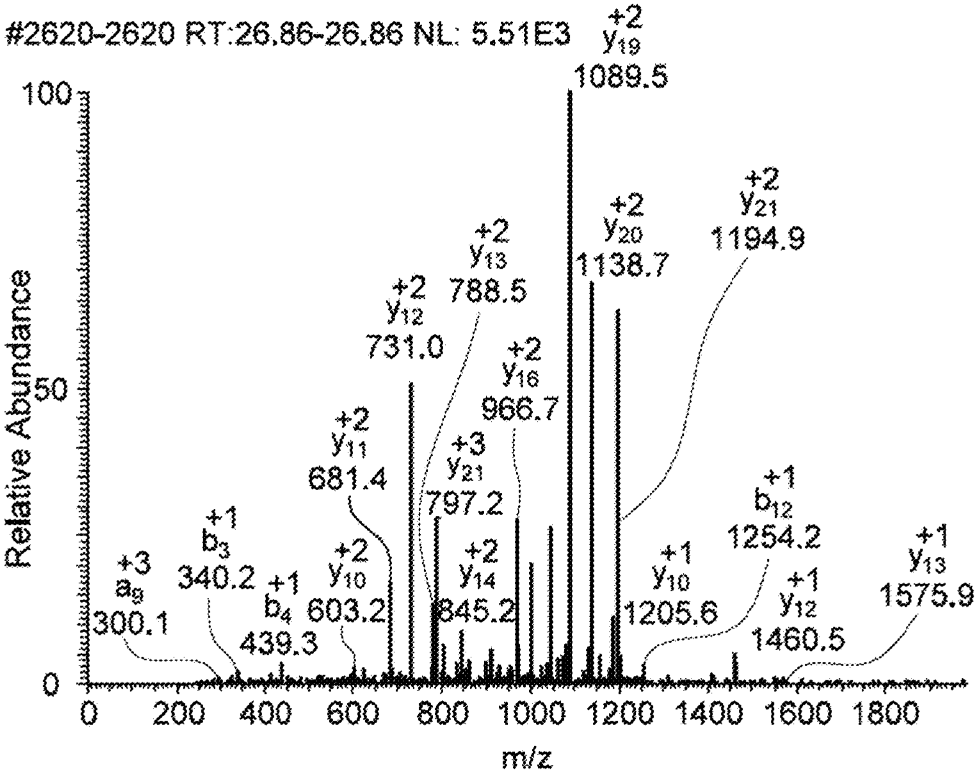
Figure 12D:
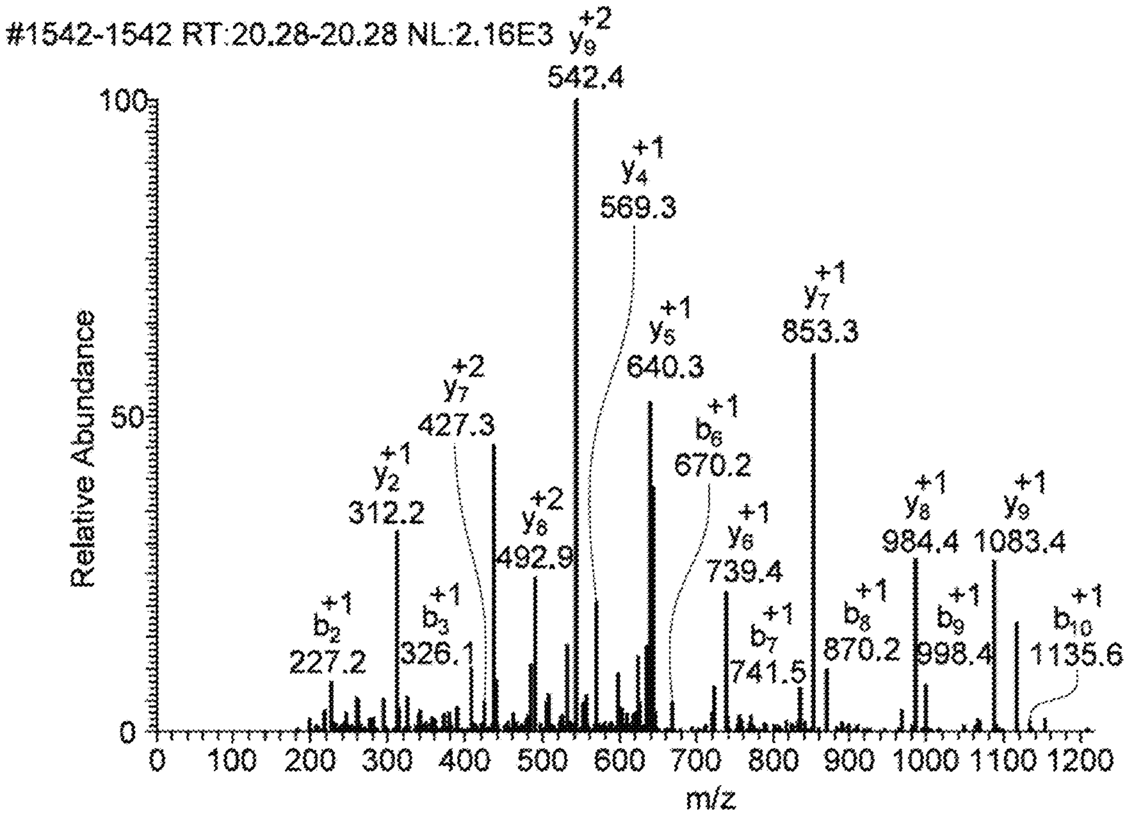
Figure 12E:
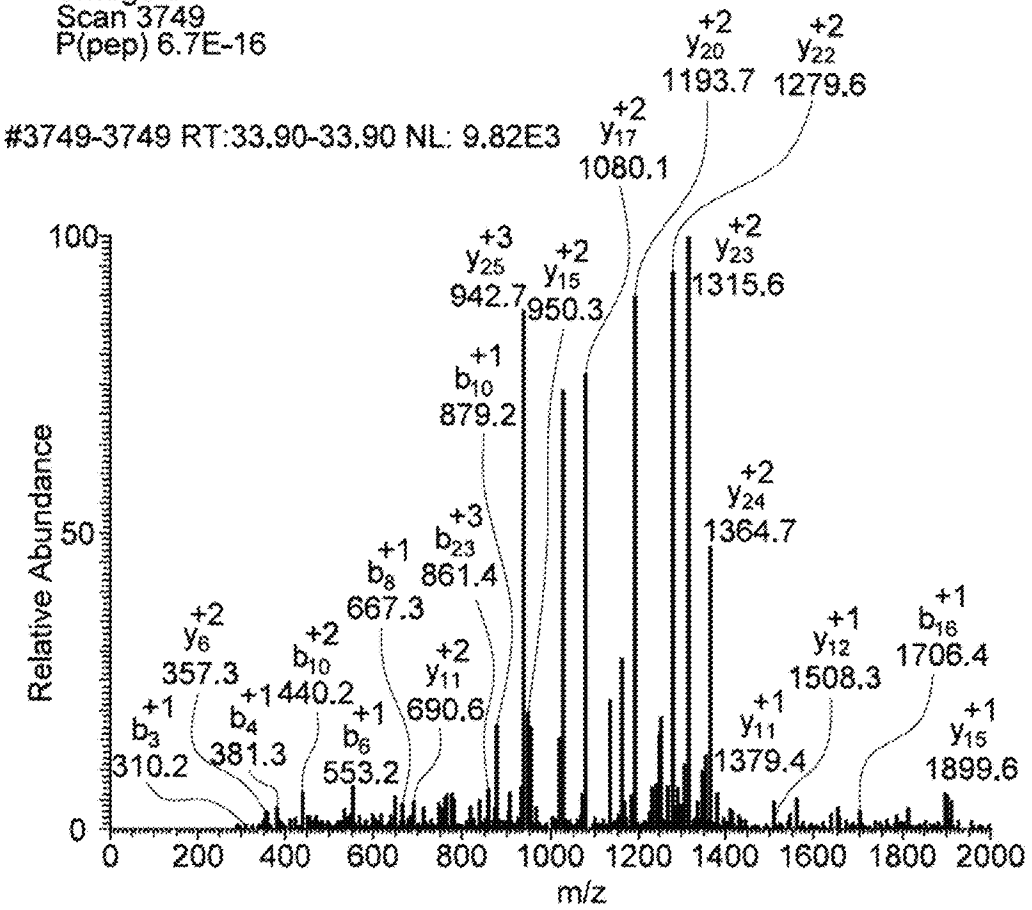
Figure 12F:
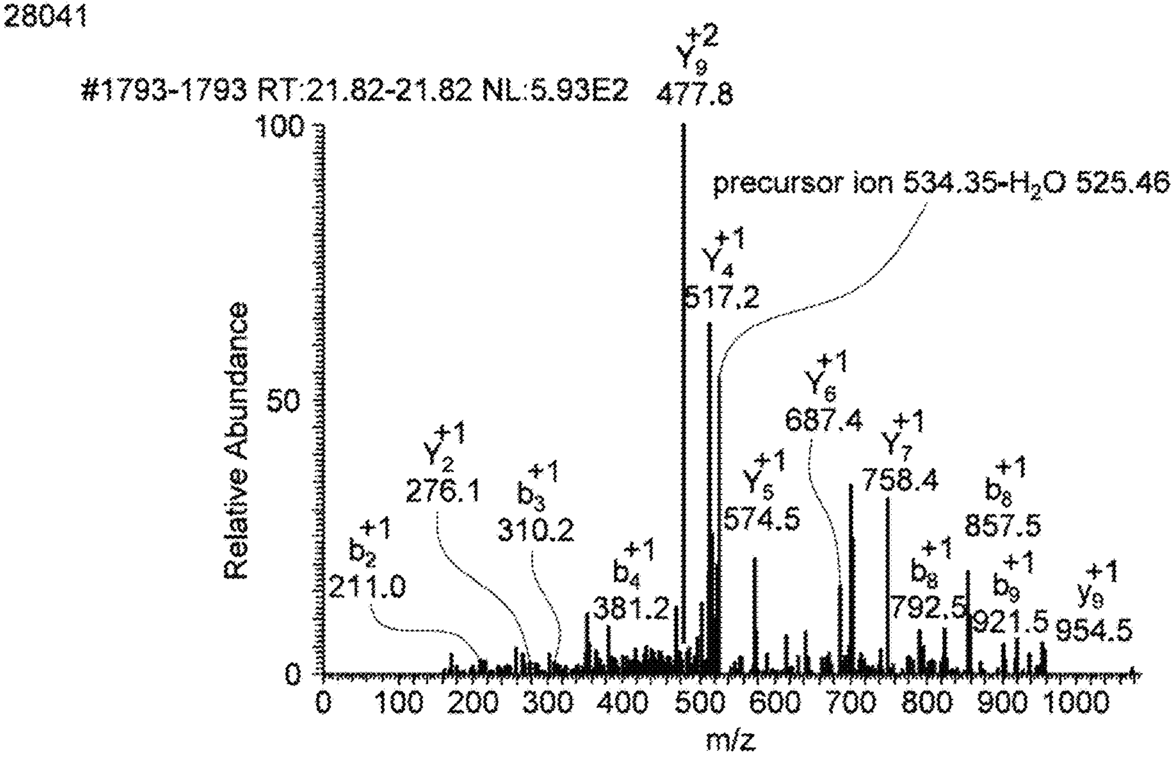
Figure 12G:
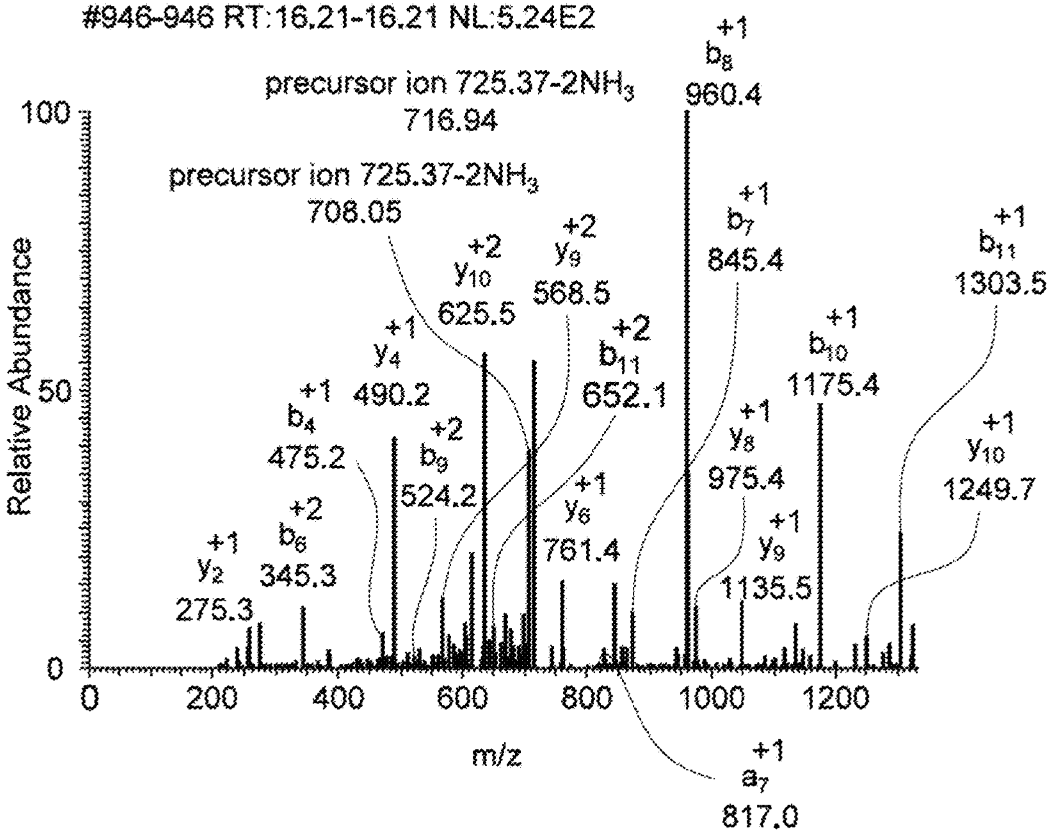
Figure 12H:
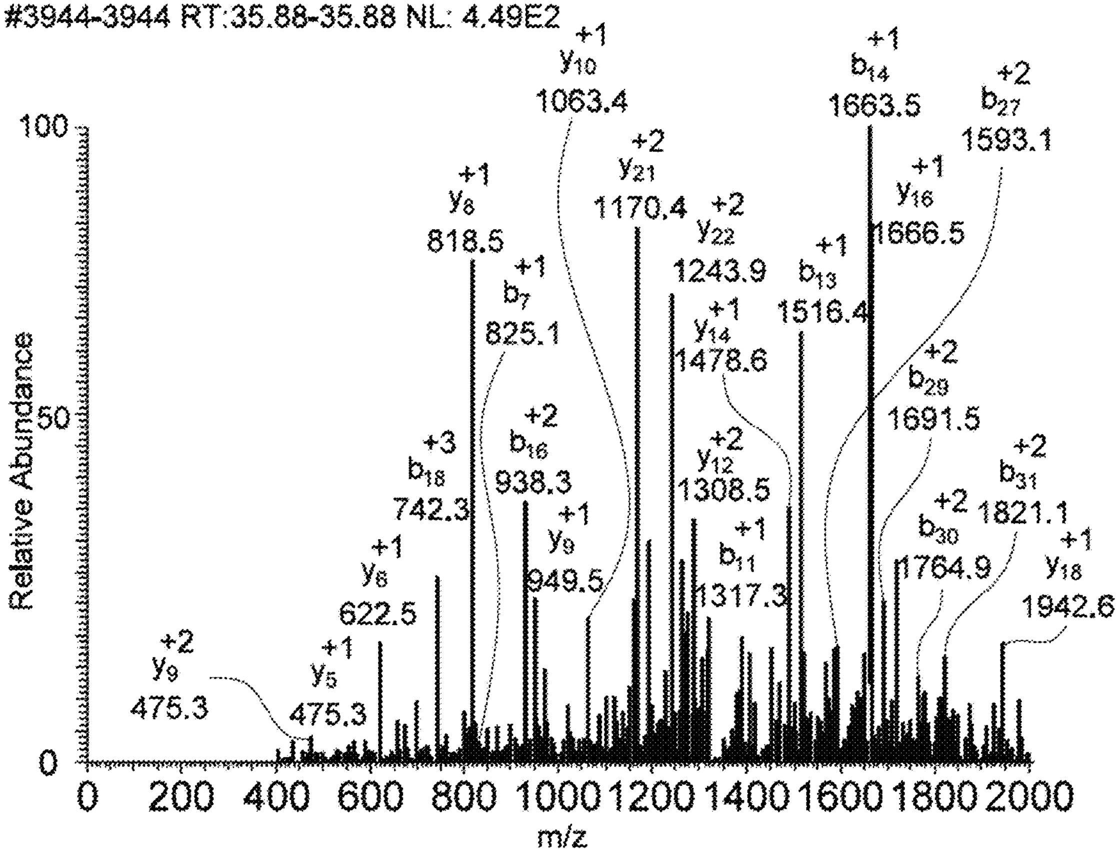
Figure 12I:
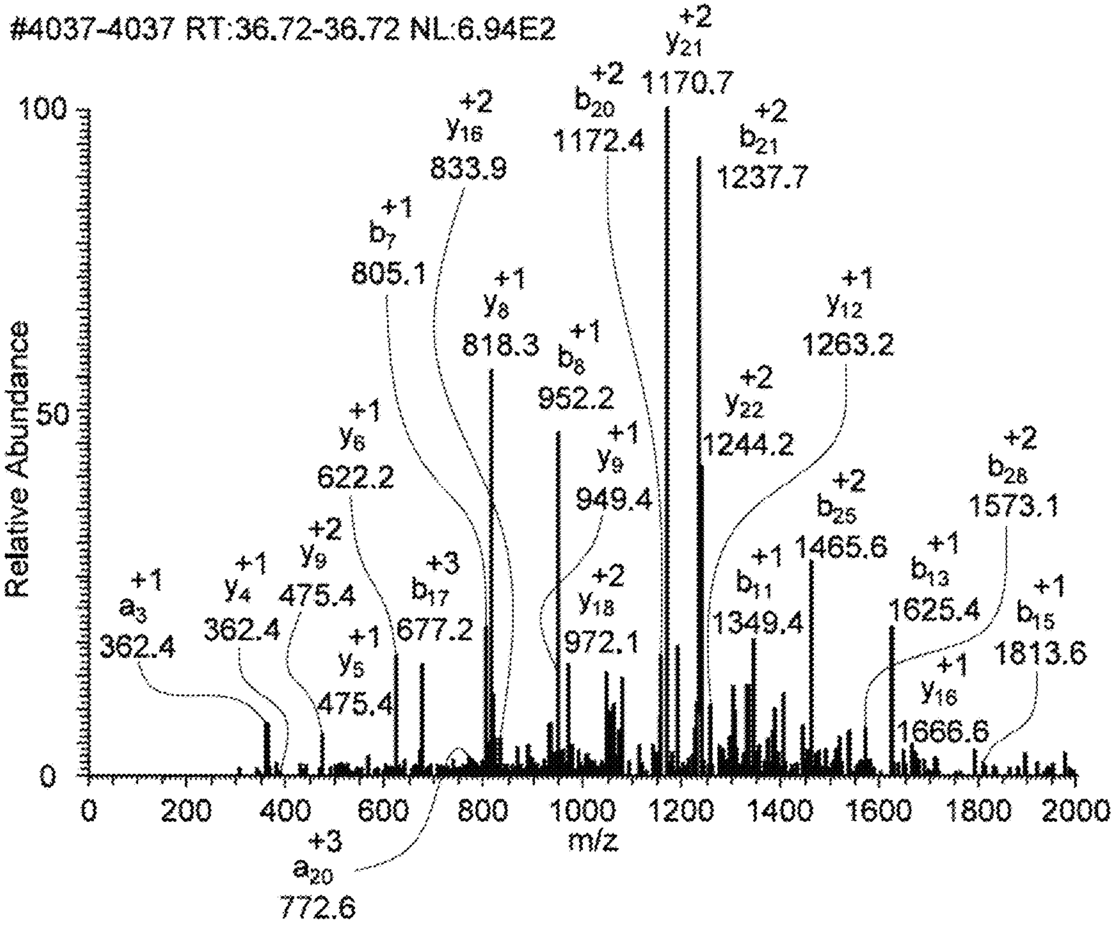
Figure 12J:
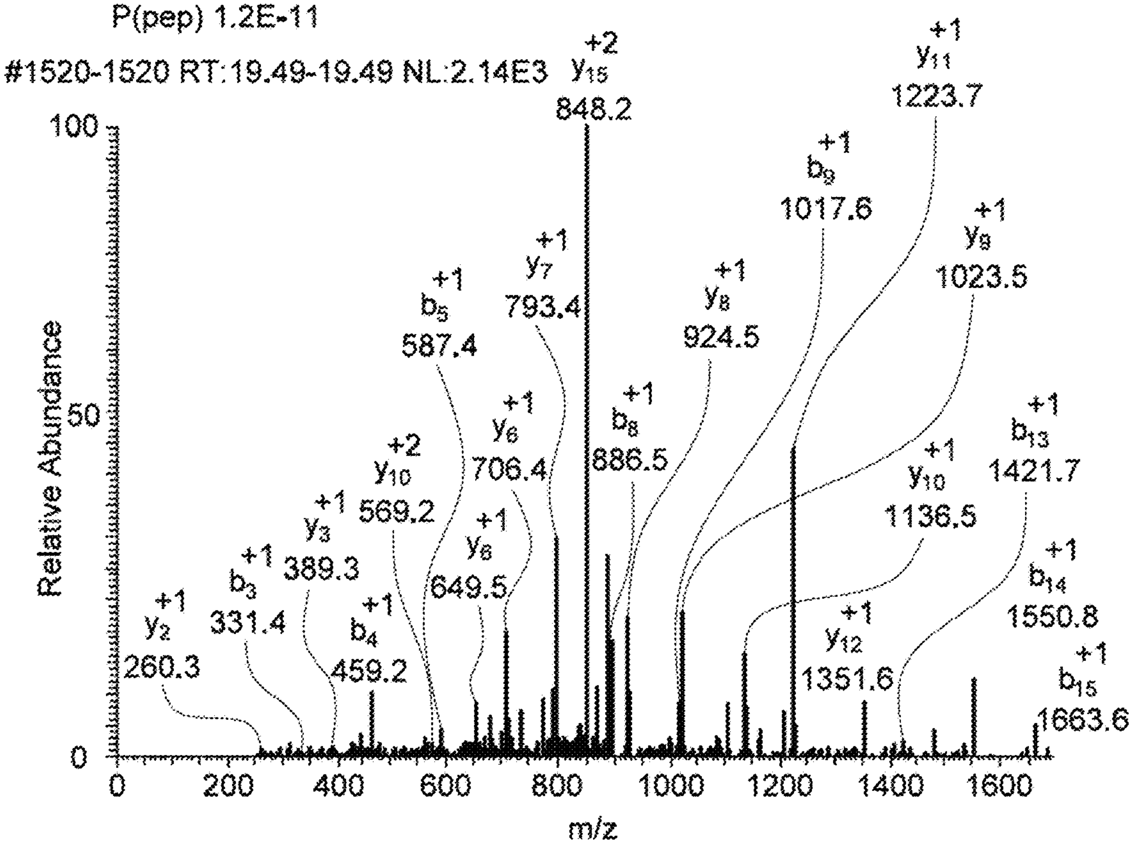

Here, a set of small molecule "paints" were introduced and used to rapidly expose, and exclusively sequence, the unmodified contact interface regions between two or more interacting native proteins, without crosslinking (FIG. 8). "Protein painting" is made possible because of Applicants' identification of a panel of small, synthetic aryl hydrocarbon containing organic dyes (FIG. 9), from a large number of candidate molecules (FIG. 15, FIG. 10), that bind to proteins as "molecular paints".

Figure 15A:
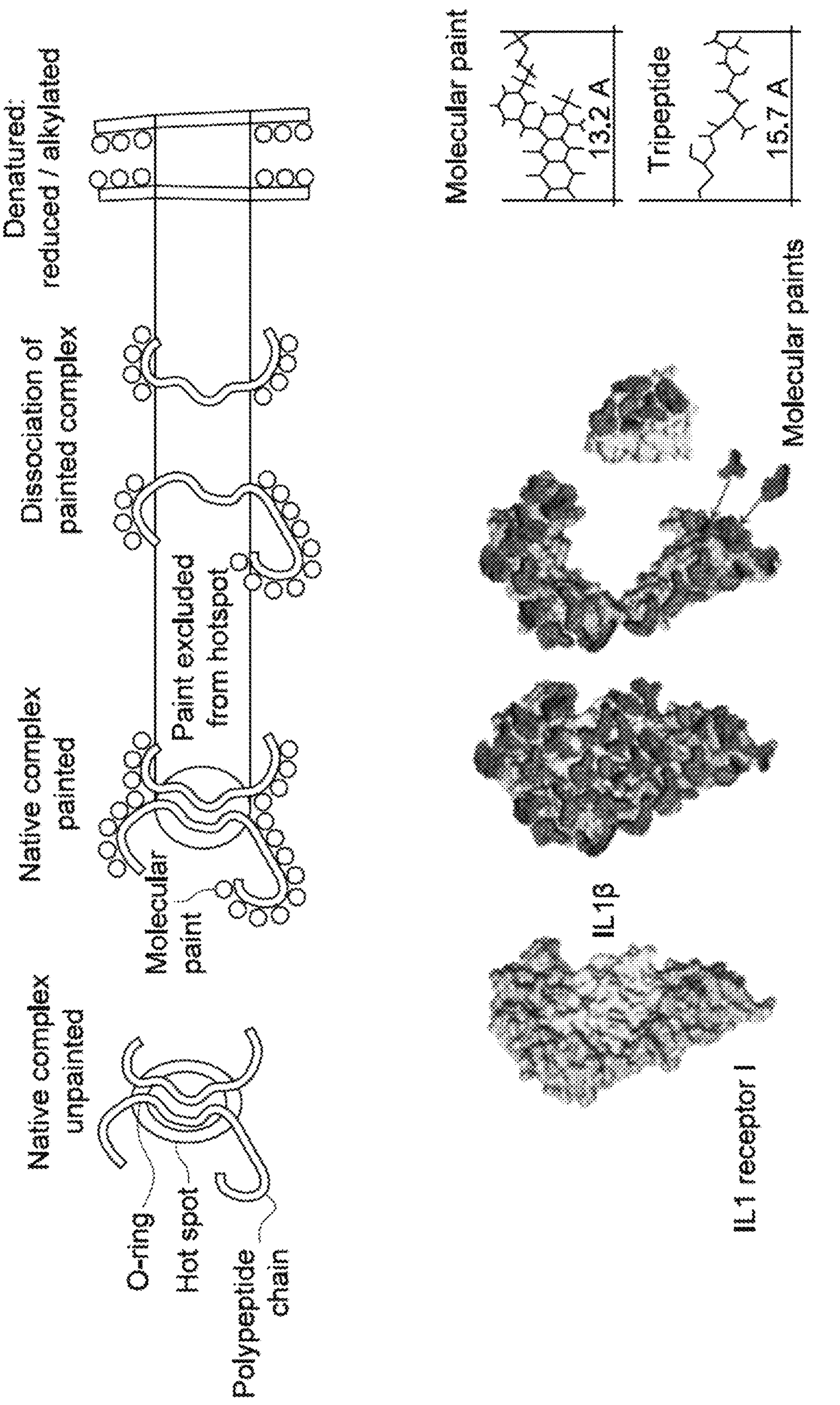
FIG. 15A-F: Protein painting exposes and sequences hidden native hot spot domains of protein-protein interactions.
Figure 15B:
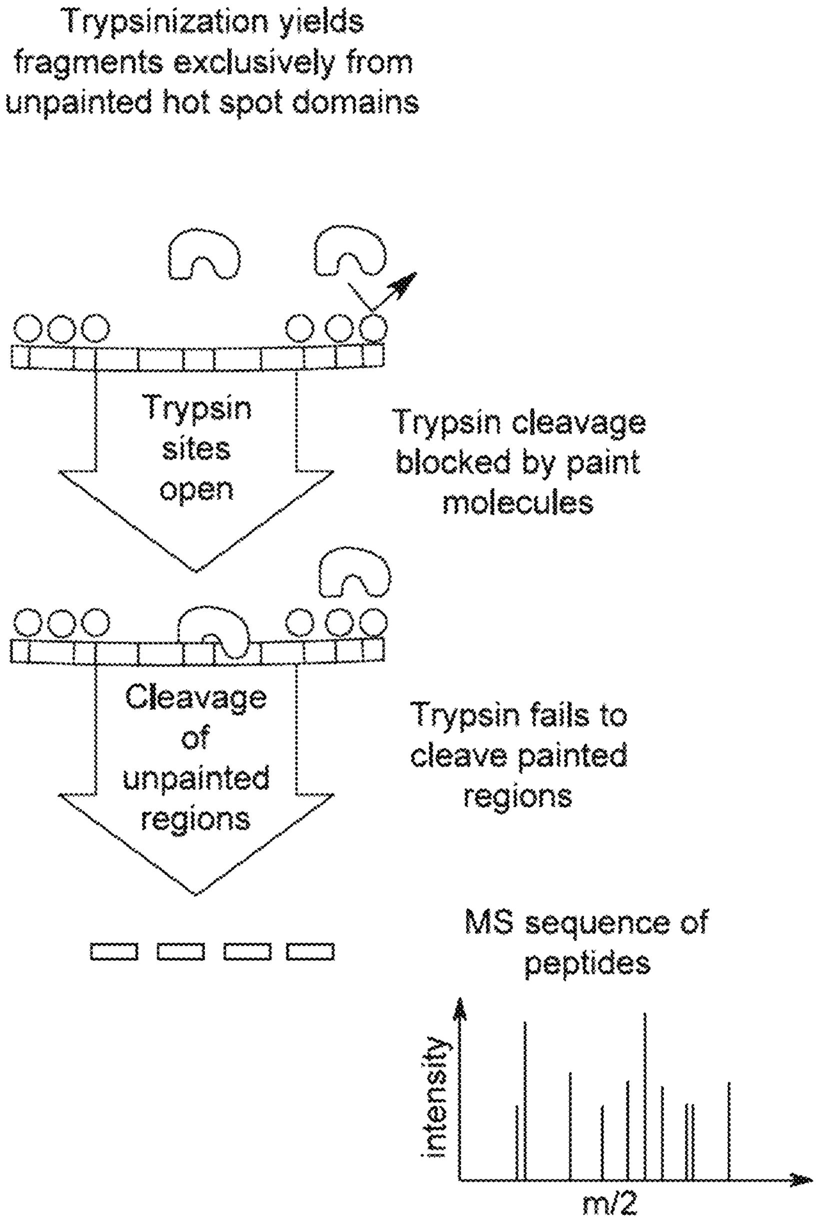
Figure 15C:
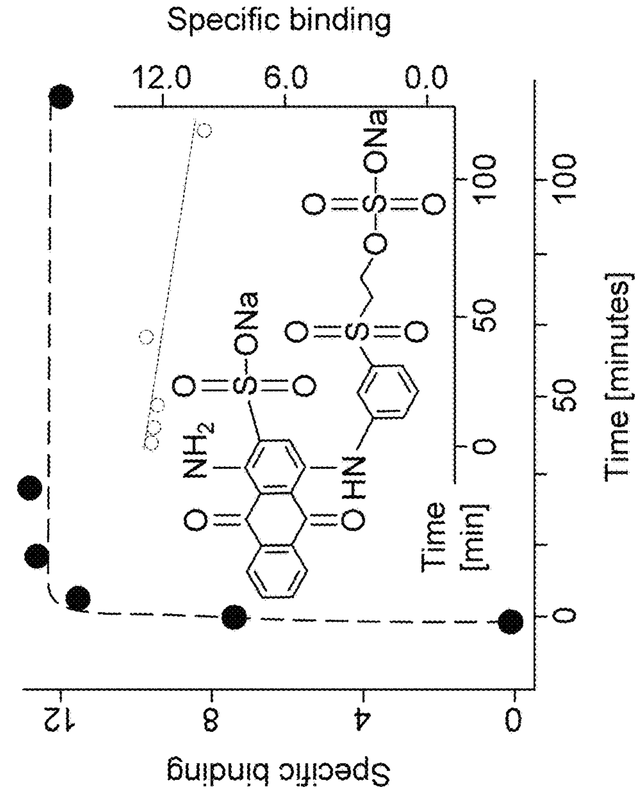
Figure 15D:
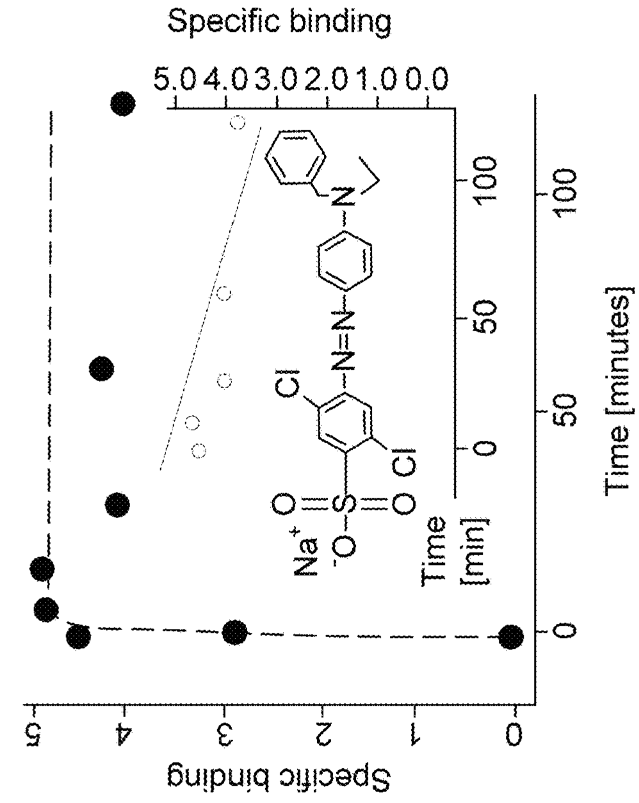
Figure 15F:
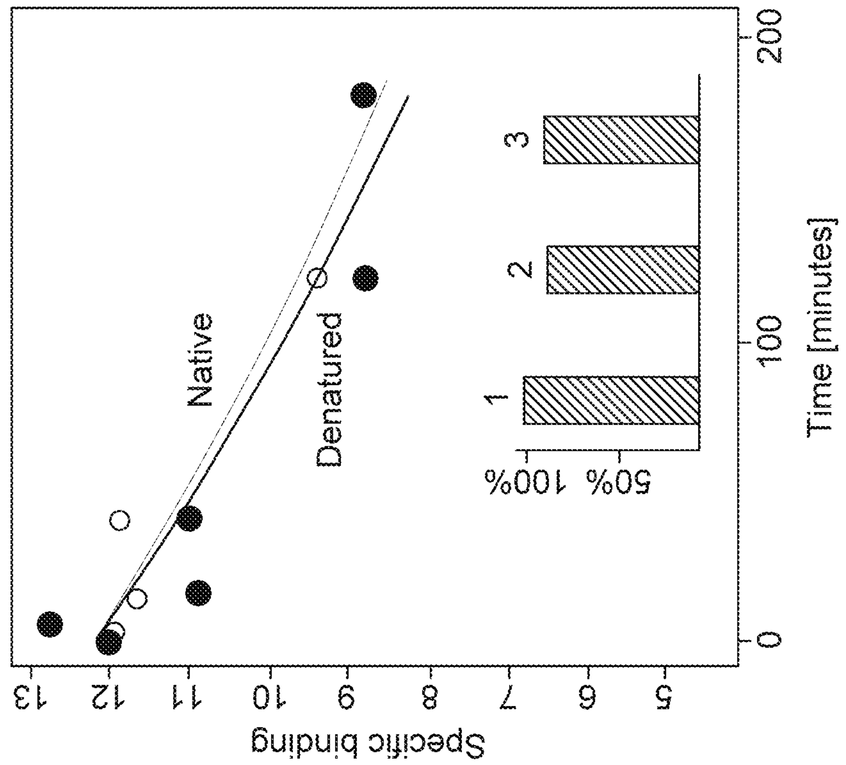
Figure 15E:
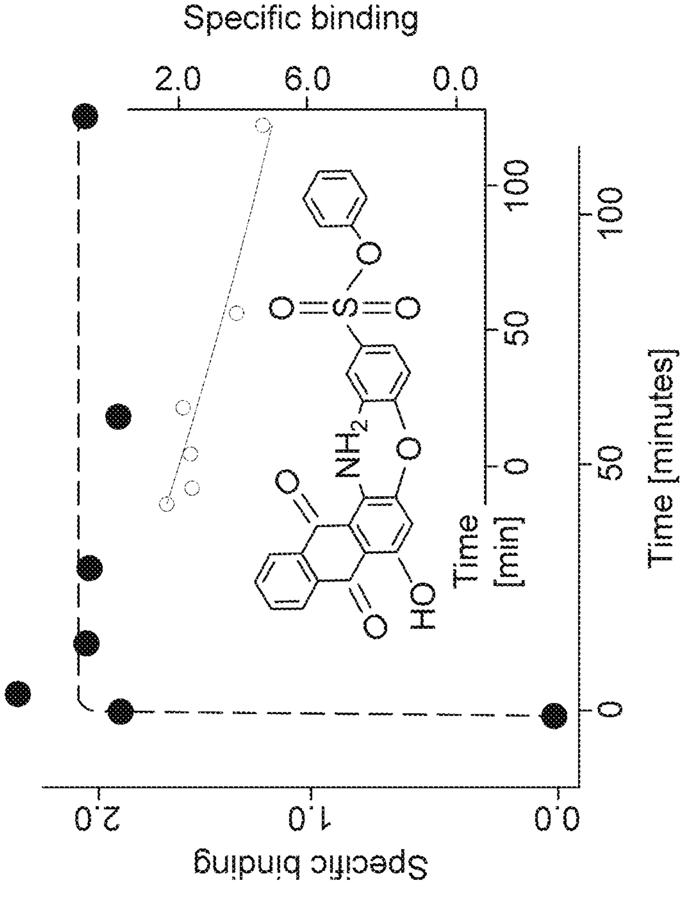

When paint molecules are mixed with a native pre-formed protein complex (FIG. 15, FIG. 8), the paints non-covalently coat all external sites on the protein within minutes, but cannot gain access to the solvent inaccessible, hidden protein-protein interaction domains (FIG. 15*a*). Each paint molecule spans approximately 3 amino acids or less (FIG. 15*a*. Following protein painting, the unbound paints are removed, and the protein-protein interactions are dissociated. This rapid treatment leaves the paint molecules coating all surface areas of the protein that were not participating in the interaction interface (FIG. 15*b*). Following painting, the proteins are dissociated, linearized, digested with proteolytic enzymes, and sequenced by mass spectrometry (MS)[6] (FIG. 15*b*). The paint molecules remain non-covalently bound even after the proteins are reduced and alkylated (FIG. 15*c-f*).

Proteolytic enzymes such as trypsin will not cleave the protein regions that are "painted" (FIG. 11). Following proteolysis, therefore, peptides for MS, will exclusively be generated from the unmodified opposing domains where the proteins were in intimate contact at the time of the painting (FIG. 15*b*). The instant technology works in a manner completely opposite to protein crosslinking methods. Applicants can readily differentiate internal solvent inaccessible residues, within a single protein, from contact points between protein partners, because we separately paint and compare the MS sequence of the native folded proteins before and after they are dissociated. This comparison reveals opposing peptide sequences only found when the proteins are bound together (FIG. 15*a*).

Paint chemistries were selected because they have: a) extremely rapid on-rates ($M^{-1}$ $sec^{-1}$) and very slow off-rates ($<10^{-5}$ $sec^{-1}$, FIG. 9) that are ten to 100 times higher than most protein-protein interactions (FIG. 15*c-e*), b) remain bound following protein dissociation or denaturation with 2 M Urea (FIG. 15*f*, FIG. 9), and c) bind to multiple sites on the exposed protein surface to achieve complete masking of all the trypsin cleavage sites (FIG. 15*c-e*, FIG. 11). A pulse of small molecule paints is applied in vast molar excess to native protein pre-formed complexes (FIG. 15, FIG. 8). Using a Sephadex G25 molecular sieve quick spin column, saturation binding equilibrium can be reached in 5 minutes and non-bound paint molecules can be removed in a one-minute column pass-through (FIG. 15*c-e*, FIG. 8). Protein painting takes advantage of the elevated energy barrier for dissociation once proteins have formed a complex[7,8]. The rapid on-rate and slow off-rate of our paints insures that the paint molecules will a) coat the complex prior to potential spontaneous off-rate dissociation of the pre-formed protein-protein interactions, and b) remain bound through pre-processing for MS.

According to the O-ring theory of hot spots, water or solvent is excluded from the hot spot by a surrounding ring of energetically neutral residues. Occlusion of bulk solvent slows dissociation. The instant organic dye paint solutions are excluded from entering the hot spot, thereby taking advantage of this principle. Residues that favor both hydrogen bonding and hydrophobic interactions (Arg, Trp, and Tyr) are much more likely to be located within hot spots and these are the same residues that are important for protease (trypsin) recognition and cleavage[9], compared to other residues (Val, Leu, Ser). Paints bind with high affinity near trypsin cleavage consensus sites containing charged amino acids such as Arg or Lys, and remain bound after protein partner dissociation, reduction and alkylation (FIG. 15*c-f*, FIG. 10).

We evaluated the power of protein painting by using it to study the multiple hot spots participating in the three-way interaction of IL1b ligand, its receptor IL1R1, and the accessory protein IL1RAcP (FIG. 16). Interleukin signaling requires the interaction of all three proteins. Aberrant function of this complex is involved in a variety of diseases, including cancer, rheumatoid arthritis, systemic lupus erythematosus, inflammatory bowel disease, systemic vasculitis[14], neonatal bronchial dysplasia, and inflammatory bone and cartilage destruction.

First, protein painting was applied to the binary interaction between IL1b and its receptor IL1RI. This revealed interface peptides associated with opposing contact points between the bound ligand and its receptor and corresponded to the known x-ray crystallography predictions of contact residues (FIG. 16*a*, FIG. 12).

Next, protein painting was extended to the receptor, the ligand, and the accessory protein, all painted as a single complex: the results revealed a 3-way "hot spot", where all three proteins are in close approximation to each other (FIG. 16*b*), that constitutes a previously unstudied target for potentially blocking IL1b receptor signaling. The MS identified sequences revealed by our method on each separate protein in the complex were all adjacent and juxtaposed to each other based on 3-D modeling (FIG. 16*a*, 16*b*). The highly evolutionarily conserved IL1RAcP sequence that emerged (FIG. 13, 14) indicates that the accessory protein, required for interleukin signaling binds to the receptor-ligand complex in a single very narrow region (orthogonal views FIG. 16*b*), is fully consistent with crystallography data (FIG. 13), and provides new functional information that supports the hypothesis that rotation of the third immunoglobulin domain in IL1RAcP is necessary for it to touch the composite face of the receptor and ligand (PBD ID #4DEP).

Figure 13A:
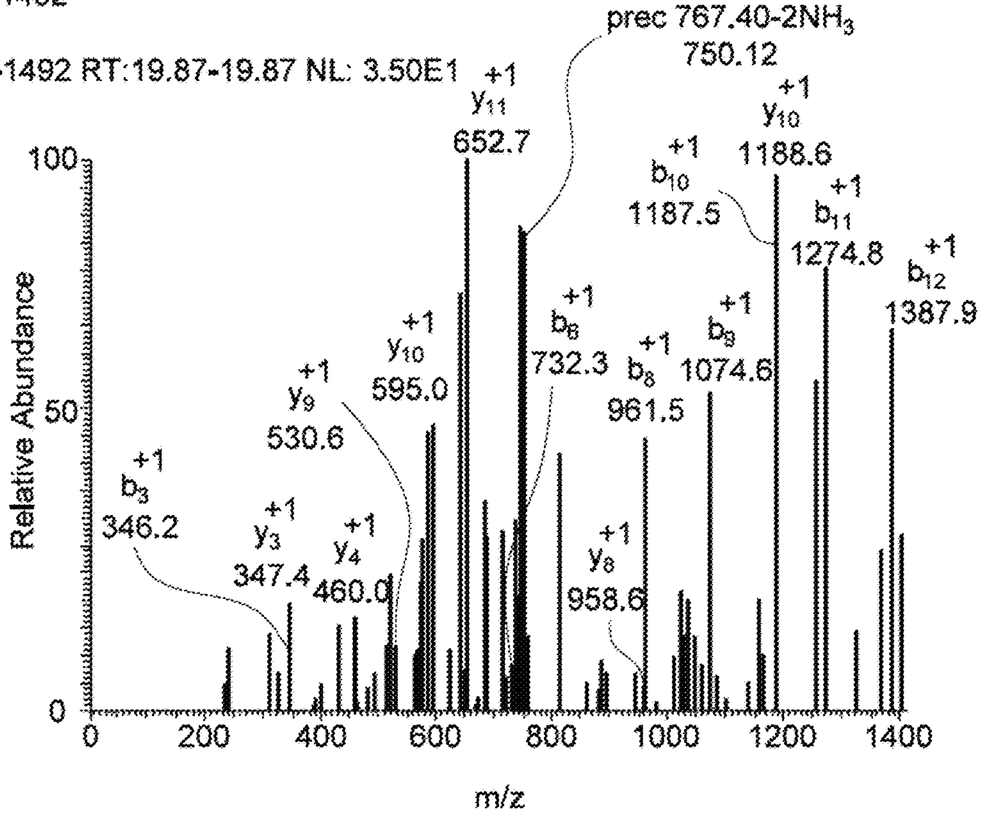
Figure 13B:
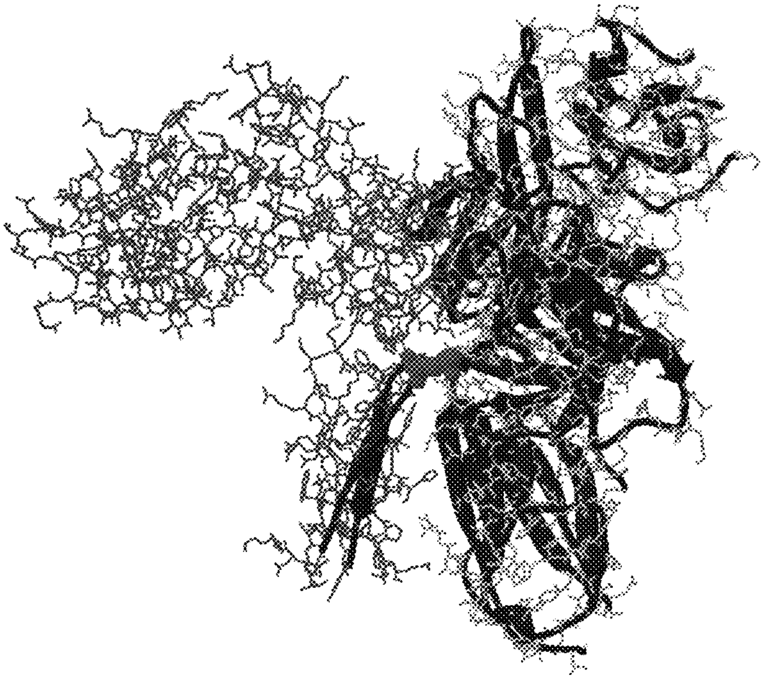
Figures 16D, 16E, 16F:
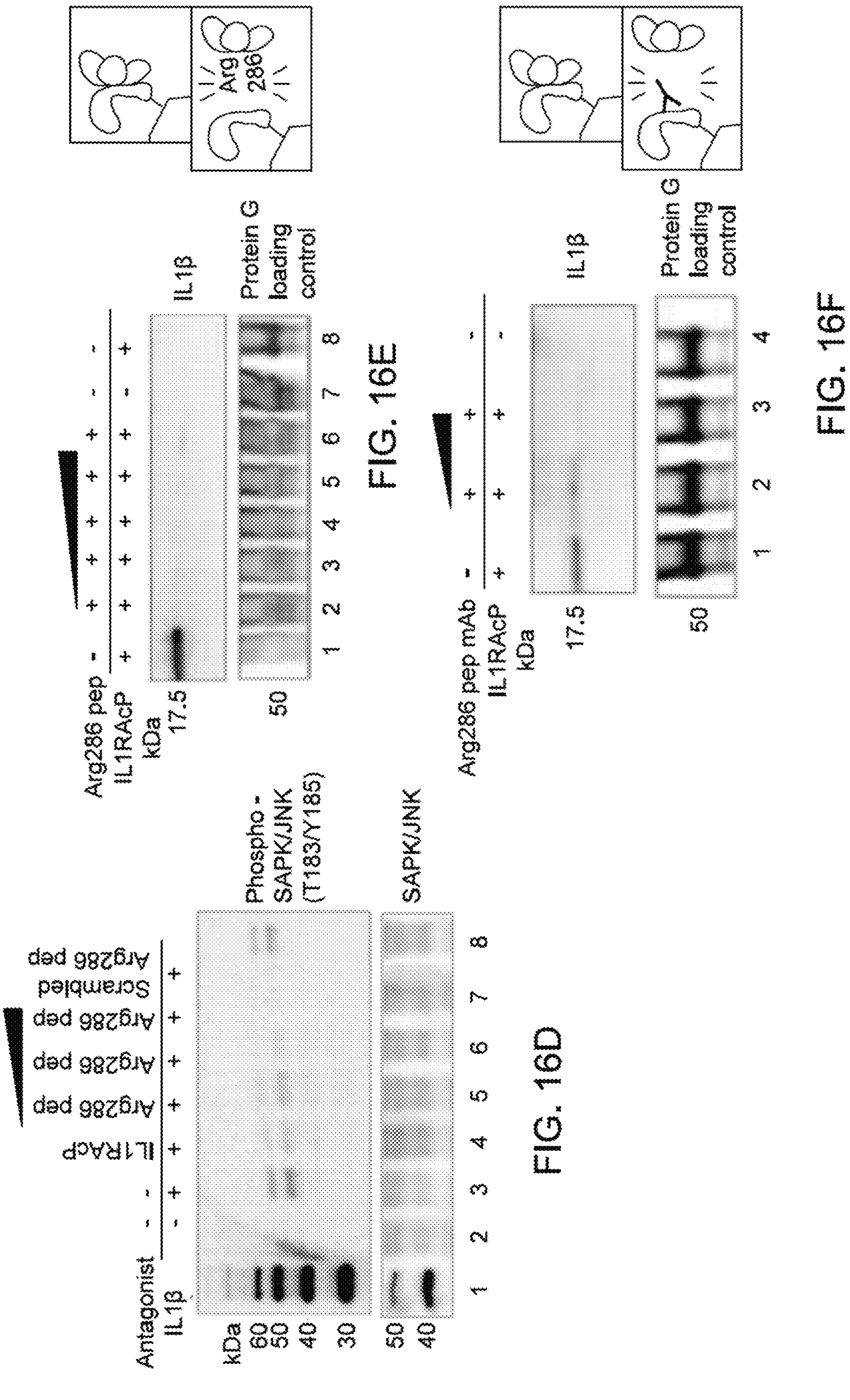

To test the mechanistic significance of the sequence data, IL1b stimulated cells (NCI-ADR-RES[19]) were treated with synthetic beta loop peptides corresponding to the three-way interface (FIG. 16*d*, FIG. 13). Synthetic peptides corresponding to the narrow IL1RAcP contact point Arg286, completely blocked IL1β ligand-stimulated signaling, in a dose dependent manner (FIG. 16*d*). To verify that this domain was functionally active, it was tested whether the peptide blocked the formation of the 3-protein complex in vitro (FIG. 16*e*), by pulling down IL1b in the complex through a His-tagged IL1RAcP partner. It was found that the Arg286 peptide completely blocked IL1RAcP 3-way binding to the receptor ligand complex (FIG. 16*e*). Finally, to further verify the importance of the IL1RAcP sequence identified by protein painting, a monoclonal antibody was raised against this domain. The monoclonal antibody blocked the 3 protein complex formation in a dose dependent manner (FIG. 16*f*). Since a) the Arg286 peptide, or the monoclonal antibody, act on opposite faces of the binding site, and can both block pull-down of the ligand-receptor complex, and, b) the peptide itself can substitute for the entire soluble IL1RAcP protein as a competitive inhibitor (FIG. 16*e*), this sequence may be necessary for the interaction of the accessory protein with the other two partners. The Arg286 peptide and/or the monoclonal antibodies directed against this region constitute novel therapies to potentially block interleukin signaling in vivo.

The data demonstrates that protein painting can uncover functionally meaningful sequence domains within hot spots. Protein painting can probe protein binding partners for which little or no interaction domain information is known ahead of time, or provide functional information to confirm or extend computational or analytical approaches. While the size of the paint molecules is less than 3 amino acids, the actual resolution of the hot spot domain we can identify depends on the local density of trypsin cleavage sites (average size of tryptic peptides are 9 amino acids). Although known hot spot regions are enriched in charged amino acids comprising trypsin cleavage consensus sites, we may lose resolution for domains with sparse cleavage sites. This limitation is reduced if a sparse region of trypsin residues on one side of the protein-protein interface is compensated by a trypsin cleavage site on the opposite face (FIG. 12, 13).

Protein painting can also be applied to a population of native proteins containing a subset of interacting members. The direct output will be the amino acid sequences derived only the unpainted subset of protein domains that were participating in the protein-protein interactions at the time the paint molecules were introduced, thus comprising a new class of protein interaction information. Protein painting is readily adaptable to high-speed automation and analysis.

(2) Methodology

A. Molecular Painting for Mass Spectrometry

Method overview: (step 1) Proteins are pulsed with 10 molar excess small molecule molecular paints. (step 2) Gel filtration chromatography is used to retain the unbound paint molecules in the column (Sephadex G-25, Roche). (step 3) The protein is denatured with 2 M urea. (step 4) Proteins are linearized by dithiothreitol (DTT) reduction and iodoacetamide alkylation. (step 5) Linearized proteins are subjected to trypsin digestion. Trypsin cleavage occurs at sites that are not masked by the molecular paint. (step 6) Tryptic fragments are analyzed by reversed-phase liquid chromatography nanospray tandem mass spectrometry (LC-MS/MS).

As a model protein to demonstrate that the trypsin cleavage sites are blocked by the molecular paints, Carbonic anhydrase II (CA, Sigma) was used for mass spectrometry. Carbonic anhydrase II (CA, Sigma), at a concentration of 65 pmoles in 50 μl PBS (phosphate buffered saline, 1× Invitrogen), was mixed with 10 molar excess of the following molecular paints dissolved in PBS:

1) disodium; 1-amino-9,10-dioxo-4-[3-(2-sulfonatooxyethylsulfonyl) anilino] anthracene-2-sulfonate (RBB) (Acros Organics);

2) sodium 4-(4-(benzyl-et-amino)-ph-azo)-2,5-di-cl-benzenesulfonate (AO50) (Sigma);

3) Phenyl 4-[(1-amino-4-hydroxy-9,10-dioxo-9,10-dihydro-2-anthracenyl)oxy]benzenesulfonate (R49) (Sigma);

4) disodium; 4-amino-3-[[4-[4-[(1-amino-4-sulfonatonaphthalen-2-yl)diazenyl] phenyl] phenyl] diazenyl] naphthalene-1-sulfonate (CR) (Sigma).

The expected peptide sequences should be inversely proportional to the number of paint blocked trypsin digestion sites.

As a control to identify solvent accessible surface areas, protein solutions were prepared in parallel at the same concentrations without adding paint molecules.

For any protein, the percentage coverage of tryptic digestion peptides in MS is a function of the peptide size, charge, MS sensitivity and other factors that are individual to the specific instrument and protocol. Following painting, for the protein of interest, a concentration of paint molecules should be used that blocks all of the trypsin cleavage sites for the protocol used. If this is first established, when the protein in question is complexed with another protein and one of the cleavage sites is protected from the exposure to the molecular paint because it is part of a protein-protein contact point, then this cleavage site will emerge as positive contact signal. Thus, the emergence of a peptide in the complexed state but not in the non-complexed state is considered a true positive.

To identify functional protein-protein interaction domains, three equimolar concentrations of Interleukin ligand, its cognate receptor, and its accessory proteins were selected as a proof of concept protein complex. Interleukin 1β (IL1β, Gibco, 65 pmoles in 50 μl PBS), Interleukin 1 receptor type I (IL1RI, Adipogen, 65 pmoles in 50 μl PBS), and Interleukin 1 receptor accessory protein (IL1RAcP, Novoprotein, 65 pmoles in 50 μl PBS), were allowed to interact for one hour at room temperature under rotation. Protein complexes were mixed with 10 molar excess of the following 4 molecular paints dissolved in PBS:

1) N-(4-{bis[4-(dimethylamino)phenyl]methylene}-2,5-cyclohexadien-1-ylidene)methanaminium chloride (MV) (Fisher), 2) 3,3'-Diethylthiacarbocyanine iodide (DECI) (Sigma), 3) 8-Anilino-1-naphthalenesulfonic acid (ANSA) (Sigma), and 4) disodium; 1-amino-9,10-dioxo-4-[3-(2-sulfonatooxyethylsulfonyl)anilino]anthracene-2-sulfonate (RBB) (Acros Organics).

As a control to identify solvent accessible surface areas, protein solutions were prepared in parallel at the same concentrations without adding paint molecules. Additional controls were prepared to demonstrate that each individual protein of the interleukin-receptor-accessory protein complex could be coated by the dye. Equal quantities of unbound, Interleukin 1β, IL1RI, or IL1RAcP were mixed individually with each of the four molecular paints (3 proteins×4 paints, n=12) in a 1:10 molar ratio (protein: molecular paint). The expected peptide sequences should be inversely proportional to the number of paint blocked trypsin digestion sites.

The solutions were immediately passed through a size sieving Sephadex column (PD MiniTrap G 25, GE Healthcare) and the flow through was collected, denatured with urea (final concentration 2M), reduced with 1 M dithiothreitol (Sigma, 15 minutes at 37° C.), alkylated with 0.5 M iodoacetamide (Sigma, 15 minutes, room temperature in the dark), and digested with trypsin (Promega) at 1:10 w/w protease/protein ratio for 2 hours at 37° C. Tryptic peptides were purified by Zip-Tip (Millipore) following manufacturer's instructions, and analyzed by reversed-phase liquid chromatography nanospray tandem mass spectrometry (LC-MS/MS) using an LTQ-Orbitrap mass spectrometer (ThermoFisher).

B. Mass Spectrometry Analysis

After sample injection by autosampler, the C18 column (0.2×50 mm, Michrom Bioresources, Inc.) was washed for 2 minutes with mobile phase A (0.1% formic acid) and peptides were eluted using a linear gradient of 0% mobile phase B (0.1% formic acid, 80% acetonitrile) to 50% mobile phase B in 40 minutes at 500 nanoliter/min, then to 100% mobile phase B for an additional 5 minutes. The LTQ mass spectrometer (Thermo) was operated in a data-dependent mode in which each full MS scan was followed by five MS/MS scans where the five most abundant molecular ions were dynamically selected for collision-induced dissociation (CID) using a normalized collision energy of 35%. Tandem mass spectra were searched against the NCBI human database with SEQUEST using tryptic cleavage constraints. High-confidence peptide identifications were obtained by applying the following filter criteria to the search results: Xcorr versus charge>=1.9, 2.2, 3.5 for 1+, 2+, 3+ ions; ΔCn>0.1; probability of randomized identification<=0.01.

C. Association-Dissociation Kinetics Determination

To measure the protein-dye equilibrium kinetics, the maximum absorbance for each molecular paint described above was identified on a UV-2501PC spectrophotometer (Shimadzu) provided with UV probe 2.10 software (FIG. 9) in the wavelength region 400-800 nm and using a path length of 1 cm. Differential spectral titrations were performed in PBS at 25° C.

Carbonic anhydrase II (2 micrograms in 50 μl PBS) was mixed with 10 molar excess of the following molecular paints dissolved in PBS:

1) disodium 1-amino-9,10-dioxo-4-[3-(2-sulfonatooxyethylsulfonyl) anilino] anthracene-2-sulfonate (RBB);

2) sodium 4-(4-(benzyl-et-amino)-ph-azo)-2,5-di-cl-benzenesulfonate (AO50);

3) Phenyl 4-[(1-amino-4-hydroxy-9,10-dioxo-9,10-dihydro-2-anthracenyl)oxy]benzenesulfonate (R49);

4) disodium; 4-amino-3-[[4-[4-[(1-amino-4-sulfonatonaphthalen-2-yl)diazenyl] phenyl] phenyl] diazenyl] naphthalene-1-sulfonate (CR).

Protein-paint solutions were immediately passed through a Sephadex column (PD MiniTrap G 25, GE Healthcare) and the flow through was collected. The maximum absorbance value of the flow through for the protein-paint complex was registered on the UV-2501PC spectrophotometer. Non-linear regression calculations to identify the fitted curve of the association and dissociation rates were performed in R software (worldwideweb.rproject.org/index.html).

D. Crystal Structure Interface Characterization from Protein Databank Entries

Interface analysis of IL1β-IL1RI and IL1β-IL1RI-IL1RAcP complex structures was performed using the structural analysis module PDBe PISA v1.47 (Protein Interface and Assembly) on the PDB entry 1ITB and 4DEP, respectively. Molecular structures were visualized with Swiss-PdbViewer[2] version 4.1.

E. Peptide Synthesis and Characterization

Peptides were custom produced by Peptide 2.0, Inc. using standard solid phase procedures. Peptide purity (>98%) was assessed by HPLC and MS.

F. Monoclonal Antibodies

Mouse IgG monoclonal antibodies (Abmart) were raised against the functionally active portion of IL1-RAcPArg286 peptide (TINESISHSRTEDETRTQILS) (SEQ ID NO:6). An immunogenicity-amplified antigen display method was used. Synthetic genes encoding multiple Arg286 peptide epitopes were inserted into a proprietary DNA vector consisting of Immunogenicity Enhancement Factors and DNA sequences. When the vector was expressed in E. coli, particulate, highly immunogenic recombinant proteins that contain multiple Arg286 peptide sequences were produced. Multiple mouse immunizations, multiple fusions and multiple cell line selections were conducted in parallel in order to maximize chances of producing a high affinity and high specificity antibody. Resulting antibodies were qualified with 1) solid phase ELISA against Arg286 peptide and selected if they had an ELISA titer higher than 1:100,000, and 2) western blotting and selected if they showed single band reactivity with the IL1RAcP protein (Novoprotein).

G. Cell Cultures

NCI/ADR-RES cells (Division of Cancer Treatment and Diagnosis, National Cancer Institute) were cultured in Dulbecco's modified Eagle's medium (Gibco) with 10% fetal bovine serum (ATCC), and 2 mM L-glutamine (ATCC) at 37° C., 5% $CO_2$, in a humidified environment. NCI/ADR-RES cells ($2\times10^6$ cells/well) were plated into 6-well tissue culture dishes. The following day, cells were pre-treated for 30 minutes with soluble IL1RAcP (1 μg/mL) lacking the trans-membrane domain, Arg286 peptide (TINESISHSRTEDETRTQILS, 3.3, 16.7 and 33 μM) (SEQ ID NO:6) and a scrambled peptide obtained by randomly shuffling Arg286 sequence (HLRNISRISSITDTSETETEQ, 33 μM) (SEQ ID NO:7). Cells were washed with Dulbecco's modified Eagle's medium with 10% fetal bovine serum, and 2 mM glutamine and were stimulated with IL1β at 10 ng/ml for 30 min. Following incubation, cells were washed in ice-cold PBS, incubated with 100 μl of cell lysis buffer (10% Bond Breaker TCEP solution (Thermo Scientific), 45% T-PER tissue protein extraction reagent (Thermo Scientific) and 45% Novex Tris Glycine SDS sample buffer 2× (Invitrogen)), scraped, transferred to Eppendorf tubes, and heated at 100° C. for 10 minutes. Cell lysates were analyzed by western blotting.

H. Immunoprecipitation

IL1 β (0.44 μg/mL), IL1RI (2 μg/mL) and 6×His-tagged IL1RAcP (0.72 μg/mL) were incubated with Arg286 peptide (6.7, 3.3, 1.7, 0.8 and 0.4 μM) in 50 μl of PBS for one hour at room temperature under rotation. In parallel, IL1β, IL1RI and 6×His-tagged IL1RAcP were allowed to interact without Arg286 peptide as a positive control. IL1β, and 6×His-tagged IL1RAcP were allowed to interact in absence of IL1RI as a negative control. After 1 hour, protein mixtures were incubated with magnetic beads decorated with anti-6His mouse monoclonal antibody obtained as follows. BcMag Protein G Magnetic Beads (50 μl, Bioclone) were washed 3 times with washing buffer (57.7 mM $Na_2HPO_4$, 42.3 mM $NaH_2PO_4$, pH 7.0) and incubated with anti-6×His mouse monoclonal antibody (1 μg, Abcam) for 30 minutes under rotation. Magnetic beads were separated from the supernatant with neodymium magnets, washed three times with washing buffer (57.7 mM $Na_2HPO_4$, 42.3 mM $NaH_2PO_4$, pH 7.0) and incubated with protein mixtures for one hour at room temperature under rotation. Magnetic beads were separated from the supernatant with neodymium magnets and washed three times with washing buffer (57.7 mM $Na_2HPO_4$, 42.3 mM $NaH_2PO_4$, pH 7.0). Immuno-precipitated proteins were eluted with 20 μl of 4× sample buffer (10 minutes, 70° C.). Immuno-precipitated proteins were analyzed by western blotting.

I. Western Blotting

Proteins were separated by 1-D gel electrophoresis in 4-20% Tris-Glycine gel in the presence of Tris-Glycine SDS running buffer with the following run conditions: 125 V, 90 minutes. Proteins were then transferred onto Immobilion PVDF membrane. The membrane was blocked with PBS supplemented with 0.2% (w/v) I-Block and 0.1% Tween 20 for 1 hour at room temperature, and then with antibody raised against phospho—SAPK/JNK (T183/Y185), SAPK/JNK, and IL1β (Cell Signaling Technology) overnight at 4° C. under continuous agitation. After washes with PBS supplemented with 0.2% I-Block (w/v) and 0.1% Tween 20, immunoreactivity was revealed by using species-specific horseradish peroxidase conjugated anti-IgG secondary antibody (Invitrogen) and the enhanced chemiluminescence system (ECL Plus, Pierce). The protein blot was imaged using a Kodak 4000MM.

J. BLAST Analysis

To confirm that the IL1RAcP peptide (TINESISHSRTEDETRTQILS) (SEQ ID NO:6) selected by protein painting was conserved among species, a BLAST search was performed with Protein Basic Local Alignment Search Tool (pblast) available at NCBI.

What is claimed is:

1. A method for determining a contact region within a single folded protein or between a protein complexed with another molecule, comprising (a) introducing a mixture comprising an organic masking molecule to said protein, wherein said organic masking molecule binds to an exposed site on said protein or protein complex, thereby coating said protein;

(b) dissociating said protein or protein complex, such that the organic masking molecule coats an area of the protein or protein complex excluding the contact region, wherein the organic masking molecule remains bound to the area of the protein or protein complex excluding the contact region;

(c) contacting the contact region with a proteolytic enzyme, thereby digesting the contact region with the proteolytic enzyme; and (d) sequencing the contact region after contacting the contact region with the proteolytic enzyme.

2. The method of claim 1, wherein said organic masking molecule is an aryl hydrocarbon containing organic compound less than 30 Angstroms in total length, or a salt or a solvate thereof.

3. The method of claim 2, wherein said aryl hydrocarbon containing organic compound has the following structure formula:

(I)

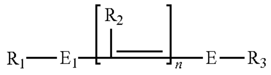

Q

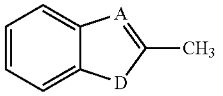

Q'

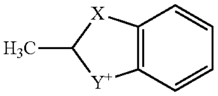

Polymethine compounds wherein $R_1$ represents H, halo, $CO_2H$, $NO_2$, SH, $NR_5R_6$, C1-6 alkyl, C1-6 alkoxy, cyano, carbonyl, pyrrolidinyl, pyrrolyl, pyrazolyl, imidazolyl, or triazolyl;

$R_5$, $R_6$ represent H or C1-4 alkyl;

$E_1$ represents benzene ring or ring Q;

A represents CH or N;

D represents S, NH, N—C1-3 alkyl, O, or $CH_2$;

$R_2$ represents H, C1-4 alkyl, halo-C1-4 alkyl, OH, or cyano;

n represents an integer of 1-4;

E=benzene ring or ring Q';

X represents CH or N

Y represents S, NH, N—C1-3 alkyl, O, or $CH_2$ $R_3$=H, halo, $CO_2H$, $NO_2$, SH, $NR_5R_6$, C1-6 alkyl, C1-6 alkoxy, cyano, carbonyl, pyrrolidinyl, pyrrolyl, pyrazolyl, imidazolyl, or triazolyl;

(II)

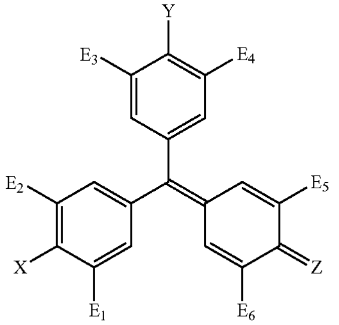

Triarylmethane compounds wherein X and Y represent H, $NR_1R_2$, sulfo, halo, $CO_2H$, $NO_2$, SH, C1-6 alkyl, or C1-6 alkoxy;

Z represents $NR_1R_2$, sulfo, O, $CO_2H$, $NO_2$, C1-6 alkyl, or C1-6 alkoxy;

$R_1$ $R_2$ represent H, C1-6 alkyl, or sulfophenyl;

$E_1$, $E_2$, $E_3$, $E_4$, $E_5$, $E_6$ represent H, sulfo, C1-6 alkyl, halo, $CO_2H$, $NO_2$, or SH;

(III)

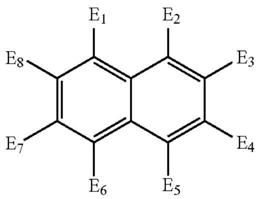

Naphthalene derivatives wherein $E_1$, $E_2$, $E_3$, $E_4$, $E_5$, $E_6$ represent H, C1-6 alkyl, C1-6 alkoxy, carbonyl, sulfo, $NO_2$, $NR_1R_2$, azetidinyl, or thiazolidinyl;

$R_1$, $R_2$ represent H or phenyl;

(IV)

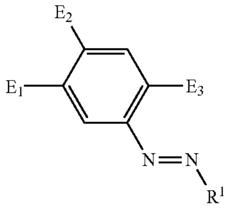

Q

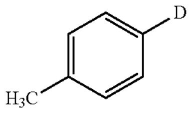

Q'

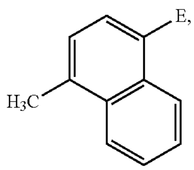

Aryl azo compounds wherein $E_1$, $E_2$, $E_3$ represent H, halo, sulfo, C1-6 alkyl, or C1-6 alkyl aryl;

R1 represents ring Q or ring Q';

D represents H or $NR_2R_3$;

$R_2$, $R_3$ represent C1-6 alkyl or C1-6 alkyl aryl;

E represents H, OH, or C1-6 alkyloxy;

(V)

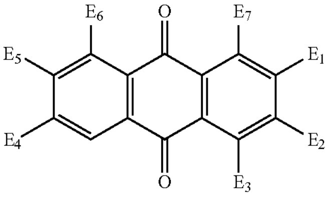

Q

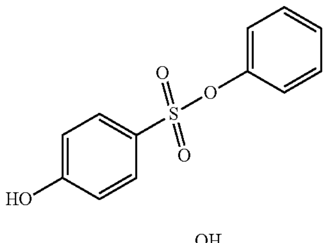

Q'

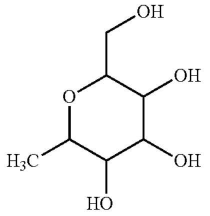

-continued

Q''

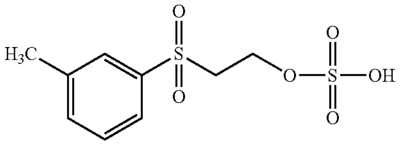

Anthraquinones wherein $E_1$ represents H, NH, sulfo, Q, Q', C1-6 alkyl, OH, or carboxy;

$E_2$ represents H, NH, OH, C1-6 alkyl, or sulfo;

$E_3$ represents H, NH, OH, $NR_1R_2$, sulfo, or C1-6 alkyl;

$R_1$, $R_2$ represent H or Q'';

$E_4$, $E_5$, $E_6$, $E_7$ represent H, OH, NH, sulfo, C1-6 alkyl, or carboxy;

(VI)

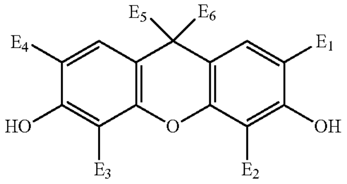

Q

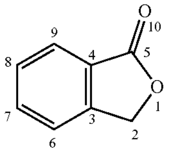

Xanthenes wherein $E_1$, $E_2$, $E_3$, $E_4$ represent H, $NO_2$, OH, Halo, or C1-6 alkyl;

$E_5$, $E_6$ represent H or Carbon in position 3 and oxygen in position 1 in group Q; or (VII)

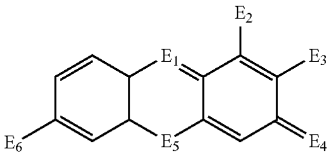

Thiazine wherein $E_1$ represents N, O, or S;

$E_2$, $E_3$ represent H or C in aryl;

$E_4$ represents O, N, or $NR_1R_2$;

$R_1$, $R_2$ represent C1-6 alkyl;

$E_5$ represents N, O, or S;

$E_6$ represents H, NH, or NC1-6 alkyl.

4. The method of claim 2, wherein said aryl hydrocarbon containing organic compound has the following structure formula:

(I)

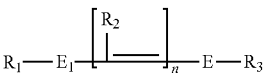

-continued

Q

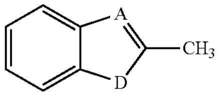

Q'

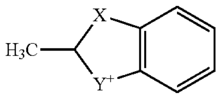

Polymethine compounds wherein $R_1$ represents H, halo, $CO_2H$, $NO_2$, SH, $NR_5R_6$, C1-6 alkyl, C1-6 alkoxy, cyano, carbonyl, pyrrolidinyl, pyrrolyl, pyrazolyl, imidazolyl, or triazolyl;

$R_5$, $R_6$ represent H or C1-4 alkyl;

$E_1$ represents benzene ring or ring Q;

A represents CH or N;

D represents S, NH, N—C1-3 alkyl, O, or $CH_2$;

$R_2$ represents H, C1-4 alkyl, halo-C1-4 alkyl, OH, or cyano;

n represents an integer of 1-4;

E=benzene ring or ring Q';

X represents CH or N;

Y represents S, NH, N—C1-3 alkyl, O, or $CH_2$;

$R_3$=H, halo, $CO_2H$, $NO_2$, SH, $NR_5R_6$, C1-6 alkyl, C1-6 alkoxy, cyano, carbonyl, pyrrolidinyl, pyrrolyl, pyrazolyl, imidazolyl, or triazolyl.

5. The method of claim 2, wherein said aryl hydrocarbon containing organic compound has the following structure formula:

(II)

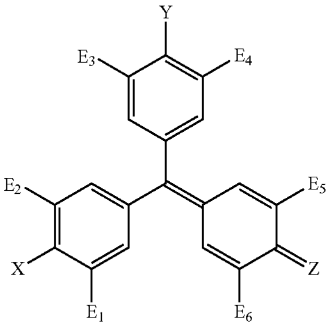

Triarylmethane compounds wherein X and Y represent H, $NR_1R_2$, sulfo, halo, $CO_2H$, $NO_2$, SH, C1-6 alkyl, or C1-6 alkoxy;

Z represents $NR_1R_2$, sulfo, O, $CO_2H$, $NO_2$, C1-6 alkyl, or C1-6 alkoxy;

$R_1$, $R_2$ represent H, C1-6 alkyl, or sulfophenyl;

$E_1$, $E_2$, $E_3$, $E_4$, $E_5$, $E_6$ represent H, sulfo, C1-6 alkyl, halo, $CO_2H$, $NO_2$, or SH.

6. The method of claim 2, wherein said aryl hydrocarbon containing organic compound has the following structure formula:

(III)

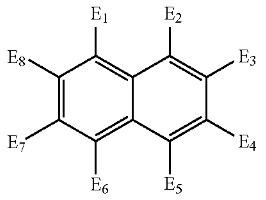

Naphthalene derivatives wherein $E_1$, $E_2$, $E_3$, $E_4$, $E_5$, $E_6$ represent H, C1-6 alkyl, C1-6 alkoxy, carbonyl, sulfo, $NO_2$, $NR_1R_2$, azetidinyl, or thiazolidinyl;

$R_1$, $R_2$ represent H or phenyl.

7. The method of claim 2, wherein said aryl hydrocarbon containing organic compound has the following structure formula:

(IV)

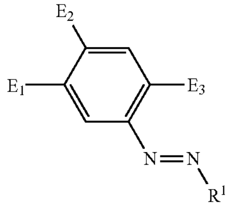

Q

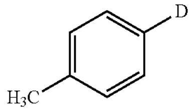

Q'

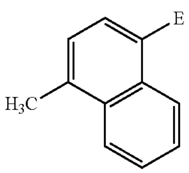

Aryl azo compounds wherein $E_1$, $E_2$, $E_3$ represent H, halo, sulfo, C1-6 alkyl, or C1-6 alkyl aryl;

R1 represents ring Q or ring Q';

D represents H or $NR_2R_3$;

$R_2$, $R_3$ represent C1-6 alkyl or C1-6 alkyl aryl;

E represents H, OH, or C1-6 alkyloxy.

8. The method of claim 2, wherein said aryl hydrocarbon containing organic compound has the following structure formula:

(V)

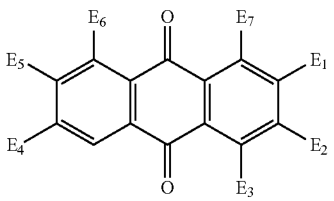

Q

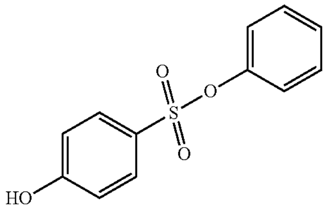

Q'

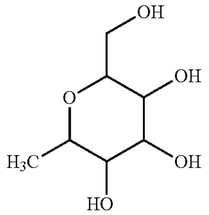

Q''

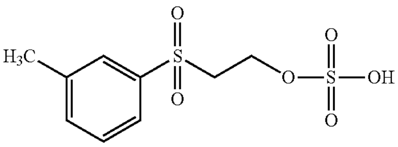

Anthraquinones wherein $E_1$ represents H, NH, sulfo, Q, Q', C1-6 alkyl, OH, or carboxy;

$E_2$ represents H, NH, OH, C1-6 alkyl, or sulfo;

$E_3$ represents H, NH, OH, $NR_1R_2$, sulfo, or C1-6 alkyl;

$R_1$, $R_2$ represent H or Q'';

$E_4$, $E_5$, $E_6$, $E_7$ represent H, OH, NH, sulfo, C1-6 alkyl, or carboxy.

9. The method of claim 2, wherein said aryl hydrocarbon containing organic compound has the following structure formula:

(VI)

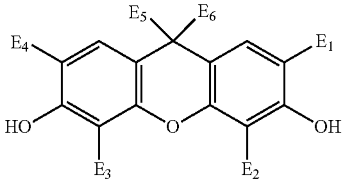

Q

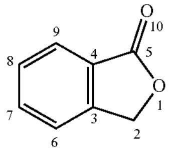

Xanthenes wherein $E_1$, $E_2$, $E_3$, $E_4$ represent H, $NO_2$, OH, Halo, or C1-6 alkyl;

$E_5$, $E_6$ represent H or Carbon in position 3 and oxygen in position 1 in group Q.

10. The method of claim 2, wherein said aryl hydrocarbon containing organic compound has the following structure formula:

(VII)

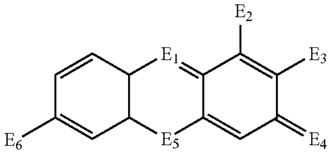

Thiazine wherein $E_1$ represents N, O, or S;

$E_2$, $E_3$ represent H or C in aryl;

$E_4$ represents O, N, or $NR_1R_2$;

$R_1$, $R_2$ represent C1-6 alkyl;

$E_5$ represents N, O, or S;

$E_6$ represents H, NH, or NC1-6 alkyl.

11. The method of claim 1, wherein the proteolytic enzyme is trypsin.

* * * * *